(12) United States Patent
Edwards, Jr. et al.

(10) Patent No.: US 10,300,120 B2
(45) Date of Patent: May 28, 2019

(54) PHARMACEUTICAL COMPOSITIONS AND METHODS TO VACCINATE AGAINST DISSEMINATED CANDIDIASIS AND OTHER INFECTIOUS AGENTS

(71) Applicant: Los Angeles Biomedical Research Institute at Harbor—UCLA Medical Center, Torrance, CA (US)

(72) Inventors: John E. Edwards, Jr., Palos Verdes Estates, CA (US); Ashraf S. Ibrahim, Irvine, CA (US); Bradley J. Spellberg, Rancho Palos Verdes, CA (US); Yue Fu, Carson, CA (US); Scott G. Filler, Rancho Palos Verdes, CA (US); Michael R. Yeaman, Redondo Beach, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 15/014,440

(22) Filed: Feb. 3, 2016

(65) Prior Publication Data
US 2016/0220648 A1  Aug. 4, 2016

Related U.S. Application Data

(63) Continuation of application No. 12/987,949, filed on Jan. 10, 2011, now abandoned, which is a continuation of application No. 11/327,197, filed on Jan. 6, 2006, now abandoned.

(51) Int. Cl.
| | | |
|---|---|---|
| A61K 39/085 | (2006.01) | |
| A61K 39/00 | (2006.01) | |
| A61K 45/06 | (2006.01) | |
| C07K 16/14 | (2006.01) | |

(52) U.S. Cl.
CPC .......... *A61K 39/0002* (2013.01); *C07K 16/14* (2013.01); *A61K 39/085* (2013.01); *A61K 2039/5156* (2013.01); *A61K 2039/58* (2013.01); *C07K 2317/76* (2013.01)

(58) Field of Classification Search
CPC ...... A61K 2039/55505; A61K 2039/58; A61K 39/0002; A61K 45/06; A61K 2039/5156; A61K 2039/505; A61K 39/085; A61K 38/00; A61K 38/164; A61K 39/00; A61K 2039/55566; A61K 2039/575; A61K 2039/70; C07K 2317/76; C07K 16/14; C07K 16/1271; C07K 14/31; C07K 16/1275; C07K 16/1285; C07K 16/1289; C07K 2317/34; C07K 7/06; C07K 7/08; C07K 2317/14; G01N 33/56938; Y10S 530/825
See application file for complete search history.

(56) References Cited

U.S. PATENT DOCUMENTS

| | | | |
|---|---|---|---|
| 4,346,074 A | 8/1982 | Gilmour et al. | |
| 5,578,309 A | 11/1996 | Cutler et al. | |
| 5,622,939 A | 4/1997 | Jamas et al. | |
| 5,668,263 A | 9/1997 | Hoyer et al. | |
| 5,817,466 A | 10/1998 | Hoyer et al. | |
| 5,961,970 A | 10/1999 | Lowell et al. | |

(Continued)

FOREIGN PATENT DOCUMENTS

| | | |
|---|---|---|
| EP | 2428800 A1 | 3/2012 |
| JP | 2008-540453 A | 11/2008 |

(Continued)

OTHER PUBLICATIONS

Rudinger et al. In: Peptide Hormones. (Ed) JA Parsons, University Park Press, pp. 1-7, 1976.*

(Continued)

*Primary Examiner* — Gary B Nickol
*Assistant Examiner* — Lakia J Jackson-Tongue
(74) *Attorney, Agent, or Firm* — Clark & Elbing LLP

(57) ABSTRACT

The invention provides a vaccine including an isolated Als protein family member having cell adhesion activity, or an immunogenic fragment thereof, with an adjuvant in a pharmaceutically acceptable medium. The invention also provides a method of treating or preventing hematogenously disseminated or mucocutaneous candidiasis. The method includes administering an immunogenic amount of a vaccine an isolated Als protein family member having cell adhesion activity, or an immunogenic fragment thereof, in a pharmaceutically acceptable medium. A method of treating or preventing disseminated candidiasis also is provided that includes administering an effective amount of an isolated Als protein family member having cell adhesion activity, or an functional fragment thereof, to inhibit the binding or invasion of *Candida* to a host cell or tissue. The Als protein family member can be derived from a *Candida* strain selected from the group consisting of *Candida albicans, Candida krusei, Candida tropicalis, Candida glabrata* and *Candida parapsilosis* and the Als protein family member includes Als1p, Als3p, Als5p, Als6p, Als7p or Als9p. Also provided is a method of treating or preventing *Staphylococcus aureus* infections. The method includes administering an immunogenic amount of a vaccine an isolated Als protein family member having cell adhesion activity, or an immunogenic fragment thereof, in a pharmaceutically acceptable medium.

9 Claims, 37 Drawing Sheets
Specification includes a Sequence Listing.

(56) References Cited

U.S. PATENT DOCUMENTS

| | | |
|---|---|---|
| 6,248,329 B1 | 6/2001 | Chandrashekar et al. |
| 6,703,025 B1 | 3/2004 | Patti et al. |
| 6,747,137 B1 | 6/2004 | Weinstock et al. |
| 7,067,138 B1 | 6/2006 | Edwards, Jr. et al. |
| 7,241,613 B1 | 7/2007 | Willins et al. |
| 7,250,286 B2 | 7/2007 | Ellison |
| 7,666,438 B1 | 2/2010 | Patti et al. |
| 7,732,187 B2 | 6/2010 | Cochran et al. |
| 8,541,008 B2 | 9/2013 | Edwards, Jr. et al. |
| 8,709,446 B2 | 4/2014 | Fu et al. |
| 2002/0102262 A1 | 8/2002 | Hook et al. |
| 2002/0146435 A1 | 10/2002 | Evans et al. |
| 2003/0124134 A1 | 7/2003 | Edwards et al. |
| 2003/0217373 A1 | 11/2003 | Green et al. |
| 2004/0116380 A1 | 6/2004 | Jamas et al. |
| 2004/0175731 A1 | 9/2004 | Pier et al. |
| 2005/0287146 A1 | 12/2005 | Patti et al. |
| 2006/0083750 A1 | 4/2006 | Edwards et al. |
| 2007/0027309 A1 | 2/2007 | Weinstock et al. |
| 2007/0077256 A1 | 4/2007 | Edwards et al. |
| 2008/0311135 A1 | 12/2008 | Zheng et al. |
| 2009/0297562 A1 | 12/2009 | Edwards et al. |
| 2010/0015182 A1 | 1/2010 | Lang et al. |
| 2010/0150942 A1 | 6/2010 | Cantor |
| 2010/0150956 A1 | 6/2010 | Patti et al. |
| 2012/0014995 A1 | 1/2012 | Edwards, Jr. et al. |
| 2012/0107316 A1 | 5/2012 | Cassone et al. |
| 2012/0237534 A1 | 9/2012 | Fu et al. |
| 2014/0037689 A1 | 2/2014 | Edwards, Jr. et al. |
| 2014/0127217 A1 | 5/2014 | Edwards, Jr. et al. |
| 2014/0127218 A1 | 5/2014 | Edwards, Jr. et al. |
| 2014/0127243 A1 | 5/2014 | Edwards, Jr. et al. |
| 2014/0335114 A1 | 11/2014 | Fu et al. |
| 2015/0191514 A1 | 7/2015 | Ibrahim et al. |
| 2015/0273031 A1* | 10/2015 | Yeaman ............. A61K 39/0002 424/185.1 |
| 2016/0220648 A1* | 8/2016 | Edwards, Jr. ...... A61K 39/0002 |

FOREIGN PATENT DOCUMENTS

| | | |
|---|---|---|
| JP | 2009-524601 A | 7/2009 |
| WO | WO-2005-049081 A1 | 6/2005 |
| WO | WO-2006/036817 A2 | 4/2006 |
| WO | WO-2006/059228 A2 | 6/2006 |
| WO | WO-2006/121895 A2 | 11/2006 |
| WO | WO-2007/081896 A2 | 7/2007 |
| WO | WO-2007/126813 A2 | 11/2007 |
| WO | WO-2010/151544 A1 | 12/2010 |
| WO | WO-2011/003085 A1 | 1/2011 |
| WO | WO-2012/163533 A1 | 12/2012 |
| WO | WO-2013/015831 A1 | 1/2013 |
| WO | WO-2014/144024 A1 | 9/2014 |
| WO | WO-2014/144211 A2 | 9/2014 |
| WO | WO-2014/144222 A2 | 9/2014 |
| WO | WO-2016/142660 A1 | 9/2016 |
| WO | WO-2017/155949 A1 | 9/2017 |

OTHER PUBLICATIONS

Examiner's Report for Canadian Patent Application No. 2,636,277, dated Dec. 4, 2012 (5 pages).
Examiner's Report for Canadian Patent Application No. 2,607,176, dated Nov. 26, 2012 (3 pages).
English Language Translation of Notice of Reasons for Rejection issued in Japanese Patent Application No. 2008-549598, dated Mar. 15, 2012, dated Mar. 21, 2012 (9 pages).
English Language Translation of Notice of Final Rejection issued in Japanese Patent Application No. 2008-549598, dated Feb. 21, 2013, dated Feb. 25, 2013 (5 pages).
First Examiner's Report issued in Australian Patent Application No. 2007205065, dated Jan. 18, 2012 (2 pages).
Patent Examination Report No. 2 issued in Australian Patent Application No. 2007205065, dated Mar. 12, 2013 (3 pages).
Ibrahim et al., "Vaccination with recombinant N-terminal domain of Als1p improves survival during murine disseminated candidiasis by enhancing cell-mediated, not humoral, immunity," Infect Immun. 73(2):999-1005 (2005).
Mamo et al., "Protection induced in mice vaccinated with recombinant collagen-binding protein (CnBP) and alpha-toxoid against intramammary infection with *Staphylococcus aureus*," Microbiol. Immunol. 44(5):381-4 (2000).
Nilsson et al., "Vaccination with recombinant fragment of collagen adhesin provides protection against *Staphylococcus aureus*-mediated septic death," J Clin Invest. 101(12):2640-9 (1998).
Patti, "Vaccines and immunotherapy for staphylococcal infections," Int J Artif Organs. 28(11):1157-62 (2005).
Sheppard et al., "Functional and structural diversity in the Als protein family of Candida albicans," J Biol Chem. 279(29):30480-9 (2004).
Bailey et al., "The Candida albicans HYR1 gene, which is activated in response to hyphal development, belongs to a gene family encoding yeast cell wall proteins," J Bacteriol. 178(18):5353-60 (1996).
Bates et al., "Candida albicans Iff11, a secreted protein required for cell wall structure and virulence," Infect Immun. 75(6):2922-8 (2007).
EBI Accession No. GSP:ATC95389. Retrieved on Nov. 19, 2012 (1 page).
EBI Accession No. GSP:AJF41554. Retrieved on Nov. 19, 2012 (1 page).
Barki et al., "Isolation of a Candida albicans DNA sequence conferring adhesion and aggregation on *Saccharomyces cerevisiae*," J Bacteriol. 175(17):5683-9 (1993).
Bendel et al., "Distinct mechanisms of epithelial adhesion for Candida albicans and Candida tropicalis. Identification of the participating ligands and development of inhibitory peptides," J Clin Invest. 92(4):1840-9 (1993).
Caesar-TonThat et al., "A monoclonal antibody to Candida albicans enhances mouse neutrophil candidacidal activity," Infect Immun. 65(12):5354-7 (1997).
Campbell, General properties and applications of monoclonal antibodies. *Monoclonal Antibody Technology*. Elsevier Science Publishers, 1-32 (1984).
Castaldo et al., "Clinical spectrum of fungal infections after orthotopic liver transplantation," Arch Surg. 126(2):149-56 (1991).
Cheng et al, "Comparison between Candida albicans agglutinin-like sequence gene expression patterns in human clinical specimens and models of vaginal candidiasis," Infect Immun. 73(3):1656-63 (2005).
Choi et al., "Acinetobacter baumannii invades epithelial cells and outer membrane protein A mediates interactions with epithelial cells," BMC Microbiol. 8:216 (2008) (11 pages).
Coleman et al., "Monoclonal antibodies specific for Candida albicans Als3 that immunolabel fungal cells in vitro and in vivo and block adhesion to host surfaces," available in PMC Jul. 1, 2010, published in final edited form as: J Microbiol Methods. 78(1):71-8 (2009) (19 pages).
Cormack et al., "An adhesion of the yeast pathogen *Candida glabrata* mediating adherence to human epithelial cells," Science. 285(5427):578-82 (1999).
Cutler et al., "Characteristics of Candida albicans adherence to mouse tissues," Infect Immun. 58(6):1902-8 (1990).
De Bernardis et al., "Protective role of antimannan and anti-aspartyl proteinase antibodies in an experimental model of Candida albicans vaginitis in rats," Infect Immun. 65(8):3399-405 (1997).
Dromer et al., "Protection of mice against experimental cryptococcosis by anti-Cryptococcus neoformans monoclonal antibody," Infect Immun. 55(3):749-52 (1987).
Ekenna et al., "Natural history of bloodstream infections in a burn patient population: the importance of candidemia," Am J Infect Control. 21(4):189-95 (1993).
Ellis, New technologies for making vaccines. *Vaccines*. Plotkin and Mortimer, 568-575 (1988).
Filler, "Candida-host cell receptor-ligand interactions," Curr Opin Microbiol. 9(4):333-9 (2006).
Fisher-Hoch et al., "Opportunistic candidiasis: an epidemic of the 1980's," Clin Infect Dis. 21(4):897-904 (1995).

(56) References Cited

OTHER PUBLICATIONS

Fonzi et al., "Isogenic strain construction and gene mapping in Candida albicans," Genetics. 134(3):717-28 (1993).
Fu et al., "Candida albicans Als1p: an adhesin that is a downstream effector of the EFG1 filamentation pathway," Mol Microbiol. 44(1):61-72 (2002).
Fu et al., "Cloning and characterization of a gene (LIP1) which encodes a lipase from the pathogenic yeast Candida albicans," Microbiology. 143(Pt 2):331-40 (1997).
Fu et al., "Cloning and characterization of CAD1/AAF1, a gene from Candida albicans that induces adherence to endothelial cells after expression in Saccharomyces cerevisiae," Infect Immun. 66(5):2078-84 (1998).
Fu et al., "Expression of the Candida albicans Gene ALS1 in Saccharomyces cerevisiae Induces Adherence to Endothelial and Epithelial Cells," Infect Immun. 66(4):1783-6 (1998).
Gale et al., "Cloning and expression of a gene encoding an integrin-like protein in Candida albicans," Proc Nat Acad Sci USA. 93(1):357-61 (1996).
Gale et al., "Linkage of adhesion, filamentous growth, and virulence in Candida albicans to a single gene, INT1," Science. 279(5355):1355-8 (1998).
Gaur et al., "Expression, cloning, and characterization of a Candida albicans gene, ALA1, that confers adherence properties upon Saccharomyces cerevisiae for extracellular matrix proteins," Infect Immun. 65(12):5289-94 (1997).
Gietz et al., "Studies on the transformation of intact yeast cells by the LiAc/SS-DNA/PEG procedure," Yeast. 11(4):355-60 (1995).
Greenspan et al., "Defining epitopes: It's not as easy as it seems," Nat Biotechnol. 17(10):936-7 (1999).
Gustafson et al., "Molecular mimicry in Candida albicans. Role of an integrin analogue in adhesion of the yeast to human endothelium," J Clin Invest. 87(6):1896-902 (1991).
Han et al., "Antibody response that protects against disseminated candidiasis," Infect Immun. 63(7):2714-9 (1995).
Hasenclever et al., "Antigenic relationships of Torulopsis glabrata and seven species of the genus Candida," J Bacteriol. 79:677-81 (1960).
Hoyer et al., "Detection of Als proteins on the cell wall of Candida albicans in murine tissues," Infect Immun. 67(8):4251-5 (1999).
Hoyer, "The ALS gene family of Candida albicans," Trends Microbiol. 9(4)176-80 (2001).
Hoyer et al., "Candida albicans ALS1: domains related to a Saccharomyces cerevisiae sexual agglutinin separated by a repeating motif," Mol Microbiol. 15(1):39-54 (1995).
Hoyer et al., "Candida albicans ALS3 and insights into the nature of the ALS gene family," Curr Genet. 33(6):451-9 (1998).
Hoyer et al., "Characterization of agglutinin-like sequence genes from non-albicans Candida and phylogenetic analysis of the ALS family," Genetics. 157(4):1555-67 (2001).
Hoyer et al., "Detection of Als proteins on the cell wall of Candida albicans in murine tissues," Infect Immun. 67(8):4251-55 (1999).
Hoyer et al., "Identification of Candida albicans ALS2 and ALS4 and localization of als proteins to the fungal cell surface," J Bacteriol. 180(20):5334-43 (1998).
Ibrahim et al., "Evidence implicating phospholipase as a virulence factor of Candida albicans," Infect Immun. 63(5):1993-8 (1995).
Ibrahim et al., "The anti-Candida vaccine based on the recombinant N-terminal domain of Als1p is broadly active against disseminated candidiasis," Infect Immun. 74(5):3039-41 (2006).
Illustrated Stedman's Medical Dictionary, 24th Edition. Williams and Wilkins, London. p. 707 (1982).
Inhibitex reports favorable results from aurexis phase II trial for the treatment of staph bloodstream infections. Inhibitex Inc. (2005) (Accessed Sep. 19, 2005) (5 pages).
Jaffe et al., "Culture of human endothelial cells derived from umbilical veins. Identification by morphologic and immunologic criteria," J Clin Invest. 52(11):2745-56 (1973).

Jarvis et al., "Predominant pathogens in hospital infections," J Antimicrob Chemother. 29 (Suppl A): 19-24 (1992) (Abstract only) (2 pages).
Jimenez-Lucho et al., "Cryptococcus neoformans, Candida albicans, and other fungi bind specifically to the glycosphingolipid lactosylceramide (Gal beta 1-4Glc beta 1-1Cer), a possible adhesion receptor for yeasts," Infect Immun. 58(7):2085-90 (1990).
Kim et al., "Partial characterization of leukocyte binding molecules on endothelial cells induced by minimally oxidized LDL," Arterioscler Thromb. 14(3):427-33 (1994).
Klein, "Role of cell surface molecules of Blastomyces dermatitidis in the pathogenesis and immunobiology of blastomycosis," Semin Respir Infect. 12(3):198-205 (1997).
Klotz et al., "Effect of an arginine-glycine-aspartic acid-containing peptide on hematogenous candidal infections in rabbits," Antimicrob Agents Chemother. 36(1):132-6 (1992).
Kramer et al., "How long do nosocomial pathogens persist on inanimate surfaces? A systematic review," BMC Infect Dis. 6:130 (2006) (8 pages).
Lipke et al., "AG alpha 1 is the structural gene for the Saccharomyces cerevisiae alpha-agglutinin, a cell surface glycoprotein involved in cell-cell interactions during mating," Mol Cell Biol. 9(8):3155-65 (1989).
Liu et al., "INH-A21 contains antibodies specific for the Candida ALS protein family," 44th ICAAC Abstracts, Oct. 30-Nov. 2, Washington D.C.. p. 425, M-1144 (2004).
Lotter et al., "Identification of an epitope on the Entamoeba histolytica 170-kD lectin conferring antibody-mediated protection against invasive amebiasis," J Exp Med. 185(10)1793-801 (1997).
Loza et al., "Functional Analysis of the Candida albicans ALS1 Gene Product," Yeast. 21(6):473-82 (2004).
Luo et al., "Neutrophils Inhibit Candidal Expression of HYR1, Which Mediates Resistance to Neutrophil Killing," 48th Annual Interscience Conference on Antimicrobial Agents and Chemotherapy / 46th Annual Meeting of ISDA. Jan. 1, Washington, DC.. vol. 48: 654. Abstract M-1583 (2008).
Luo et al., "Candida albicans Hyr1p confers resistance to neutrophil killing and is a potential vaccine target," J Infect Dis. 201(11):1718-28 (2010) (11 pages).
Luo et al.,"Active and passive immunization with rHyr1p-N protects mice against hematogenously disseminated candidiasis," PloS One. 6(10):e25909 (2011) (8 pages).
Mamo et al., "Vaccination against Staphylococcus aureus mastitis: immunological response of mice vaccinated with fibronectin-binding protein (FnBP-A) to challenge with S.aureus," Vaccine. 12(11):988-92 (1994).
Mamo et al., "Vaccination with Staphylococcus aureus fibrinogen binding proteins (FgBPs) reduces colonisation of S. aureus in a mouse mastitis model," FEMS Immonol Med Microbiol. 10(1):47-53 (1994).
Manjarrez-Hernandez et al., "Binding of diarrheagenic Escherichia coli to 32- to 33-kilodalton human intestinal brush border proteins," Infect Immun. 65(11):4494-501 (1997).
Mayer et al., "Candida albicans adherence to endothelial cells," Microvasc Res. 43(2):218-26 (1992).
Mayer et al., "Recognition of binding sites on Candida albicans by monoclonal antibodies to human leukocyte antigens," Infect Immun. 58(11):3765-9 (1990).
Mukherjee et al., "Protective murine monoclonal antibodies to Cryptococcus neoformans," Infect Immun. 60(11):4534-41 (1992).
NCBI Blast for Accession No. YP_001084998. Retrieved on Nov. 27, 2012 (2 pages).
Nilsson et al., "Vaccination with a Recombinant Fragment of Collagen Adhesin Provides Protection against Staphylococcus aureus-mediated Septic Death," J Clin Invest. 101(12):2640-9 (1998).
Oh et al., "Functional specificity of Candida albicans Als3p proteins and clade specificity of ALS3 alleles discriminated by the number of copies of the tandem repeat sequence in the central domain," Microbiology. 151(Pt 3):673-81 (2005).
Opal et al., "Systemic host responses in severe sepsis analyzed by causative microorganism and treatment effects of drotrecogin alfa (activated)," Clin Infect Dis. 37(1):50-8 (2003).

(56) References Cited

OTHER PUBLICATIONS

Palaszynski et al., "Systemic immunization with conserved pilus-associated adhesins protects against mucosal infections," Dev Biol Stand. 92:117-22 (1998).
Panaretou et al., Isolation of yeast plasma membranes. *Methods in Molecular Biology, vol. 53: Yeast Protocols*. I.H. Evans, 117-21 (1996).
Patti et al., "MSCRAMM-mediated adherence of microorganisms to host tissues," Annu Rev Microbiol. 48:585-617 (1994).
Peleg et al., "Prokaryote-eukaryote interactions identified by using Caenorhabditis elegans," Proc Natl Acad Sci USA. 105(38):14585-90 (2008).
Perraut et al., "Successful treatment of Candida albicans endophthalmitis with intravitreal amphotericin B," Arch Opthalmol. 99(9):1565-7 (1981).
Pfaller et al., "National surveillance of nosocomial blood stream infection due to species of *candida* other than *Candida albicans*: frequency of occurrence and antifungal susceptibility in the SCOPE Program. SCOPE Participant Group. Surveillance and Control of Pathogens of Epidemiologic," Diagn Microbiol Infect Dis. 30(2):121-9 (1998).
Pietrella et al., "A beta-glucan-conjugate vaccine and anti-beta-glucan antibodies are effective against murine vaginal candidiasis as assessed by a novel in vivo imaging technique," Vaccine. 28(7):1717-25 (2010).
Polak, "Combination therapy of experimental candidiasis, cryptococcosis, aspergillosis and wangiellosis in mice," Chemotherapy. 33(5):381-95 (1987).
Prasadarao et al., "Identification and characterization of S fimbria-binding sialoglycoproteins on brain microvascular endothelial cells," Infect Immun. 65(7):2852-60 (1997).
Rieg et al., "Unanticipated heterogeneity in growth rate and virulence among Candida albicans AAF1 null mutants," Infect Immun. 67(7):3193-8 (1999).
Sanford et al., "Passive immunization against Cryptococcus neoformans with an isotype-switch family of monoclonal antibodies reactive with cryptococcal polysaccharide," Infect Immun. 58(6):1919-23 (1990).
Sanger et al., "A rapid method for determining sequences in DNA by primed synthesis with DNA polymerase," J Mol Biol. 94(3):441-8 (1975).
Saporito-Irwin et al., "PHR1, a pH-regulated gene of Candida albicans, is required for morphogenesis," Mol Cell Biol. 15(2):601-13 (1995).
Schmidt et al., "NDV-3, a recombinant alum-adjuvanted vaccine for Candida and *Staphylococcus aureus* is safe and immunogenic in healthy adults," available in PMC Dec. 14, 2013, published in final edited form as: Vaccine. 30(52):7594-600 (2012) (18 pages).
Schnaar, "Isolation of glycosphingolipids," Methods Enzymol. 230:348-70 (1994).
Search Information Statement for Australian Patent Application No. 2006244401, dated Nov. 24, 2010 (3 pages).
Segal et al.,"Protection against systemic infections with various *candida* species elicited by vaccination with Candida albicans ribosomes," Sabouraudia. 23(4):275-85 (1985).
Sheth et al., "Development of an anti-adhesive vaccine for Pseudomonas aeruginosa targeting the c-terminal region of the pilin structural protein," Biomed Pept Proteins Nucleic Acids. 1(3):141-8 (1995).
Smith et al., "New insights into *Acinetobacter baumannii* pathogenesis revealed by high-density pyrosequencing and transposon mutagenesis," Genes Dev. 21(5):601-14 (2007).
Soares et al.,"2-DE analysis indicates that Acinetobacter baumannii displays a robust and versatile metabolism," Proteome Sci. 7:37 (2009) (10 pages).
Spellberg et al., "Current treatment strategies for disseminated candidiasis," Clin Infect Dis 42(2):244-51 (2006).
Spellberg et al., "Efficacy of the Anti-Candida rAls3p-N or rAls1p-N Vaccines against Disseminated and Mucosal Candidiasis," J Infect Dis 194(2):256-60 (2006).
Spellberg et al., "Parenchymal organ, and not splenic, immunity correlates with host survival during disseminated candidiasis," Infect Immun. 71(10):5756-64 (2003).
Spellberg et al., "The antifungal vaccine derived from the recombinant N terminus of Als3p protects mice against the bacterium *Staphylococcus aureus*," Infect Immun. 76(10):4574-80 (2008).
Spellberg et al., "The pathophysiology and treatment of Candida sepsis," Curr Infect Dis Rep. 4(5):387-99 (2002).
Spellberg et al., "Mice with disseminated candidiasis die of progressive sepsis," J Infect Dis. 192(2):336-43 (2005).
Stuehler et al.,"Cross-protective TH1 immunity against Aspergillus fumigatus and Candida albicans," Blood. 117(22):5881-91 (2011).
Sundstrom, "Adhesion in *candida* spp," Cell Microbiol. 4(8):461-9 (2002).
New Riverside University Dictionary, The Riverside Publishing Company, p. 933 (1984) (2 pages).
Translation of Cited Reference 3: Today's Therapy 2002, Igaku-Shoin Ltd., p. 155-156 from Japanese Application No. 2012-207831 (5 pages).
Translation of Cited Reference 2: Today's Therapy 2004, Igaku-Shoin Ltd, p. 166 from Japanese Application No. 2012-207831 (5 pages).
Torosantucci et al., "Protection by Anti-Beta-Glucan Antibodies is Associated with Restricted Beta-1,3 Glucan Binding Specificity and Inhibition of Fungal Growth and Adherence," PLoS ONE 4(4):e5392 (2009) (17 pages).
Uniprot Submission P46591. Nov. 1995. <http://www.uniprot.org/uniprotIP46591.txt?version=39> Retrieved Sep. 16, 2010 (2 pages).
Von Eiff et al., "Distribution of capsular and surface polysaccharide serotypes of *Staphylococcus aureus*," Diagn Microbiol Infect Dis. 58(3):297-302 (2007).
Wenzel et al., "*Candida* species: emerging hospital bloodstream pathogens [editoral]," Infect Control Hosp Epidermiol. 12(9):523-4 (1991).
Wey et al., "Hospital-acquired candidemia. The attributable mortality and excess length of stay," Arch Intern Med. 148(12):2642-5 (1988).
Wisplinghoff et al., "Nosocomial bloodstream infections in US hospitals: analysis of 24,179 cases from a prospective nationwide surveillance study," Clin Infect Dis. 39(3):309-17 (2004).
Wojciechowicz et al., "Cell surface anchorage and ligand-binding domains of the *Saccharomyces cerevisiae* cell adhesion protein alpha-agglutinin, a member of the immunoglobulin superfamily," Mol Cell Biol. 13(4):2554-63 (1993).
Xiong et al., "New Approaches to the Prevention and Treatment of Severe S. *aureus* Infections," Drugs Today (Barc). 36(8):529-39 (2000).
Yan et al., "Hemoglobin-induced binding of Candida albicans to the cell-binding domain of fibronectin is independent of the Arg-Gly-Asp sequence," Infect Immun. 66(5):1904-9 (1998).
Yeaman et al., "Mechanisms of NDV-3 vaccine efficacy in MRSA skin versus invasive infection," Proc Natl Acad Sci USA. 111(51):E5555-63 (2014).
Zhang et al., "Crystal Structure of Glutathione-Dependent Phospholipid Peroxidase Hyr1 from the Yeast *Saccharamyces cerevisiae*," Proteins. 73(4):1058-62 (2008).
Zhao et al., "Allelic variation in the contiguous loci encoding Candida albicans ALS5, ALS1 and ALS9," Microbiology. 149(Pt 10):2947-60 (2003).
Zhao et al., "ALS3 and ALS8 represent a single locus that encodes a Candida albicans adhesin; functional comparisons between Als3p and Als1p," Microbiology. 150(Pt 7):2415-28 (2004).
Zhao et al., "Analysis of the candida albicans Als2p and Als4p adhesins suggests the potential for compensatory function within the Als family," Microbiology. 151(Pt 5):1619-30 (2005).
Rotrosen et al., "Adherence of Candida to cultured vascular endothelial cells: mechanisms of attachment and endothelial cell penetration," J Infect Dis. 152(6):1264-74 (1985).
Santoni, "Intravaginal and intranasal immunizations confer equal protection against Candida in experimental vaginitis," Abstracts of the General Meeting of the American Society for Microbiology 101:367-8 (2001) (3 pages).

(56) References Cited

OTHER PUBLICATIONS

Examiner's First Report for Australian Patent Application No. 2006244401, dated Nov. 25, 2010 (1 page).
Patent Examination Report No. 2 for Australian Patent Application No. 2006244401, dated Aug. 21, 2012 (3 pages).
Examiner's First Report for Australian Patent Application No. 2007205065, dated Jan. 18, 2012 (2 pages).
Patent Examination Report No. 2 for Australian Patent Application No. 2007205065, dated Mar. 12, 2013 (3 pages).
Patent Examination Report No. 3 for Australian Patent Application No. 2007205065, dated Oct. 15, 2013 (3 pages).
Patent Examination Report No. 1 for Australian Patent Application No. 2013203750, dated Aug. 20, 2014 (4 pages).
Patent Examination Report No. 1 for Australian Patent Application No. 2010266114, dated Dec. 31, 2014 (3 pages).
Examiner's Report for Canadian Patent Application No. 2,636,277, dated May 13, 2014 (2 pages).
First Office Action for Chinese Patent Application No. 201080039446.5, dated May 31, 2013 (English language Translation Provided) (11 pages).
Second Office Action for Chinese Patent Application No. 201080039446.5, dated Nov. 18, 2013 (English language translation provided) (7 pages).
First Office Action for Chinese Patent Application No. 201280046321.4, dated Jan. 19, 2015 (20 pages, English language translation provided).
Second Office Action for Chinese Patent Application No. 201280046321.4, dated Oct. 26, 2015 (14 pages, English language translation provided).
Extended European Search Report for European Application No. 06752341.5, dated Nov. 13, 2009 (15 pages).
Extended European Search Report for European Patent Application No. 07709622.0, dated Nov. 19, 2009 (9 pages).
Communication pursuant to Article 94(3) EPC for European Patent Application No. 07709622.0, dated Nov. 17, 2010 (12 pages).
Communication pursuant to Article 94(3) EPC for European Patent Application No. 07709622.0, dated Mar. 3, 2010 (6 pages).
Communication pursuant to Article 94(3) EPC for European Patent Application No. 07709622.0, dated Jun. 30, 2011 (4 pages).
Communication under Rule 71(3) EPC for European Patent Application No. 07709622.0, dated Jan. 27, 2012 (8 pages).
Extended European Search Report for European Patent Application No. 10794828.3, dated Nov. 30, 2012 (9 pages).
Communication pursuant to Article 94(3) EPC for European Patent Application No. 10794828.3, dated May 19, 2014 (5 pages).
Invitation pursuant to Article 94(3) and Rule 71(1) EPC for European Patent Application No. 10794828.3, dated Sep. 21, 2015 (3 pages).
Extended European Search Report for European Patent Application No. 11008862.2, dated Feb. 10, 2012 (10 pages).
Communication pursuant to Article 94(3) EPC for European Patent Application No. 11008862.2, dated Apr. 23, 2014 (6 pages).
Summons to attend oral proceedings pursuant to Rule 115(1) EPC for European Patent Application No. 11008862.2, dated Oct. 20, 2015 (6 pages).
Extended European Search Report for European Patent Application No. 12001595.3, dated Nov. 13, 2012 (12 pages).
Communication pursuant to Article 94(3) EPC for European Patent Application No. 12001595.3, dated Apr. 23, 2014 (6 pages).
Extended European Search Report for European Patent Application No. 12001586.2, dated Nov. 13, 2012 (14 pages).
Communication pursuant to Article 94(3) EPC for European Patent Application No. 12001586.2, dated Apr. 23, 2014 (6 pages).
Summons to attend oral proceedings pursuant to Rule 115(1) EPC for European Patent Application No. 12001586.2, dated Oct. 19, 2015 (7 pages).
Extended European Search Report for European Application No. 12832321.9, dated Jun. 3, 2015 (9 pages).
Extended European Search Report for European Application No. 12817530.4, dated Dec. 18, 2014 (6 pages).
Notice of Reasons for Rejection for Japanese Patent Application No. 2008-549598, dated Mar. 21, 2012 (15 pages).
Final Japanese Office Action for Japanese Patent Application No. 2008-510281, dated Oct. 26, 2012 (3 pages).
English translation of the Final Japanese Office Action for Japanese Patent Application No. 2008-549598, dated Feb. 25, 2013 (5 pages).
Japanese Inquiry Rejection for Japanese Patent Application No. 2008-549598, dated Mar. 7, 2014 (13 pages).
Notice of Reasons for Rejection for Japanese Patent Application No. 2012-207831, dated Nov. 22, 2013 (15 pages).
Final Japanese Office Action for Japanese Patent Application No. 2012-207831, dated Dec. 16, 2014 (10 pages).
Japanese Office Action for Japanese Patent Application No. 2014-105980, dated Apr. 24, 2015 (2 pages).
Notification of Reason for Rejection for Japanese Patent Application No. 2014-105980, dated Jan. 29, 2016 (English language translation provided, 13 pages).
Examination Report for New Zealand Patent Application No. 597442, dated Jul. 18, 2012 (2 pages).
Office Action for Russian Patent Application No. 2012103502, dated Oct. 14, 2014 (English language translation provided) (5 pages).
Office Action for Russian Patent Application No. 2012103502, dated May 21, 2014 (English translation provided) (6 pages).
Office Action for Ukrainian Patent Application No. a 2013 10981, dated Nov. 13, 2015 (English translation provided) (6 pages).
Office Action for Georgian Patent Application No. 13226/01, dated Feb. 9, 2015 (2 pages, English language translation provided).
International Search Report for International Application No. PCT/US2006/017482, dated Mar. 19, 2007 (2 pages).
Written Opinion of the International Searching Authority for International Application No. PCT/US2006/017482, dated Mar. 19, 2007 (3 pages).
International Preliminary Report on Patentability for International Application No. PCT/US2006/017482, dated Nov. 6, 2007 (4 pages).
International Search Report for International Patent Application No. PCT/US2007/000433, dated Oct. 1, 2007 (1 page).
Written Opinion of the International Searching Authority for International Application No. PCT/US2007/000433, dated Oct. 1, 2007 (4 pages).
International Preliminary Report on Patentability for International Application No. PCT/US2007/000433, dated Jul. 8, 2008 (5 pages).
International Search Report for International Patent Application No. PCT/US12/55604, dated Mar. 8, 2013 (9 pages).
Written Opinion of the International Searching Authority for International Patent Application No. PCT/US12/55604, dated Mar. 8, 2013 (10 pages).
International Preliminary Report on Patentability for International Patent Application No. PCT/US12/55604, dated Mar. 18, 2014 (11 pages).
International Search Report of International Application No. PCT/US12/00328, dated Dec. 18, 2012 (3 pages).
International Preliminary Report on Patentability for International Application No. PCT/US12/00328, dated Jan. 28, 2014 (6 pages).
Written Opinion of the International Searching Authority for International Application No. PCT/US12/00328, dated Dec. 18, 2012 (5 pages).
International Search Report for International Application No. PCT/US2010/040949, dated Jun. 6, 2011 (3 pages).
Written Opinion of the International Searching Authority for International Application No. PCT/US2010/040949, dated Jun. 6, 2011 (4 pages).
International Preliminary Report on Patentability for International Application No. PCT/US2010/040949, dated Jan. 4, 2012 (5 pages).
Liang et al., "Prediction of antigenic epitopes on protein surfaces by consensus scoring," BMC Bioinformatics 10:302 (2009) (10 pages).
GenBank for Accession No. AAO72958.1. Retrieved on Jan. 6, 2016 (2 pages).
International Search Report for International Patent Application No. PCT/US2014/28535, dated Oct. 24, 2014 (5 pages).
Written Opinion of the International Searching Authority for International Patent Application No. PCT/US14/28535, dated Oct. 24, 2014 (6 pages).

(56) References Cited

OTHER PUBLICATIONS

International Preliminary Report on Patentability for International Patent Application No. PCT/US2014/028535, dated Sep. 15, 2015 (7 pages).
International Search Report for International Patent Application No. PCT/US14/28521, dated Nov. 13, 2014 (7 pages).
Written Opinion of the International Searching Authority for International Patent Application No. PCT/US14/28521, dated Nov. 13, 2014 (10 pages).
International Preliminary Report on Patentability for International Patent Application No. PCT/US2014/028521, dated Oct. 13, 2015 (11 pages).
International Search Report for International Patent Application No. PCT/US14/28256, dated Aug. 18, 2014 (4 pages).
Written Opinion of the International Searching Authority for International Patent Application No. PCT/US14/28256, dated Aug. 18, 2014 (6 pages).
International Preliminary Report on Patentability for International Patent Application No. PCT/US2014/028256, dated Sep. 15, 2015 (7 pages).
International Search Report and Written Opinion for International Patent Applciation No. PCT/US14/28521, dated Nov. 13, 2014 (24 pages).
Notice of Reasons for Rejection for Japanese Patent Application No. 2015-018131, dated Mar. 16, 2016 (9 pages) (English language translation provided).
Lin et al., "Acinetobacter baumannii rOmpA vaccine dose alters immune polarization and immunodominant epitopes," available in PMC Jan. 2, 2014, published in final edited form as: Vaccine 31(2):313-8 (2013) (14 pages).
First Office Action for Chinese Patent Application No. 201280056018.2, dated Mar. 14, 2016 (English language translation provided) (27 pages).
Harlow et al., Monoclonal Antibodies. *Antibodies: A Laboratory Manual*. Cold Spring Harbor Laboratory, 139-172 (1988).
Non-Final Office Action for U.S. Appl. No. 11/327,197, dated Aug. 31, 2016 (24 pages).
Skolnick et al., "From genes to protein structure and function: novel applications of computational approaches in the genomic era," Trends Biotechnol. 18(1):34-9 (2000).
Zhao et al., "Candida albicans Als3p is required for wild-type biofilm formation on silicone elastomer surfaces," Microbiology 152(Pt 8):2287-2299 (2006) (25 pages).
David et al., "Community-Associated Methicillin-Resistant *Staphylococcus aureus*: Epidemiology and Clinical Consequences of an Emerging Epidemic," Clin Microbiol Rev. 23(3):616-687 (2010).
International Search Report for International Application No. PCT/US2018/026889, dated Jul. 11, 2018 (4 pages).
Written Opinion of the International Searching Authority for International Application No. PCT/US2018/026889, dated Jul. 11, 2018 (13 pages).
Chowdhary et al., "*Candida auris*: A rapidly emerging cause of hospital-acquired multidrug-resistant fungal infections globally," PLoS Pathog. 13(5):e1006290 (2017) (10 pages).
Kaur et al., "Strategies to reduce mortality in adult and neonatal Candidemia in developing countries," J Fungi (Basel). 3(3):pii:E41 (2017) (20 pages).
Sherry et al., "Biofilm-forming capability of highly virulent, multidrug-resistant *Candida auris*," Emerg Infect Dis. 23(2):328-331 (2017).
Extended European Search Report for European Patent Application No. 18166876.5, dated Jul. 31, 2018 (10 pages).
Larkin et al., "The Emerging Pathogen *Candida auris*: Growth Phenotype, Virulence Factors, Activity of Antifungals, and Effect of SCY-078, a Novel Glucan Synthesis Inhibitor, on Growth Morphology and Biofilm Formation," Antimicrob Agents Chemother. 61(5). pii: e02396-16 (2017).
Sui et al., "The vaccines and antibodies associated with Als3p for treatment of Candida albicans infections," Vaccine 35(43):5786-5793 (2017).
Tsay et al., "Approach to the Investigation and Management of Patients With *Candida auris*, an Emerging Multidrug-Resistant Yeast," Clin Infect Dis. 66(2):306-311 (2018).
First Examination Report for Indian Patent Application No. 1302/DELNP/2014, dated Sep. 26, 2018 (7 pages).

\* cited by examiner

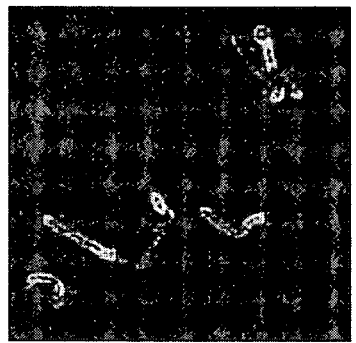 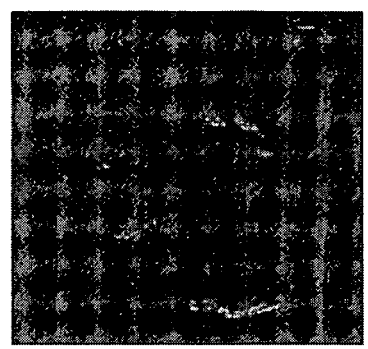
FIG. 2A    FIG. 2B
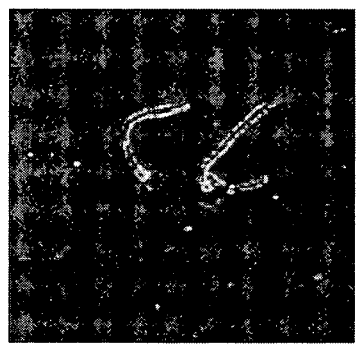 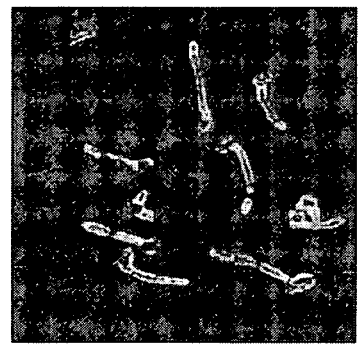
FIG. 2C    FIG. 2D

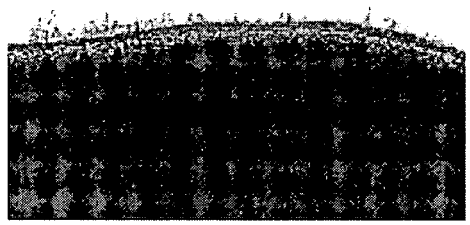 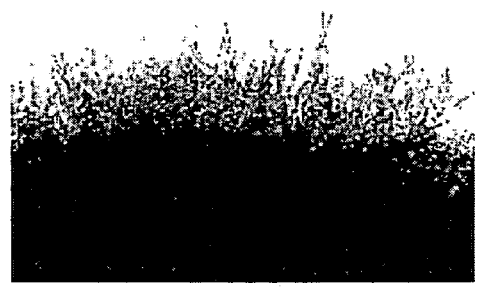
FIG. 3B

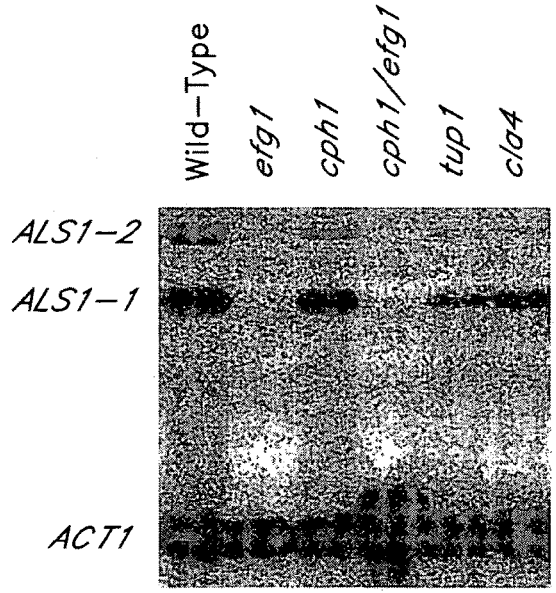
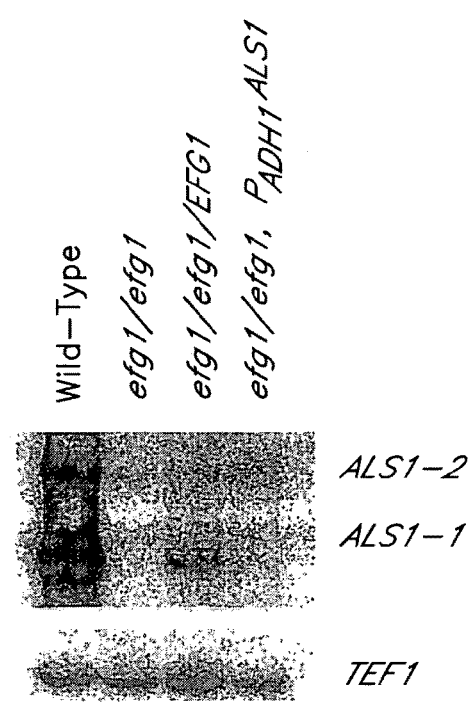
FIG. 4A  FIG. 4B

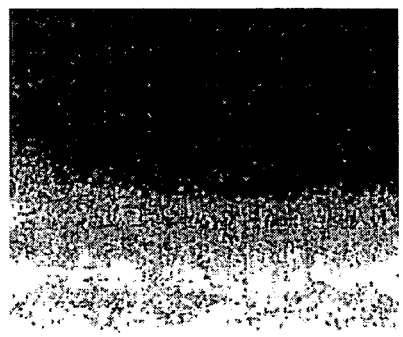
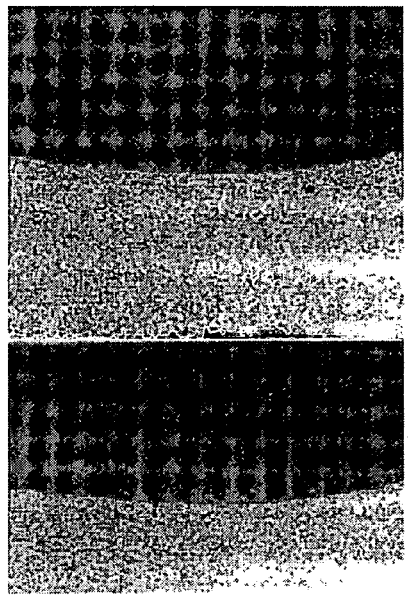
FIG. 4C

FIG. 7

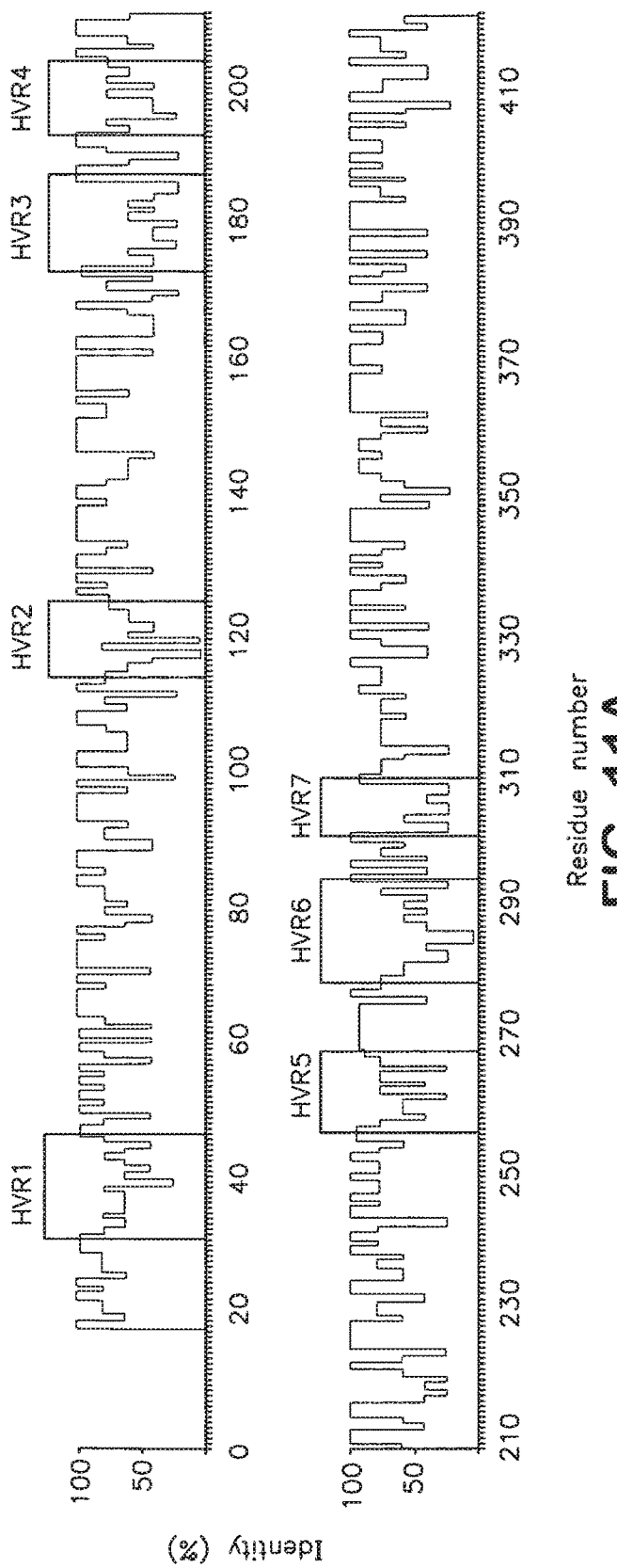
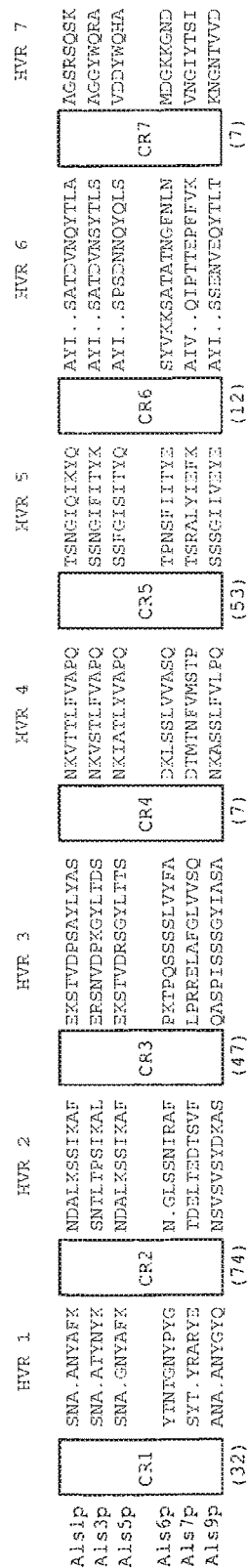
FIG. 11A
FIG. 11B

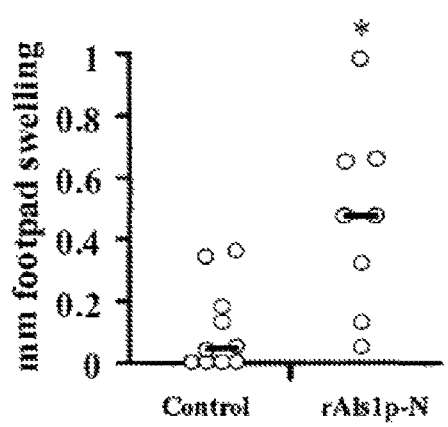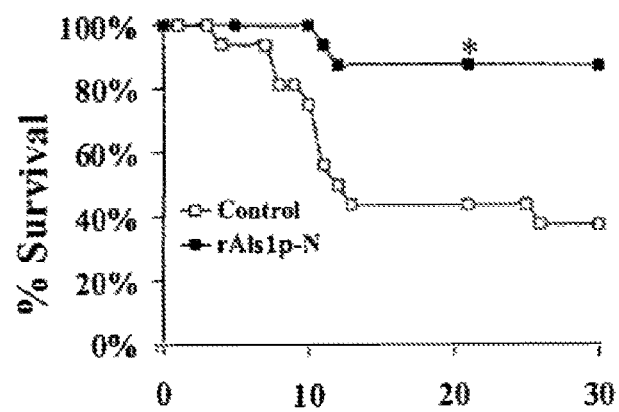
Fig. 23A                    Fig. 23B

CD1

Days Post Infection

PHARMACEUTICAL COMPOSITIONS AND METHODS TO VACCINATE AGAINST DISSEMINATED CANDIDIASIS AND OTHER INFECTIOUS AGENTS

This invention was made with government support under Public Health Service grants PO-1AI-37194, RO1Ai-19990, and MO1 RR0425. The United States Government has certain rights in this invention

BACKGROUND OF THE INVENTION

This invention relates to *Candida albicans* surface adhesin proteins, to antibodies resulting from an immune response to vaccination with *C. albicans* surface adhesion proteins and to methods for the prevention and/or treatment of candidiasis and other bacterial infections with *C. albicans* surface adhesion proteins.

There has been a dramatic increase in the incidence of nosocomial infections caused by *Candida* species in recent years. The incidence of hematogenously disseminated candidal infections increased 11-fold from 1980 to 1989. This increasing incidence has continued into the 1990s. Infections by *Candida* species are now the fourth most common cause of nosocomial septicemia, are equal to that of *Escherichia coli*, and surpass the incidence caused by *Klebsiella* species. Furthermore *Candida* species are the most common cause of deep-seated fungal infections in patients who have extensive burns. Up to 11% of individuals undergoing bone marrow transplantation and 13% of those having an orthotopic liver transplant will develop an invasive candidal infection.

*Candida albicans*, the major pathogen in this genus, can switch between two morphologies: the blastospore (budding yeast) and filamentous (hyphae and pseudohyphae) phases. *Candida* mutants that are defective in genes regulating filamentation are reported to have reduced virulence in animal models. This reduced virulence suggests that the ability to change from a blastospore to a filament is a key virulence factor of *C. albicans*. To date, no essential effectors of these filamentation pathways have been identified in *C. albicans*. See Caesar-TonThat, T. C. and J. E. Cutler, "A monoclonal antibody to *Candida albicans* enhances mouse neutrophil candidacidal activity," Infect. Immun. 65:5354-5357, 1997.

*Staphylococcus aureus* infections also are common and increasingly result in drug resistance to antibiotics. For example, *S. aureus* is a common cause of skin and skin structure infections, endocarditis and bacteremia in the U.S. and throughout the world. Formerly community acquired *S. aureus* (CA-*S. aureus*) infections were nearly uniformly susceptible to penicillinase-resistant beta lactams such as cefazolin, oxacillin, methicillin, penicillin and amoxicillin. However, over the past decade, epidemics of beta-lactam resistant *S. aureus* (MRSA) infection have been seen in multiple locales throughout the world, especially community acquired MRSA (CA-MRSA). In many places MRSA has become the predominant *S. aureus* strain causing CA infections. A recent, prospective, population-based survey in three states in the U.S. estimated that the incidence of CA-MRSA infections is 500 cases per 100,000 population, which translates to approximately 1.5 million cases per year in the U.S. alone. The increasing frequency of drug-resistant *S. aureus* infections highlights the need for new ways to prevent and treat these infections.

The identification of effectors in the regulatory pathways of the organism that contribute to virulence offers the opportunity for therapeutic intervention with methods or compositions that are superior to existing antifungal agents. The identification of cell surface proteins that affect a regulatory pathway involved in virulence is particularly promising because characterization of the protein enable immunotherapeutic techniques that are superior to existing antifungal agents when fighting a candidal infection.

The virulence of *Candida albicans* is regulated by several putative virulence factors of which adherence to host constituents and the ability to transform from yeast-to-hyphae are among the most critical in determining pathogenicity. While potent antifungal agents exist that are microbicidal for *Candida*, the attributable mortality of candidemia is approximately 38%, even with treatment with potent antifungal agents such as amphotericin B. Also, existing agents such as amphotericin B tend to exhibit undesirable toxicity. Although additional antifungals may be developed that are less toxic than amphotericin B, it is unlikely that agents will be developed that are more potent. Therefore, either passive or active immunotherapy to treat or prevent disseminated candidiasis is a promising alternative to standard antifungal therapy.

Thus, there exists a need for effective immunogens that will provide host immune protection and passive immunoprotection against *Candida*, *S. aureus* and other immunogenically related pathogens. The present invention satisfies this need and provides related advantages as well.

SUMMARY OF THE INVENTION

The invention provides a vaccine including an isolated Als protein family member having cell adhesion activity, or an immunogenic fragment thereof, with an adjuvant in a pharmaceutically acceptable medium. The invention also provides a method of treating or preventing disseminated candidiasis. The method includes administering an immunogenic amount of a vaccine an isolated Als protein family member having cell adhesion activity, or an immunogenic fragment thereof, in a pharmaceutically acceptable medium. A method of treating or preventing disseminated candidiasis also is provided that includes administering an effective amount of an isolated Als protein family member having cell adhesion activity, or an functional fragment thereof, to inhibit the binding or invasion of *Candida* to a host cell or tissue. The Als protein family member can be derived from a *Candida* strain selected from the group consisting of *Candida albicans, Candida krusei, Candida tropicalis, Candida glabrata* and *Candida parapsilosis* and the Als protein family member includes Als1p, Als3p, Als5p, Als6p, Als7p or Als9p. Also provided is a method of treating or preventing *Staphylococcus aureus* infections. The method includes administering an immunogenic amount of a vaccine an isolated Als protein family member having cell adhesion activity, or an immunogenic fragment thereof, in a pharmaceutically acceptable medium.

BRIEF DESCRIPTION OF THE DRAWINGS

FIG. 2A-D shows the cell surface localization of Als1p on filaments of *C. albicans* indirect immunofluorescence. Filamentation of *C. albicans* was induced by incubating yeast cells in RPMI 1640 medium with glutamine for 1.5 hours at 37° C. Als1p was detected by incubating organisms first with anti-Als1p mouse mAb followed by FITC-labeled goat anti-mouse IgG. *C. albicans* cell surface was also stained with anti-*C. albicans* polyclonal Ab conjugated with ALEXA FLUOR® 594 (Molecular Probes, Eugene, Oreg.). Areas with yellow staining represent Als1p localization. (A) *C. albicans* wild-type. (B) als1/als1 mutant strain. (C) als1/als1 complemented with wild type ALS1 (D) $P_{ADH1}$-ALS1 overexpression mutant.

FIGS. 3A-3B show the mediation of Als1p on *C. albicans* filamentation on solid medium. *C. albicans* blastospores were spotted on Lee's agar plates and incubated at 37° C. for 4 days (A) or 3 days (B).

FIGS. 4A-4C show the control of ALS1 expression and the mediation of *C. albicans* filamentation by the EFG1 filamentation regulatory pathway. (A) Northern blot analysis showing expression of ALS1 in (i) mutants deficient in different filamentation regulatory pathways. (ii) efg1/efg1 mutant complemented with either EFG1 or $P_{ADH1}$-ALS1. Total RNA was extracted from cells grown in RPMI 1640+glutamine medium at 37° C. for 90 minutes to induce filamentation. Blots were probed with ALS1 and TEF1. (B) Photomicrographs of the efg1/efg1 mutant and efg1/efg1 mutant complemented with $P_{ADH1}$-ALS1 grown on Lee's agar plates at 37° C. for 4 days.

FIG. 7 is polypeptide sequence alignment of the N-terminal portion of select ALS polypeptides arranged by adherence phenotype. The top three lines are the sequences from ALS1, 3 and 5 polypeptides (SEQ ID NOS: 1-3, respectively), which bind endothelial cells. The bottom three are sequences from ALS6, 7 and 9 polypeptides (SEQ ID NOS: 4-6, respectively), which do not bind endothelial cells. The last line represents the ALS polypeptide family consensus sequence (SEQ ID NO:7).

FIGS. 11A and 11B are schematics showing an alignment of the N-terminal amino acid sequence of Als proteins of known function demonstrates an alternating pattern of CRs and HVRs. FIG. 11A, percentage of consensus identity among the N-terminal regions of Als proteins of known function. Note that the signal peptide region (amino acids 1-20) is not shown. Open boxes indicate the regions designated as HVRs 1-7. FIG. 11B, schematic alignment of Als proteins showing the composition of the individual HVRs. The sequences are arranged to compare proteins with an affinity to multiple substrates with those that bind few or no identified substrates. The number of amino acids in each conserved region is indicated in parentheses. The sequences of HVRs1-7 of Als1p, Als3p, Als5p, Als6p, Als7p, and Als9p correspond to the following sequences from SEQ ID NOs: 1-6, respectively:

|  | HVR1 | HVR2 | HVR3 | HVR4 | HVR5 | HVR6 | HVR7 |
|---|---|---|---|---|---|---|---|
| Als1p (SEQ ID NO: 1) | 33-41 | 115-125 | 174-187 | 194-204 | 257-266 | 278-291 | 299-306 |
| Als3p (SEQ ID NO: 2) | 33-41 | 115-125 | 174-187 | 194-204 | 257-266 | 278-291 | 299-306 |
| Als5p (SEQ ID NO: 3) | 33-41 | 115-125 | 174-187 | 194-204 | 257-266 | 278-291 | 299-306 |

-continued

|  | HVR1 | HVR2 | HVR3 | HVR4 | HVR5 | HVR6 | HVR7 |
| --- | --- | --- | --- | --- | --- | --- | --- |
| Als6p (SEQ ID NO: 4) | 33-42 | 117-126 | 175-188 | 195-205 | 258-267 | 279-294 | 302-309 |
| Als7p (SEQ ID NO: 5) | 34-42 | 116-126 | 175-188 | 195-205 | 258-267 | 279-292 | 300-307 |
| Als9p (SEQ ID NO: 6) | 33-41 | 115-125 | 174-187 | 194-204 | 256-265 | 277-290 | 298-305 |

Figure 12:
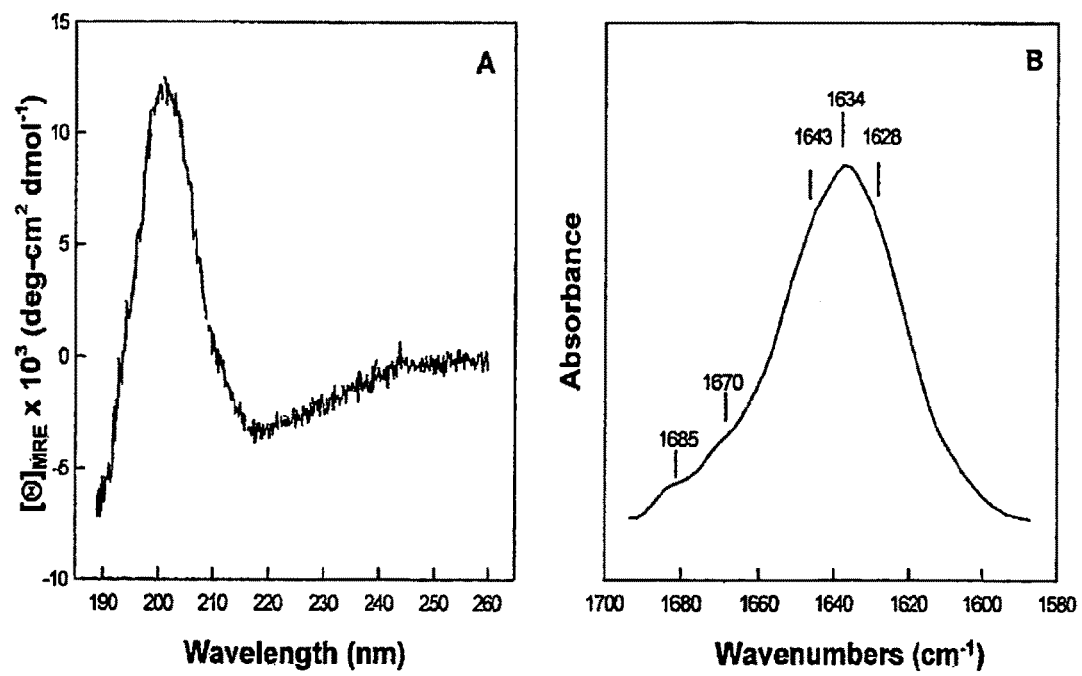

FIG. 12 shows CD and FTIR spectra of the Als1 protein N-terminal domain. A, circular dichroism spectrum of 10 µM Als1p in phosphate-buffered saline. B, FTIR spectrum of Als1p self-film hydrated with $D_2O$ vapor.

Figure 13:
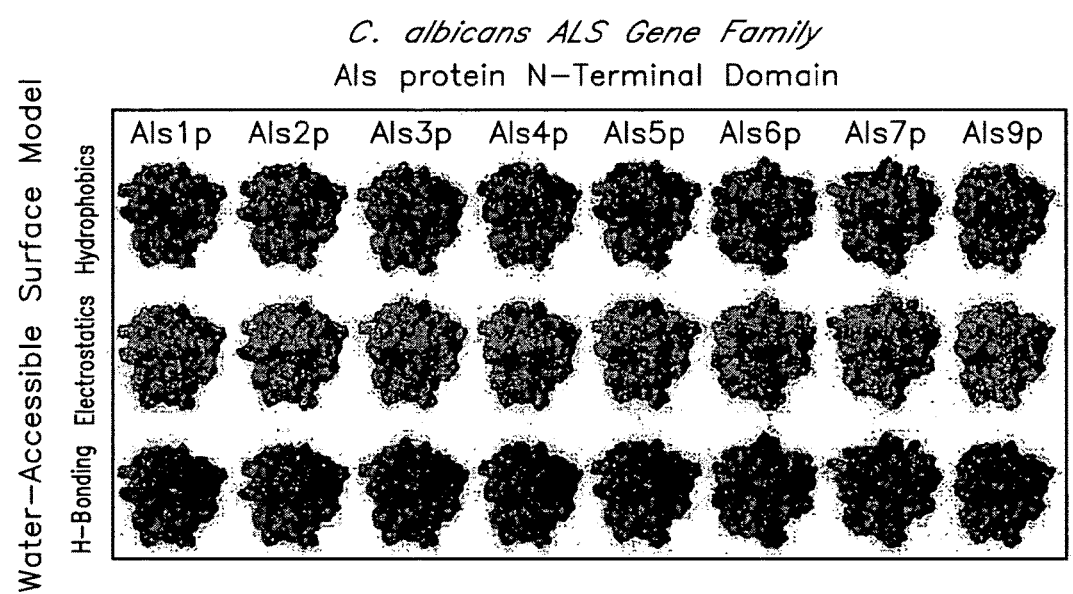

FIG. 13 shows a comparison of predicted physicochemical properties of N-terminal domains among the Als protein family. Hydrophobic, electrostatic, or hydrogen-bonding features are projected onto water-accessible surfaces of each domain. Hydrophobics are shown as follows: brown, most hydrophobic; blue, most hydrophilic. Electrostatics (spectral continuum) is shown as follows: red, most positive charge (+10 kcal/mol); blue, most negative charge (−10 kcal/mol). Hydrogen-bonding potential (H-binding) is shown as follows: red, donor; blue, acceptor. Als proteins are distinguishable into three groups based on the composite of these properties. For example, note the similar hydrophobic, electrostatic, and hydrogen-bonding profiles among Als group A proteins, Als1p, Als3p, and Als5p. In contrast, Als group B members, Als6p and Als7p, display striking differences in hydrophobic and electrostatic features from those of Als group A. In addition to biochemical profiles, note the differences in predicted structure among these domains.

Figure 14:
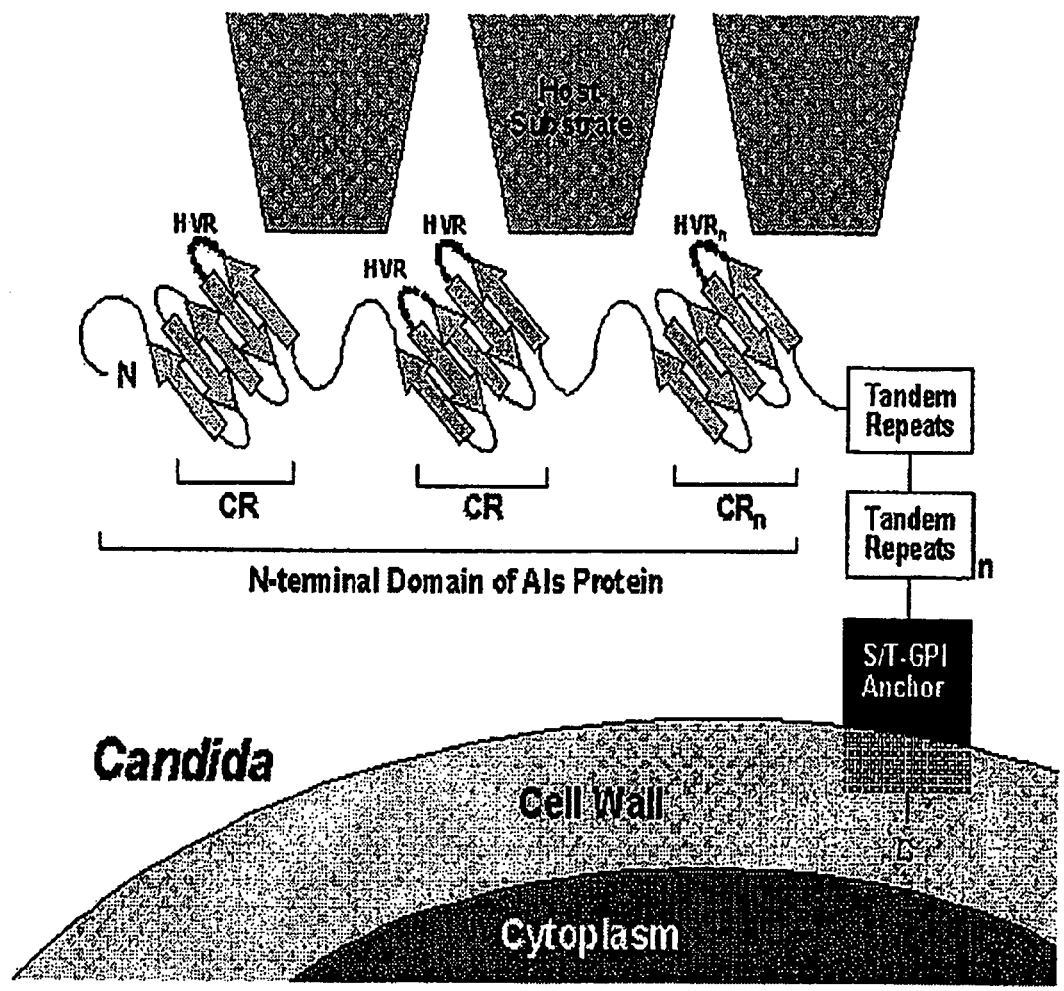

FIG. 14. Conceptual model of structural-functional relationships in Als family proteins. Als proteins are composed of three general components: an N-terminal domain, tandem repeats, and a serine/threonine-rich C-terminal domain containing a glycosylphosphatidylinositol anchor that interfaces with the C. albicans cell wall. As illustrated, Als proteins contain multiple conserved anti-parallel β-sheet regions (CR1-n) that are interposed by extended spans, characteristic of the immunoglobulin superfamily. Projecting from the β-sheet domains are loop/coil structures containing the HVRs. The three-dimensional physicochemical properties of specific Als protein HVRs probably govern interactions with host substrates that confer adhesive and invasive functions to Candida. For illustrative purposes, only three N-terminal β-sheet/coil domains and their respective CR/HVR components are shown. Note that this projection is viewed at right angles to the structural images shown in FIG. 13.

Figure 15:
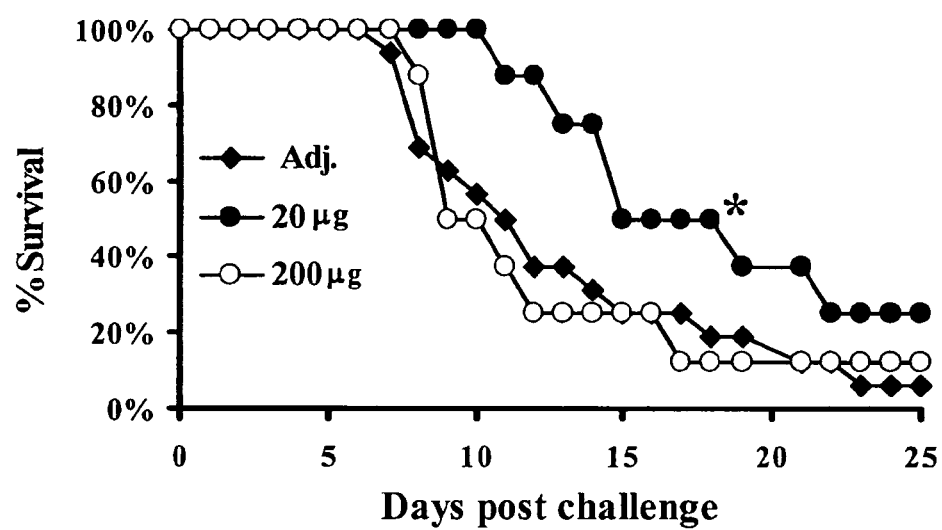

FIG. 15. Immunization of mice (retired breeders) with rAls1p-N improves survival during subsequent disseminated candidiasis. Survival of mice immunized with Als1p plus adjuvant. N=16 mice per group in duplicate experiments on different days; Adj.=adjuvant. *p<0.05 vs adjuvant.

Figure 16A:
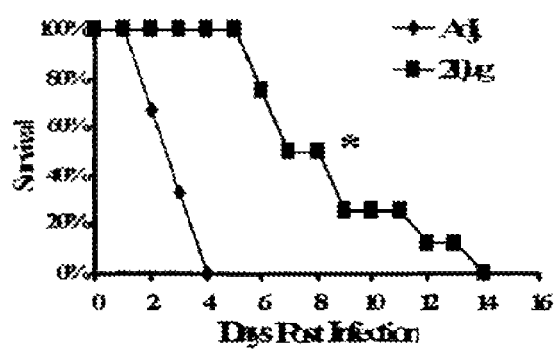
Figure 16B:
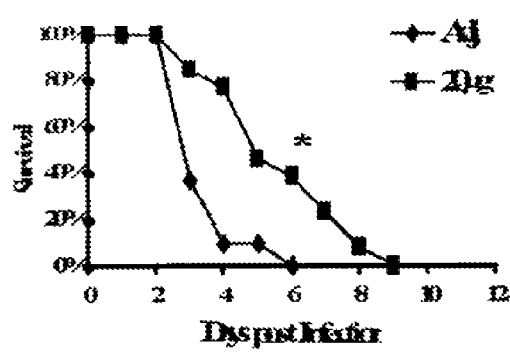

FIGS. 16A-16B show immunization with rAls1p-N improves the survival of both retired breeder and juvenile mice. Survival of retired breeder (A) and juvenile (B) mice infected with a rapidly fatal, $10^6$ inoculum of C. albicans. N=16 mice per group in duplicate experiments on different days; Adj.=adjuvant. *p<0.05 vs adjuvant control.

Figure 17:
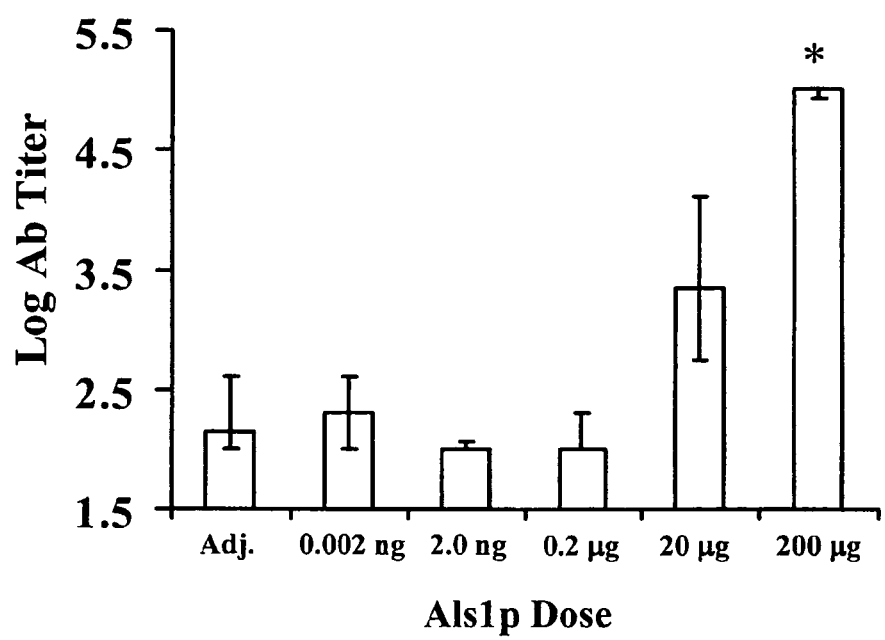

FIG. 17. Anti-rAls1 p-N titers do not correlate with survival. Titers of anti-rAls1p-N polyclonal antibodies raised in Balb/c mice immunized with varying doses of rAls1p-N with or without adjuvant. Adj.=adjuvant. *p≤0.005 for 200 µg vs. all others.

Figure 18:
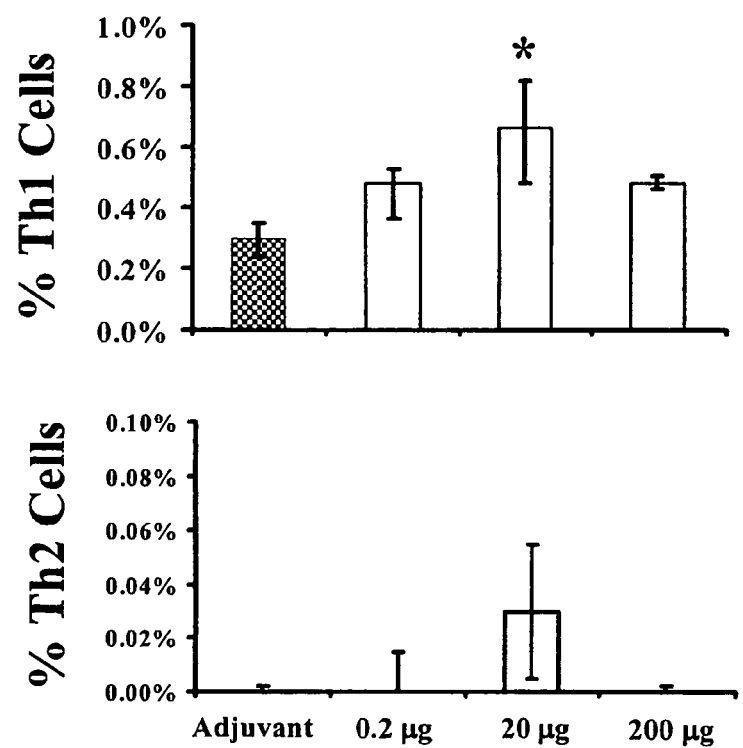

FIG. 18. Only the protective dose of rAls1p-N induces an increase in C. albicans-stimulated Th1 splenocytes. Induction of Th1 ($CD4^+IFN-\gamma^+IL-4^-$) and Th2 ($CD4^+IFN-\gamma^-IL-4^+$) splenocytes by different doses of the rAls1p-N vaccine. Splenocytes from immunized mice (n=9 per group) were stimulated for 48 h with heat-killed pre-germinated C. albicans and then analyzed by 3-color flow cytometry. *p=0.03 vs. adjuvant.

Figure 19:
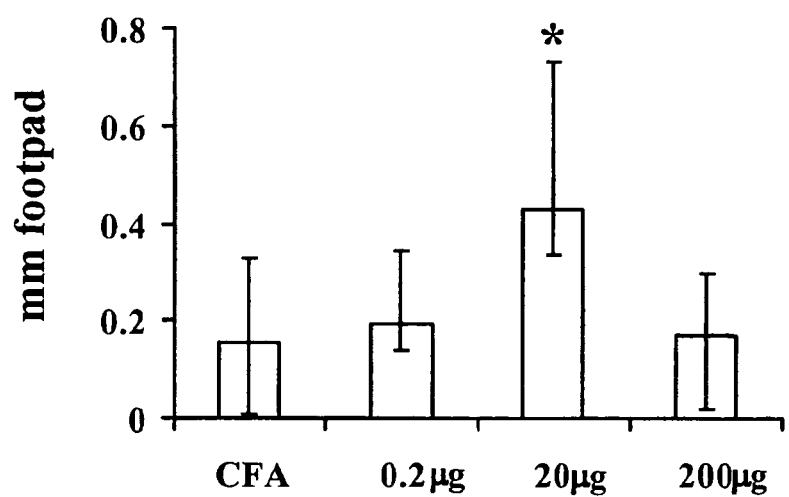

FIG. 19. Only the protective dose of rAls1p-N induces an increase in rAls1p-N-stimulated delayed type hypersensitivity. Delayed type hypersensitivity, assessed by footpad swelling, in mice (n=9-12 per group) vaccinated with rAls1p-N or CFA alone. Mice were immunized with the indicated amount of rAls1p-N and then injected with 50 µg of rAls1p-N into the footpad. Footpad swelling was assessed 24 h later. *p<0.05 versus adjuvant, 0.2 µg, and 200 µg.

Figure 20:
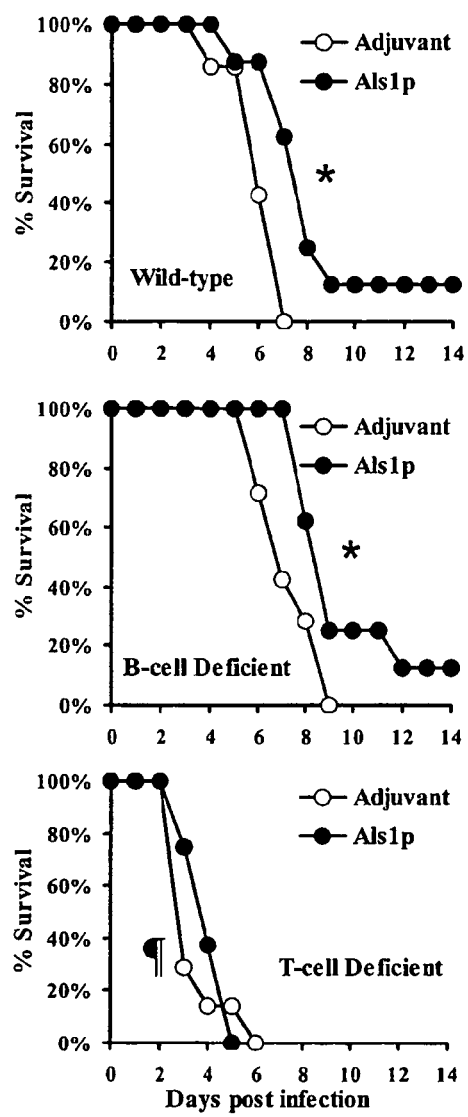

FIG. 20. The rAls1p-N vaccine requires T cells, but not B cells, to induce protective immunity. Survival of B cell-deficient, T cell-deficient (nude), and congenic wild-type Balb/c control mice (n=7 or 8 per group) was simultaneously assessed after vaccination with rAls1p-N+adjuvant or adjuvant alone. *p<0.04 versus adjuvant alone, *p=0.003 versus wild-type adjuvant-treated.

Figure 21:
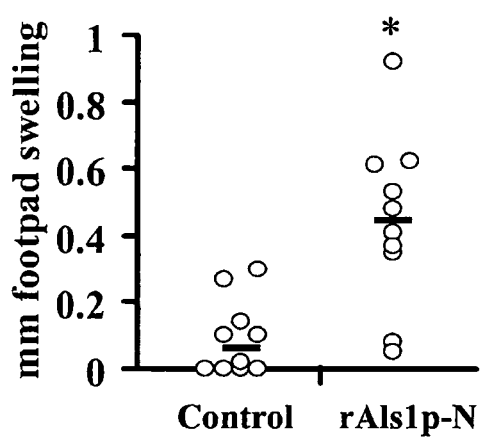

FIG. 21. SQ vaccination with rAls1p-N induces an in vivo DTH response in immunocompetent mice. Footpad swelling was assessed 24 h after injection of 50 µg of rAls1p-N into the footpad in BALB/c mice (n=10 per group). Median values are displayed as black bars. *p=0.002 vs. control by Wilcoxon Rank Sum test.

Figure 22A:
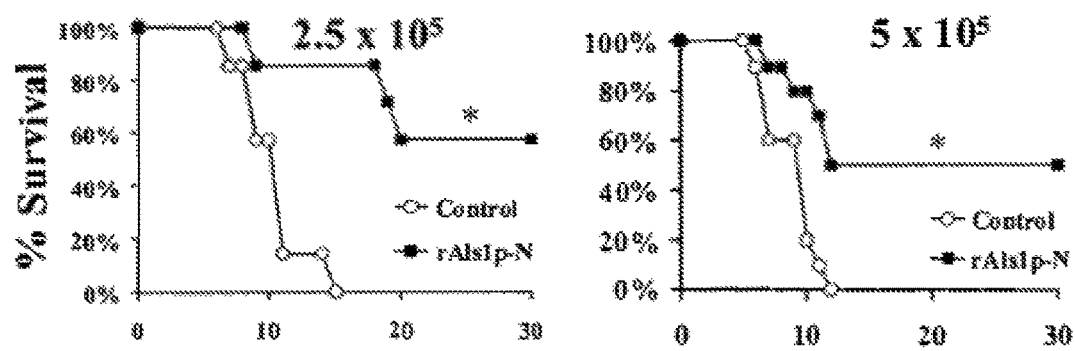
Figure 22B:
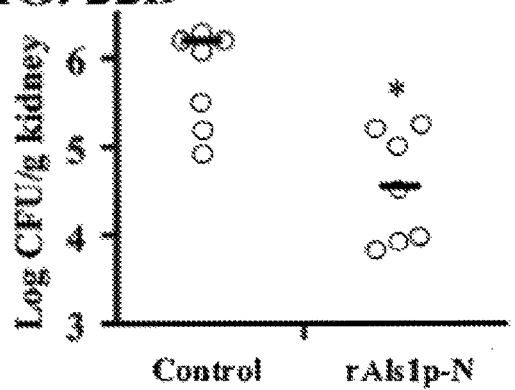

FIGS. 22A-22B show the rAls1p-N vaccine improves survival of immunocompetent mice with hematogenously disseminated candidiasis and reduces tissue fungal burden. A) Survival of vaccinated or control BALB/c mice (n=7 or 10 per group for 2.5 or $5\times10^5$ inocula, respectively) mice subsequently infected via the tail-vein with C. albicans. Each experiment was terminated at 30 days post-infection with all remaining mice appearing well. *p<0.05 vs. Control by Log Rank test. B) Kidney fungal burden in BALB/c mice (n=7 per group) infected via the tail vein with $5\times10^5$ blastospores of C. albicans. The y axis reflects the lower limit of detection of the assay. Median values are displayed as black bars. *p=0.01 vs control by Wilxocon Rank Sum test.

FIGS. 23A-23B show the rAls1p-N vaccine induces a DTH reaction in neutropenic mice and improves their survival during subsequent hematogenously disseminated candidiasis. A) Footpad swelling was assessed 24 h after injection of 50 µg of rAls1p-N into the footpad in BALB/c mice (n=10 for Control, n=8 for rAls1p-N). *p=0.006 vs Control by Wilcoxon Rank Sum test. B) Survival of neutropenic BALB/c mice (n=16 per group from 2 experiments) infected with $2.5\times10^4$ blastospores of C. albicans. *p=0.007 vs adjuvant control by Log Rank test.

Figure 24:
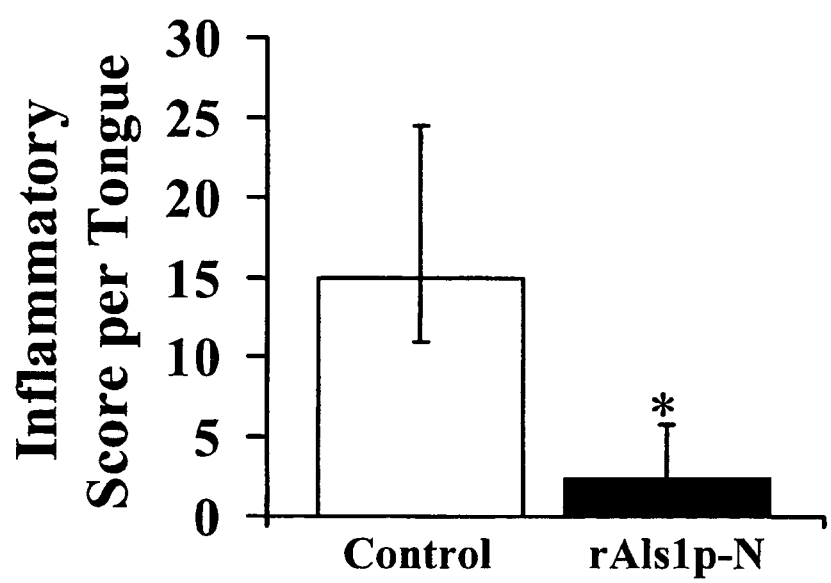

FIG. 24. The rAls1p-N vaccine diminishes the severity of histopathological fungal lesions on the tongues of mice with oropharyngeal candidiasis. N=4 mice per group. Inflammatory score generated by a blinded observer as described in the text. *p=0.03 by Wilcoxon Rank Sum test.

Figure 25:
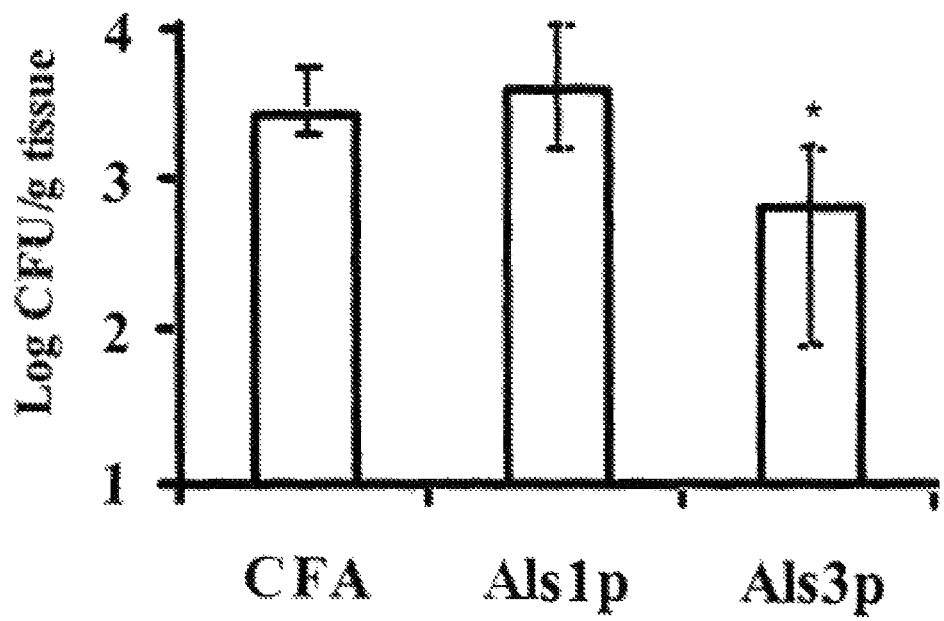

FIG. 25 shows that rAls3p-N but not rAls1p-N vaccine diminishes fungal colonization of vagina of mice inoculated with *C. albicans* (*p=0.01 vs mice vaccinated with CFA alone, by Wilcoxon Rank Sum test) N=11 mice per group.

Figure 26:
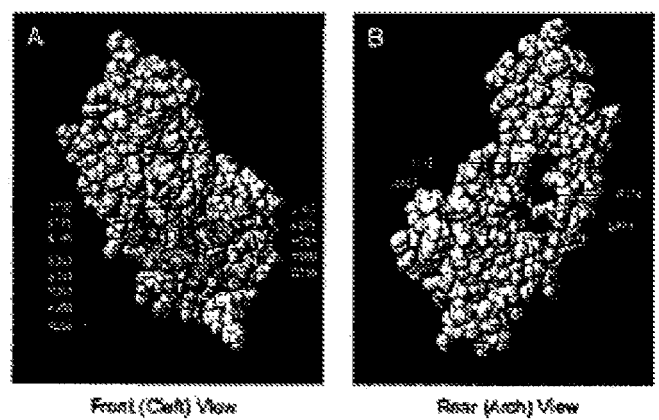

FIG. 26 shows an Als1p homology map versus *S. aureus* clumping factor A (cln67A). Consensus functional sites from *C. albicans* Als1p and *S. aureus* ClfA were mapped onto the Als1p homology model. Numerous residues from the N-termini of Als1p and ClfA map to a consensus cleft motif, which is where binding to substrate is predicted to occur for both adhesins.

Figure 27:
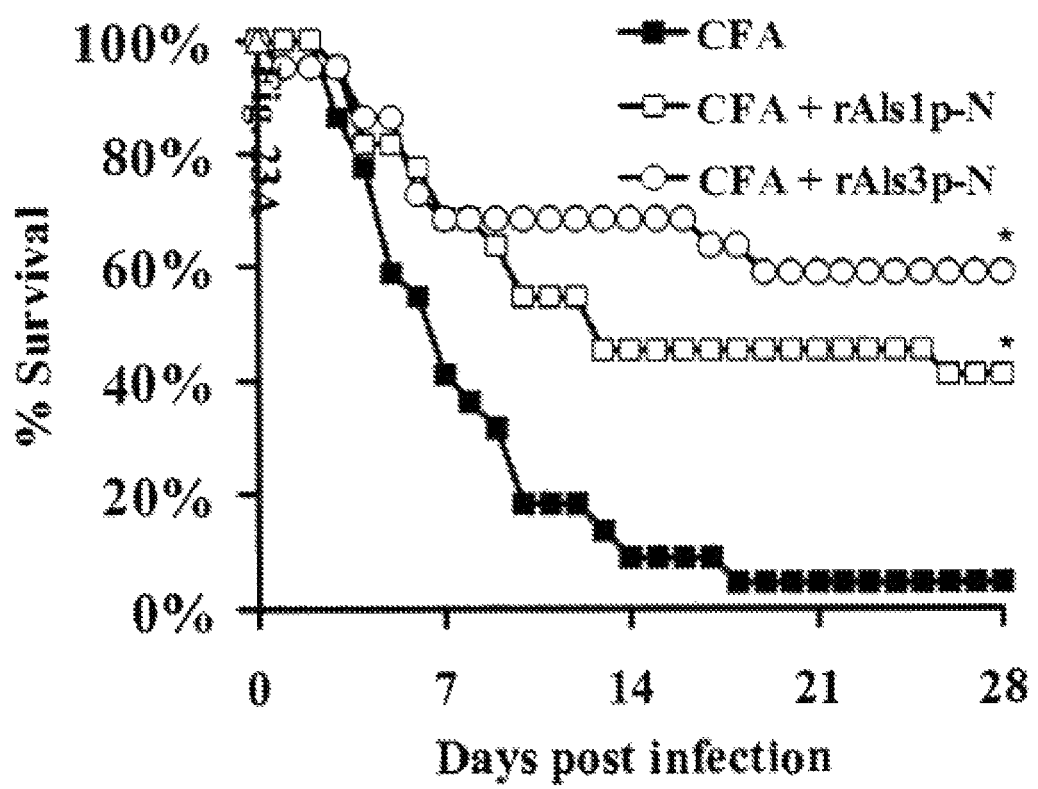

FIG. 27 shows that rAls1p-N and rAls3p-N vaccines improve the survival of staphylococcemic mice. (*p<0.003 vs mice vaccinated with CFA alone, by Log Rank test). N=22 mice per group.

Figure 28:
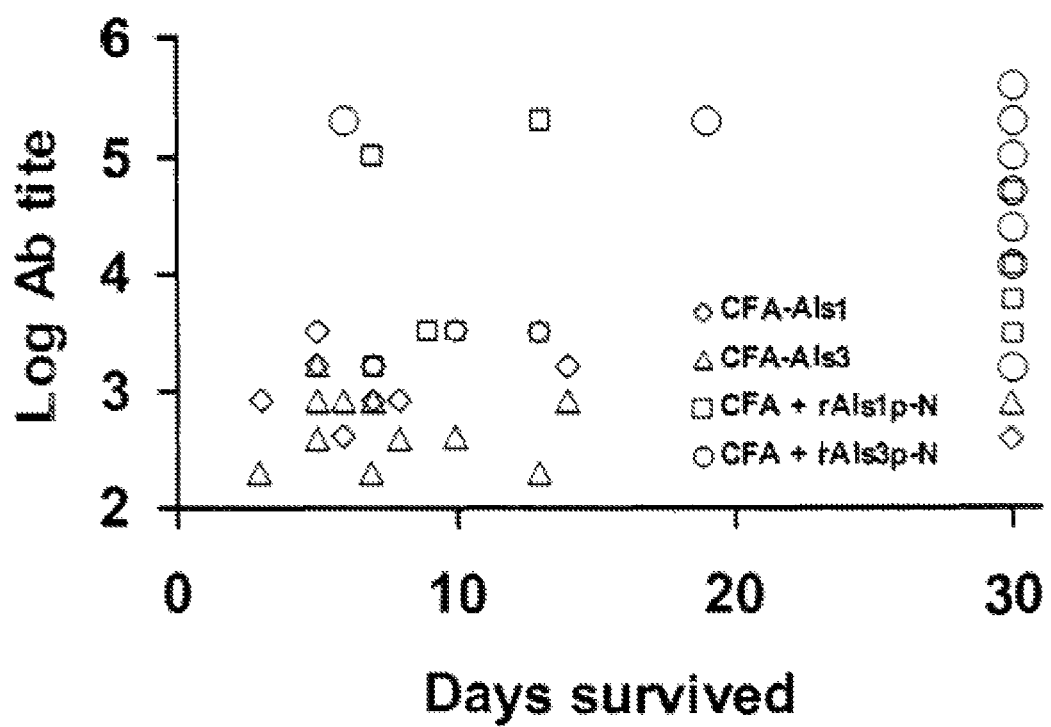

FIG. 28 shows that antibody titers do not correlate with degree of protection in individual vaccinated mice, but they do distinguish unvaccinated from vaccinated mice. Titers of anti-rAls1p-N or anti-rAls3p-N polyclonal antibodies raised in Balb/c mice immunized with CFA alone, or CFA+20 µg of rAls1p-N or rAls3p-N, respectively. Overall there is a significant correlation between antibody titers and survival (rho=0.474, p=0.0057), indicating that antibody titers can be used as a surrogate marker for vaccine protection. However, when data from mice receiving CFA alone are excluded, there is no correlation between antibody titers and survival of mice vaccinated with rAls1p-N or rAls3p-N (rho 0.041143, p=0.847), indicating that antibodies are likely not the predominant mechanism of protection of the vaccine.

Figure 29A:
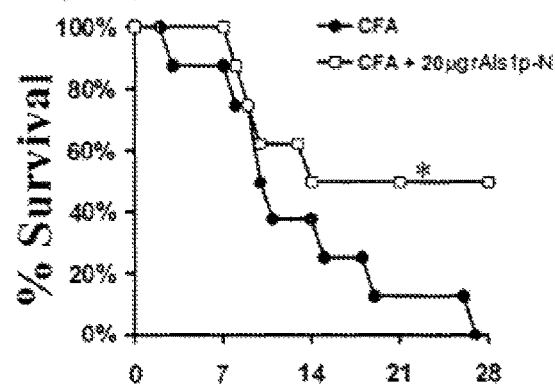
Figure 29B:
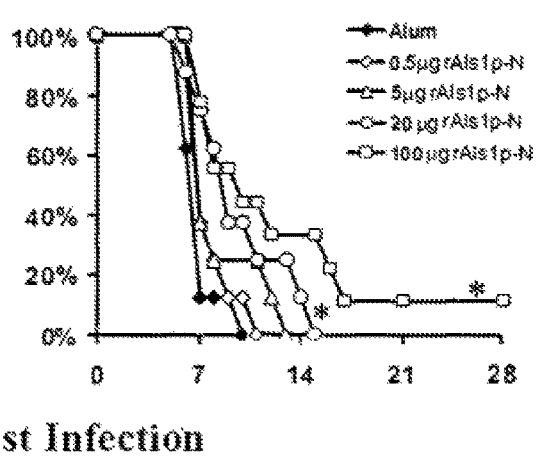

FIGS. 29A and 29B show that the rAls1p-N vaccine protects outbred, CD1 mice from hematogenously disseminated candidiasis. A) CD1 mice (n=8 per group) were vaccinated SQ with rAls1p-N (20 µg)+CFA, or CFA alone, and infected via the tail-vein with *C. albicans* SC5314 fourteen days after the boost. B) CD1 mice (n=8 per group) were vaccinated SQ with rAls1p-N at various doses with alum, or with alum alone, and infected via the tail-vein with *C. albicans* SC5314 fourteen days after the boost. *p<0.05 vs. adjuvant control by Log Rank test.

Figure 30:
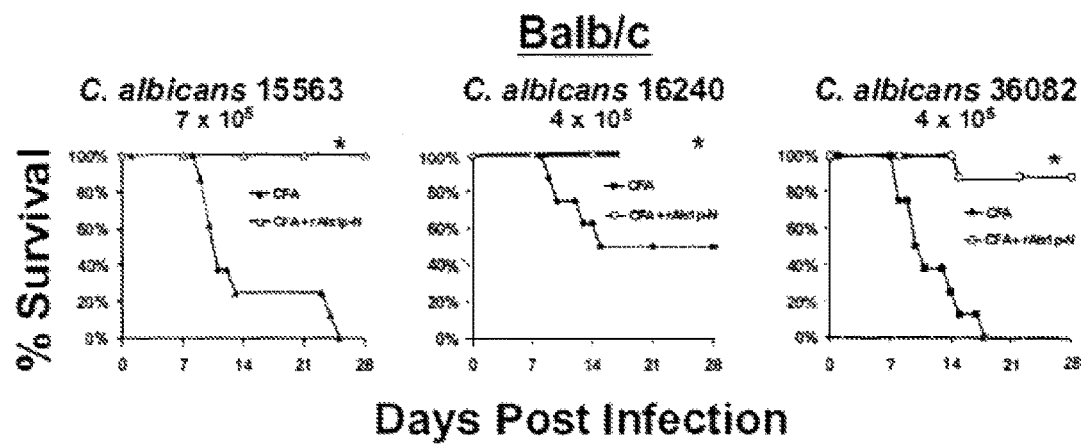

FIG. 30 shows that the rAls1p-N vaccine improves the survival of Balb/c mice infected with one of several strains of *C. albicans*. Survival of Balb/c mice immunized with rAls1p-N plus CFA versus CFA alone and infected via the tail-vein with *C. albicans* 15563 ($7\times10^5$ blastospores), 16240 ($4\times10^5$ blastospores), or 36082 ($4\times10^5$ blastospores) (n=8 mice per group). *p<0.05 vs adjuvant control by Log Rank test.

Figure 31:
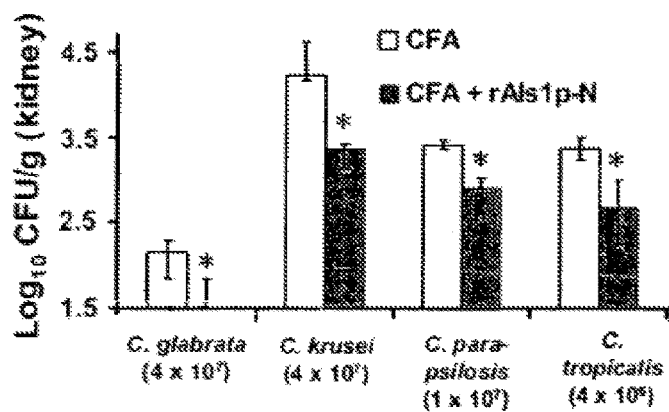

FIG. 31 shows that the rAls1p-N vaccine reduces tissue fungal burden in Balb/c mice infected with several non-albicans species of *Candida*. Balb/c mice (n=5 per group) were vaccinated with CFA or CFA+rAls1p-N (20 µg) and infected via the tail-vein with *C. glabrata, C. krusei, C. parapsilosis*, or *C. tropicalis*. Infectious inocula are shown in parentheses below the species names. Kidney fungal burden was determined on day five post-infection. The y axis reflects the lower limit of detection of the assay. *p<0.05 vs. adjuvant control by non-parametric Steel test for multiple comparisons.

Figure 32:
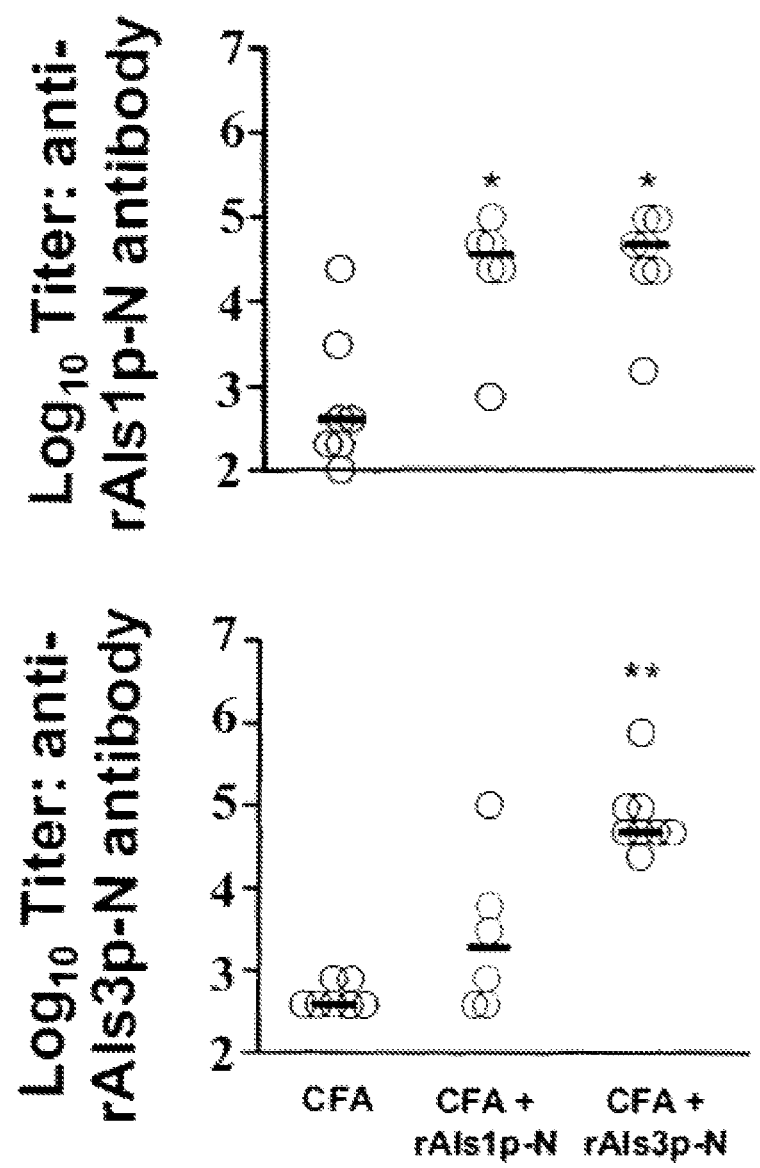

FIG. 32 shows that rAls3p-N-immunized mice generated antibodies that cross-reacted against rAls1p-N. Titers of individual mice immunized with CFA alone, CFA+rAls1p-N, or CFA+rAls3p-N. N=7 mice per group for CFA and CFA+rAls3p-N; n=6 mice for CFA+rAls1p-N. *p<0.05 vs. CFA alone; **p<0.002 vs. CFA alone & p<0.011 vs. CFA+rAls1p-N by Mann Whitney U test. Bars denote medians.

Figure 33:
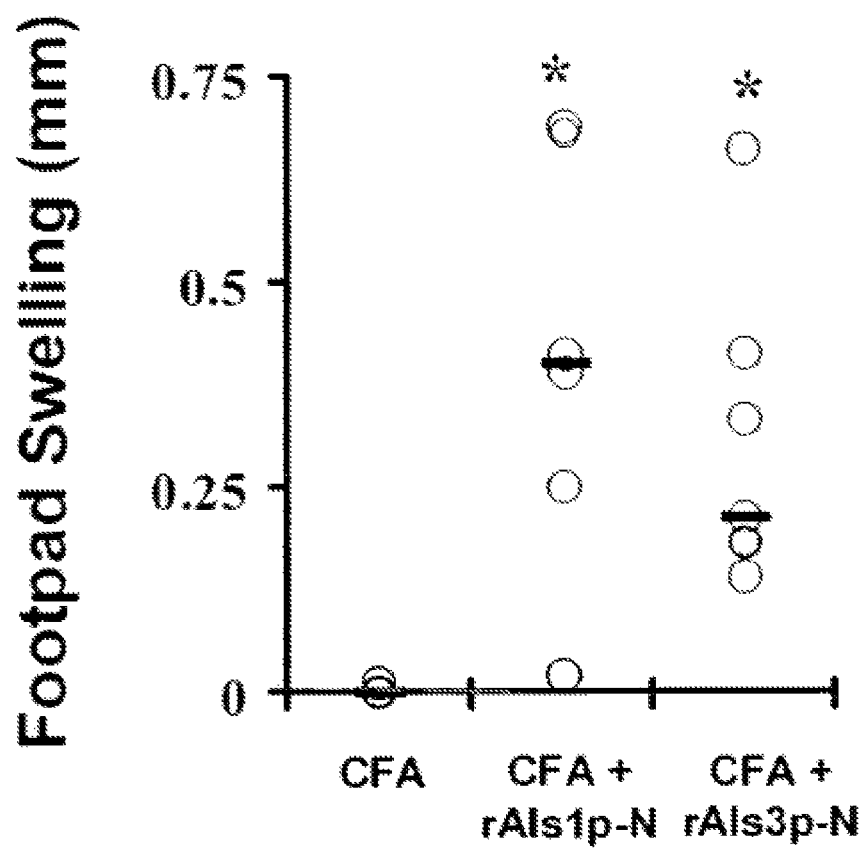

FIG. 33 shows that both rAls1p-N and rAls3p-N primed mice for in vivo delayed type hypersensitivity responses. Mice (n=7 per group for CFA and CFA+rAls3p-N; n=6 for CFA+rAls1p-N) were vaccinated with CFA alone, CFA+rAls1p-N, or CFA+rAls3p-N. Delayed type hypersensitivity in vivo was measured by footpad swelling. *p<0.05 vs. CFA alone by Mann Whitney U test. Bars denote medians.

Figure 34:
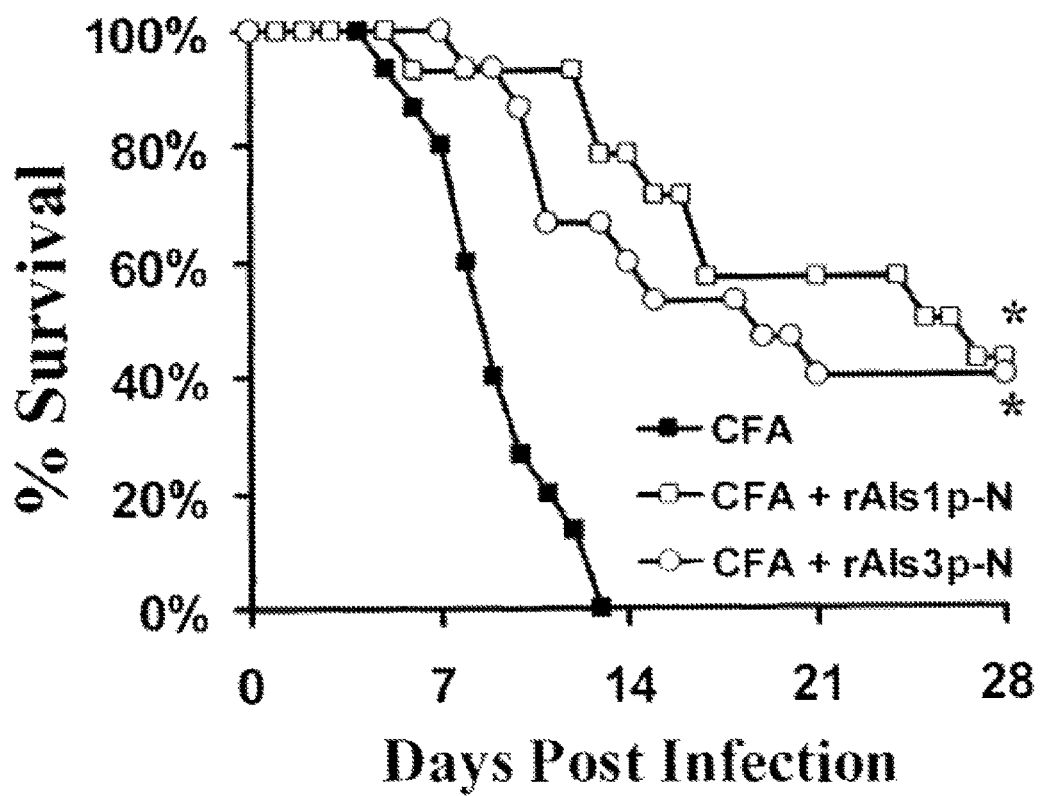

FIG. 34 shows that the rAls1p-N and rAls3p-N vaccines mediated similar efficacy against murine hematogenously disseminated candidiasis. Survival of Balb/c mice (n=15 per group from 2 experiments for CFA and CFA+rAls3p-N, and n=14 from 2 experiments for CFA+rAls1p-N) infected via the tail vein with $5\times10^5$ blastospores of *C. albicans*. The experiment was terminated at day 28 post-infection with all remaining mice appearing well. *p≤0.0001 vs CFA control by Log Rank test.

Figure 35:
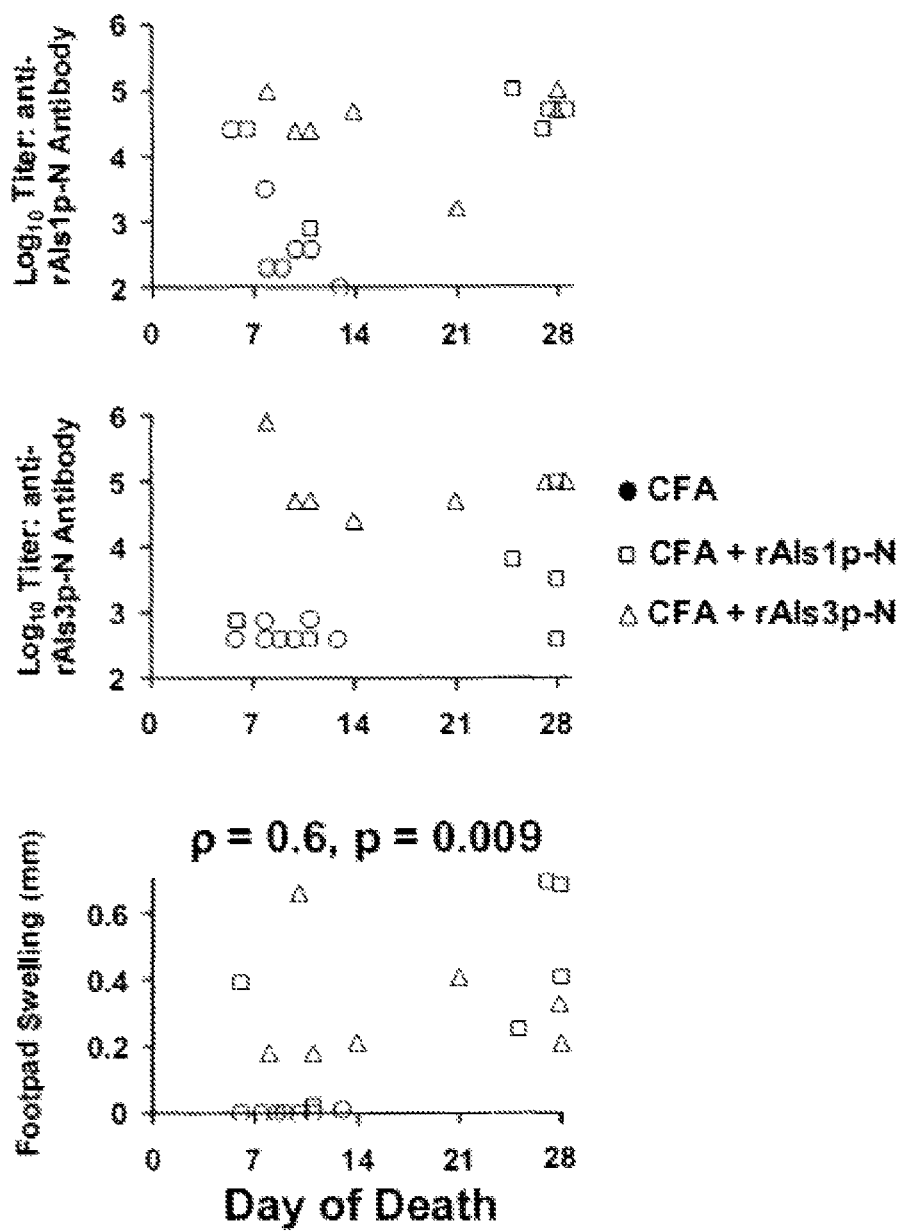

FIG. 35 shows that in vivo delayed-type hypersensitivity correlated with survival during disseminated candidiasis. Anti-rAls1p-N or anti-rAls3p-N antibody titers and footpad swelling reactions were measured in mice (n=7 per group for CFA or CFA+rAls3p-N, n=6 for CFA+rAls1p-N) two days prior to infection via the tail-vein with *C. albicans*. Correlations determined with the Spearman Rank sum test.

Figure 36:
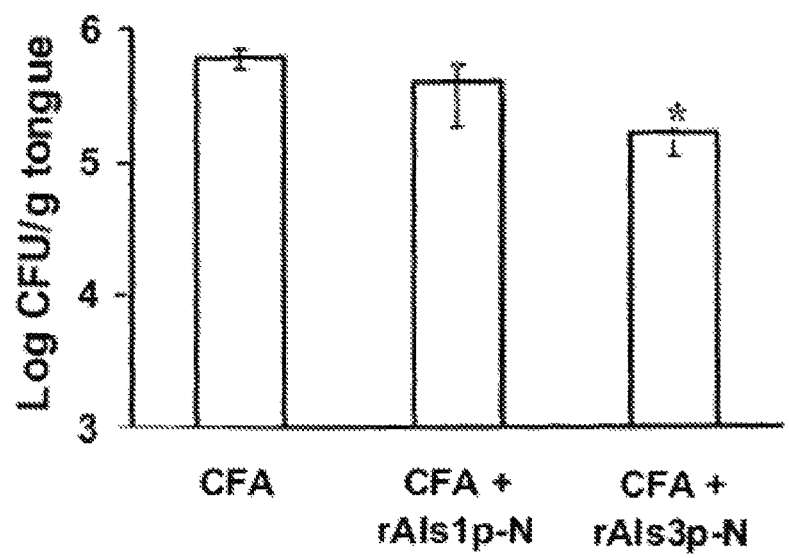

FIG. 36 shows that the rAls3p-N vaccine significantly reduced tissue fungal burden during murine oropharyngeal candidiasis. Tongue fungal burden in mice (n=7 for CFA and 8 for rAls1p-N or rAls3p-N vaccinated groups) with oropharyngeal candidiasis. The y axis reflects the lower limit of detection of the assay. *p=0.005 vs. CFA by Mann Whitney U test.

Figure 37:
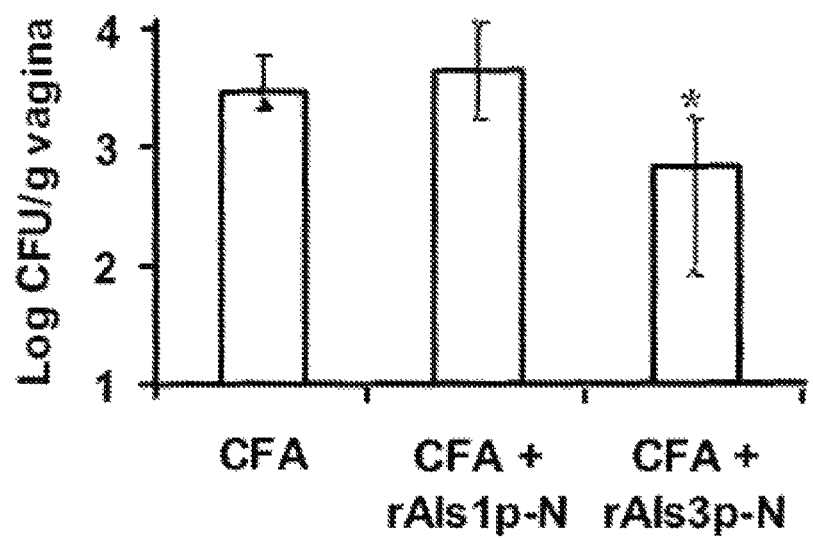

FIG. 37 shows that rAls3p-N reduced vaginal fungal burden compared to both CFA alone and CFA+rAls1p-N in murine candidal vaginitis. Vaginal fungal burden in mice (n=11 per group from 2 experiments) vaccinated with CFA, CFA+rAls1p-N, or CFA+rAls3p-N. The y axis reflects the lower limit of detection of the assay. *p≤0.02 vs CFA and CFA+rAls1p-N by Steel test for multiple comparisons.

DETAILED DESCRIPTION OF THE INVENTION

*Candida albicans* and *Staphylococcus aureus* are common pathogen in humans. For example, *C. albicans*, while normally a harmless commensal, this organism can cause a variety of conditions ranging from superficial mucocutaneous infection such as vaginal and/or oropharyngeal candidiasis, to deep organ involvement in disseminated candidiasis. Prior to causing disease, the fungus colonizes the gastrointestinal tract, and in some cases skin and mucous membranes. Adherence to host mucosal surfaces is a key prerequisite for this initial step. After colonization, *C. albicans* enters the bloodstream via infected intravascular devices or by transmigration through gastrointestinal mucosa compromised by chemotherapy or stress ulcerations. Organisms then disseminate via the bloodstream, bind to and penetrate the vascular endothelium to egress from the vascular tree, and invade deep organs such as liver, spleen, and kidney.

The identification and functional characterizations of a variety of exemplary Als protein family members described herein allow this family of proteins to be effectively utilized in the treatment of candidiasis. Specific binding activity to diverse substrates and other selective cell adhesion functions can be exploited in the production of vaccines for active or passive immunization, in the production of peptide, analogue of mimetic inhibitors of cell adhesion to reduce or prevent initial infection by inhibiting binding, adhesion or invasion of a host cell. Moreover, the differential binding and invasion profiles allow design and use of broad spectra or targeted inhibition of Als protein family member activities. Additionally, functional fragments that confer binding and/or invasive activity allow elimination of unwanted foreign protein sequences, thus, increasing the efficacy of the Als family protein member vaccine or therapeutic inhibitor.

The nature of the pathogenesis of *C. albicans* by adherence to endothelial cells is discussed in U.S. Pat. No. 5,578,309 which is specifically incorporated herein by reference in its entirety. For a description of the ALS1 gene and characteristics thereof, including the characterization of the gene product as an adhesin see, Fu, Y., G. Rieg, W. A. Forizi, P. H. Belanger, J. E. J. Edwards, and S. G. Filler. 1998. Expression of the *Candida albicans* gene ALS1 in *Saccharomyces cerevisiae* induces adherence to endothelial and epithelial cells. Infect. Immun. 66:1783-1786; Hoyer, L. L. 1997. Fu Y, Ibrahim A S, Sheppard D C, Chen Y-C, French S W, Cutler J E, Filler S G, Edwards, J E, Jr. 2002. *Candida albicans* Als1p: an adhesin that is a downstream effector of the EFG1 filamentation pathway. *Molecular Microbiology* 44:61-72. Sheppard D C, Yeaman M R, Welch W H, Phan Q T, Fu Y, Ibrahim A S, Filler S G, Zhang M, Waring A J, Edwards, Jr., J E 2004. Functional and Structural Diversity in the Als Protein Family of *Candida albicans*. *Journal Biological Chemistry*. 279: 30480-30489. The ALS gene family of *Candida albicans*. International Society for Human and Animal Mycology Salsimorge, Italy: (Abstract); Hoyer, L. L., S. Scherer, A. R. Shatzman, and G. P. Livi. 1995. *Candida albicans* ALS1: domains related to a *Saccharonzyces cerevisiae* sexual agglutinin separated by a repeating motif. Mol. Microbiol. 15:39-54.

In this regard, the human fungal pathogen *Candida albicans* colonizes and invades a wide range of host tissues. Adherence to host constituents plays an important role in this process. Two members of the *C. albicans* Als protein family (Als1p and Als5p) have been found to mediate adherence and exemplify the binding, adhesion and cell invasion activities of Als protein family members. As described herein, members of the ALS gene family were cloned and expressed in *S. cerevisiae* to characterize their individual functions. Distinct Als proteins conferred distinct adherence profiles to diverse host substrates. Using chimeric Als5p-Als6p constructs, the regions mediating substrate-specific adherence were localized to the N-terminal domains in Als proteins. In particular, a subset of Als proteins also mediated endothelial cell invasion, a previously unknown function of this family. Consistent with these results, homology modeling revealed that Als members contain antiparallel β-sheet motifs interposed by extended regions, homologous to adhesions or invasins of the immunoglobulin superfamily. This finding was confirmed using circular dichroism and Fourier transform infrared spectrometric analysis of the N-terminal domain of Als1p. Specific regions of amino acid hypervariability were found among the N-terminal domains of Als proteins, and energy-based models predicted similarities and differences in the N-terminal domains that probably govern the diverse function of Als family members. Collectively, these results indicate that the structural and functional diversity within the Als family provides *C. albicans* with an array of cell wall proteins capable of recognizing and interacting with a wide range of host constituents during infection.

The invention provides a vaccine having an isolated Als protein family member having cell adhesion activity, or an immunogenic fragment thereof, and an adjuvant in a pharmaceutically acceptable medium. The vaccine can be an Als protein family member derived from a *Candida* species such as *Candida albicans, Candida krusei, Candida tropicalis, Candida glabrata* or *Candida, parapsilosis*. The Als protein family member can be, for example, Als1p, Als3p, Als5p, Als6p, Als7p and Als9p, or an immunogenic fragment thereof. All other Als protein family members within an *Candida* species can similarly be employed as a vaccine of the invention.

The present invention utilizes the gene product of *C. albicans* agglutinin like sequence protein family member as a vaccine to treat, prevent, or alleviate disseminated candidiasis. The vaccine is effective against different strains of *C. albicans* as well as against different *Candida* species. The Als protein family member can be, for example, Als1p, Als3p, Als5p, Als6p, Als7p and Als9p. The invention exploits the role of the ALS gene products in the adherence of and invasion by *C. albicans* to endothelial and/or epithelial cells and the susceptibility of the Als protein family member-expressed surface protein for use as a vaccine to retard the pathogenesis of the organism.

Pursuant to this invention, an ALS family member gene encodes a surface adhesin that is selected as the target of an immunotherapeutic strategy against *C. albicans*. A demonstration that the expression product of the ALS1 gene, the Als1p protein, has structural characteristics typical of surface proteins and is, in fact, expressed on the cell surface of *C. albicans* is one criterion for proteins that act as adhesins to host tissues. The Als protein family members can be structurally characterized as having a signal peptide at the N-terminus, a glycosylphosphatidylinosine (GPI) anchorage sequence in the C-terminus, and a central region comprising repeats rich in threonine and serine. Also, Als protein family members have N-, and 0-glycosylation sites, typical of proteins that are expressed on the cell surface. Indirect immunofluorescence using a monoclonal antibody directed against the N-terminus of ALs1p, for example, revealed that ALs1p is expressed during the log phase of blastospores. This expression of ALs1p is increased during hyphal formation and is localized to the junction where the hyphal element extends from the blastospores as indicated by the diffused surface staining. Furthermore, this monoclonal antibody blocked the enhanced adherence of *C. albicans* overexpression mutant to endothelial cells, thereby establishing the principle for immunotherapy applications using ALs1p. Functional characteristics as they relate to cell adhesion and invasion of other Als family members are described further below in Example VI.

Thus, according to one aspect, the invention provides an Als family member surface adhesion protein, designated, for example, Als1p, Als3p, Als5p, Als6p, Als7p and Als9p, or a functional fragment, conjugate or analogue thereof, having useful properties when formulated in a pharmaceutical composition and administered as a vaccine with or without an adjuvant. An Als protein family member, combination of two or more Als protein family members or one or more functional fragments, analogues, conjugates or derivatives thereof, can be obtained from, for example, *Candida albicans*. Similar adhesin or invasin molecules or analogues or derivatives thereof can be of candidal origin and can be obtainable, for example, from species belonging to the genera *Candida*, for example *Candida parapsilosis, Candida krusei, Candida glabrata* and *Candida tropicalis*. A surface adhesin or invasin protein according to the invention can be obtained in isolated or purified form, and thus, according to one embodiment of the invention a substantially pure Als protein family member *Candida* surface adhesin protein, or functional fragment, immunogenic fragment, analogue, conjugate or derivative thereof, is formulated as a vaccine to cause an immune response in a patient to elicit an immune response against *Candida* and/or to block adhesion of the organism to the endothelial cells. Fragments of Als protein family members that exhibit similar binding, adhesion or invasion activity as an intact Als protein family member is referred to herein as a functional fragment. Fragments of Als protein family members that are capable of eliciting an antibody or cellular immune response against a *Candida* species are referred to herein as an immunogenic fragment. Exemplary functional fragments include the N-terminal polypeptide region of the Als protein family member described further below in Example VI. Exemplarily immogenic fragments include the N-terminal Als polypeptide region, the C-terminal Als polypeptide region as well as any other Als fragment that is sufficient to generate an antibody, cellular or both an antibody and cellular immune response. Such immogenic fragments can be as small as about four amino acids and as large as the intact polypeptide as well as include all polypeptide lengths in between.

An analogue or derivative of the surface adhesion protein according to the invention can be identified and further characterized by the criteria described herein for an ALS family member gene and/or gene product. For example, a null mutant of the analogue or derivative would share markedly reduced adhesion to endothelial cells compared to controls. Similarly, over-expression of the analogue or derivative in an appropriate model would show an increased adherence to endothelial cells compared to controls and would be confirmed as a cell surface adhesin in accord with the criteria described above. Also, antisera to an analogue or derivative can cross-react with anti-Als protein family member antibodies and can exhibit increased survival times when administered in a mouse model of disseminated candidiasis as disclosed herein.

The invention also provides a method of treating or preventing disseminated candidiasis. The method includes administering an immunogenic amount of a vaccine an isolated Als protein family member having cell adhesion or invasion activity, or an immunogenic fragment thereof, in a pharmaceutically acceptable medium. The vaccine can be administered with or without an adjuvant. The Als protein family member can be derived from different *Candida* strains as well as from different *Candida* species such as *Candida albicans, Candida krusei, Candida tropicalis, Candida glabrata* and *Candida, parapsilosis*. An Als protein family member used in the method of treating or prevention disseminated candidias includes Als1p, Als3p, Als5p, Als6p, Als7p and Als9p.

The effectiveness of the vaccines of the invention against different *Candida* strains, different *Candida* species, other bacteria and infectious agents and their wide range of immune activity are described further below and exemplified in the Examples. For example, Example V shows that anti-ALS antibodies are effective against mucosal and hematogenously disseminated candidal infections. Example VII shows that vaccination with rAls1p-N improves survival during murine disseminated candidiasis by enhancing cell-mediated immunity. Example VIII shows that the vaccines of the invention reduce fungal burden and improve survival in both immunocompetent and immunocompromised mice. Example IX shows the effectiveness of the ALS vaccines of the invention against *S. aureus* infections. Example X exemplifies that the vaccines of the invention are effective against different strains of *C. albicans* and against different species such as *C. glabrata, C. krusei, C. parapsilosis* and *C. tropicalis* as well as effectiveness in different animal models. Example XI also exemplifies the effectiveness of the different vaccines of the invention in different animal models as well as provides a comparison of the different responses elicited and potency of two representative ALS vaccines.

The invention further provided is a method of treating or preventing disseminated candidiasis that includes administering an effective amount of an isolated Als protein family member having cell adhesion activity, or an functional fragment thereof, to inhibit the binding or invasion of *Candida* to a host cell or tissue. The Als protein family member can be derived from *Candida albicans, Candida krusei. Candida tropicalis. Candida glabrata*, and *Candida, parapsilosis*. An Als protein family member used in the method of treating or prevention disseminated candidias includes Als1p, Als3p, Als5p, Als6p, Als7p and Als9p. The cell adhesion activity includes binding to gelatin, fibronectin, laminin, epithelial cells or endothelial cells and/or promoting cell invasion.

In addition, the invention also provides a method of treating or preventing *Staphylococcus aureus* infections using the Als protein family members described herein. In particular, the method of treating or preventing *Staphylococcus aureus* infections includes administering an immunogenic amount of a vaccine an isolated Als protein family member having cell adhesion activity, or an immunogenic fragment thereof, in a pharmaceutically acceptable medium.

Als1p and Als3p are particularly efficacious because of significant homology to *S. aureus* cell surface proteins. The sequence and structural homology of, for example, Als1p and Als3p, are described further below in Example IX. Given the teachings and guidance provided herein, those skilled in the art will understand that the vaccines and methods of the invention can be applied to the treatment of *Candida* and *Staphylococcus* infections alike. Similarly, given the teachings and methods described herein, those skilled in the art also will understand that the vaccines and methods of the invention also can be applied to other pathogens having cell surface polypeptides with similar immunogenicity, sequence and/or structural homology to the Als protein family members described herein, including fungus, bacteria and the like.

Immunotherapeutic and/or Als polypeptide inhibition of cell adhesion or invasion strategies against *Candida* or *Staphylococcus* infection can operate at the level of binding to the vascular endothelial cells as well as through a downstream effector of the filamentation regulatory pathway. An immunotherapeutic strategy or inhibition of binding using a soluble Als protein family member or functional fragment is useful in this context because: (i) the morbidity and mortality associated with hematogenously disseminated candidiasis and other infectious pathogens remains unacceptably high, even with currently available antifungal therapy; (ii) a rising incidence of antifungal and antibiotic resistance is associated with the increasing use of antifungal and antibacterial agents, iii) the population of patients at risk for serious *Candida* and *Staphylococcus* infections is well-defined and very large, and includes post-operative patients, transplant patients, cancer patients and low birth weight infants; and iv) a high percentage of the patients who develop serious *Candida* infections are not neutropenic, and thus may respond to a vaccine or a competitive polypeptide or compound inhibitor. For these reasons, *Candida* and *Staphylococcus* are attractive fungal and bacterial targets for passive immunotherapy, active immunotherapy or a combination of passive or active immunotherapy. Additionally, *Candida* also is attractive for competitive inhibition using an Als protein family member polypeptide, functional fragment thereof and/or a compound or mimetic thereof that binds to one or more Als family members and prevents binding of *Candida* to a host cell receptor.

Given the teachings and guidance provided herein, those skilled in the art will understand that immunotherapeutic methods well know in the art can be employed with the Als protein family members of the invention, immunogenic fragments, analogues, conjugates, and/or derivatives thereof, to use one or more of the molecule as an immunogen in a pharmaceutically acceptable composition administered as a vaccine with or without an adjuvant. For the purposes of this invention, the terms "pharmaceutical" or "pharmaceutically acceptable" refer to compositions formulated by known techniques to be non-toxic and, when desired, used with carriers or additives that can be safely administered to humans. Administration can be performed using well known routes including, for example, intravenous, intramuscular, intraperitoneal or sub-cutaneous injection. Such vaccines of the inventions also can include buffers, salts or other solvents known to these skilled in the art to preserve the activity of the vaccine in solution. Similarly, any of a wide range of adjuvants well known in the art can be employed with the vaccine of the invention to elicit, promote or enhance a therapeutically effective immune response capable of reducing or blocking binding, invasion and/or infection of *Candida* or *Staphylococcus* to a susceptible host cell.

Similarly, given the teachings and guidance provided herein, those skilled in the art also will understand that therapeutic methods well known in the art for administering and selectively blocking the binding of cell surface molecules to their cognate receptors also can be employed with the Als protein family members of the invention, functional fragments, analogues, conjugates and/or derivatives thereof, to use one or more of the Als protein family member as an inhibitor in a pharmaceutically acceptable composition. As with vaccine formulations, inhibitory formulations can similarly be administered using well known method in the art including, for example, intravenous intramuscular, intraperitoneal or sub-cutaneous injection. Such inhibitory compositions that bind Als family member receptors and block an Als protein family member binding also can include buffers, salts or other solvents known to these skilled in the art to preserve the activity of the vaccine in solution. Further, any of a wide range of formulations well known in the art can be employed with the inhibitory compositions of the invention to target and/or enhance delivery or uptake so as to reduce or inhibit binding, invasion and/or infection of *Candida* or *Staphylococcus* to a susceptible host cell.

With respect to the molecule used as a therapeutic immunogen or receptor binding inhibitor pursuant to the present invention, those of skill in the art will recognize that the Als protein family member molecules can be truncated or fragmented without losing the essential qualities as an immunogenic vaccine or cell adhesion or invasion inhibitor. For example, an Als protein family member can be truncated to yield an N-terminal fragment by truncation from the C-terminal end with preservation of the functional properties described above and further below in the Examples. Similarly, C-terminal fragments can be generated by truncation from the N-terminal end with preservation of their functional properties. Other modifications in accord with the teachings and guidance provided herein can be made pursuant to this invention to create other Als protein family member functional fragments, immunogenic fragments, analogs or derivatives thereof, to achieve the therapeutically useful properties described herein with the native protein.

One aspect of the therapeutic effectiveness of Als protein family members and methods of the invention achieves interference with regulation of filamentation, to block adherence of the organism to host constituents, and to enhance clearance of the organism by immunoeffector cells and other physiological mechanisms. Since endothelial cells cover the majority of the vasculature, strategies to block the adherence, invasion and/or both of the organism to endothelial cells using antibodies, Als family member proteins, polypeptide or peptides or any combination thereof include useful embodiment of the present invention. As described previously, such adherence and/or invasion blocking therapies include active or passive immunotherapy or inhibitory binding directed against the candidal adhesins, invasins, or cognate receptors disclosed herein. Thus, for example, any suitable host can be injected with protein and the serum collected to yield the desired anti-adhesin antibody after appropriate purification and/or concentration. Prior to injection, the adhesin or invasin protein or a combination thereof, can be formulated in a suitable vehicle preferably a known immunostimulant such as a polysaccharide or delivery formulation such as liposomes or time-released compositions. Thus, according to a further aspect, invention provides a pharmaceutical composition comprising a candidal adhesin or invasin protein together with one or more pharmaceutically acceptable excipients in a formulation for use as a vaccine or Als receptor inhibitor.

The method of the invention is ameliorating and/or preventing candidal or *Staphylococcus* infection by blocking the adherence of *C. albicans* to the endothelial or epithelial cells of a host constituent or by, for example, antibody binding to the *Staphylococcus* and allowing immune mechanisms remove the pathogen. Thus, according to one aspect of the invention, a pharmaceutical composition comprising an Als protein family member adhesin or invasin protein, functional or immunogenic fragment, derivative, analogue, or conjugate thereof is formulated as a vaccine or Als receptor inhibitor in a pharmaceutical composition containing a biocompatible carrier for injection or infusion and is administered to a patient. Also, direct administration of antiserum raised against Als family member protein or isolated or recombinant Als family member protein can be used to block the adherence of *C. albicans* to a mammalian host constituent or effect the removal of a *Staphylococcus* pathogen. Antiserum against adhesin protein can be obtained by known techniques, Kohler and Milstein, Nature 256: 495-499 (1975), and may be humanized to reduce antigenicity, see U.S. Pat. No. 5,693,762, or produced in transgenic mice leaving an unrearranged human immunoglobulin gene, see U.S. Pat. No. 5,877,397. Similarly, isolated or recombinant Als protein family member also can be produced using methods well known to those skilled in the art including, for example, the recombinant production described in the Examples below.

A still further use of the invention, for example, is using the Als protein family member adhesin or invasin protein to develop vaccine strategies for the prevention and/or amelioration of candidal or *Staphylococcus* infections. Thus, according to one aspect of the invention, for example, standard immunology techniques can be employed to construct a multi-component vaccine strategy that can enhance and/or elicit immune response from a host constituent to bock adherence of *C. albicans* or to effect the elimination of *Staphylococcus* pathogens.

A still further use of the invention, for example, is developing DNA vaccine strategies. Thus, according to one aspect of the invention, for example, the ALS family member polynucleotides encoding Als protein family member adhesin or invasin or a functional fragment thereof is administered according to a protocol designed to yield an immune response to the gene product. See e.g., Felgner U.S. Pat. No. 5,703,055.

A still further use of the invention, for example, is developing combination vaccine strategies. Thus, according to one aspect of the invention, for example, anti-ALS protein family member antibodies may be used with antibodies in treating and/or preventing candidal or *Staphylococcus* infections. See U.S. Pat. No. 5,578,309.

The following Examples illustrate the immunotherapeutic utility of the ALS1 adhesin as the basis for preventive measures or treatment of disseminated candidiasis. Example 1 describes the preparation of an ALS1 null mutant and a strain of *C. albicans* characterized by overexpression of ALS1 to confirm the mediation of adherence to endothelial cells. Example 2 describes the localization of Als1p and the implication of the efg filamentation regulatory pathway. Example 3 describes the purification of ALS1 adhesin protein. Example 4 describes the preparation of rabbit polyclonal antibodies raised against the ALS1 surface adhesin protein to be used to demonstrate the blocking of the surface adhesin protein. Example 5, describes the blocking of adherence in vivo, using polyclonal antibodies raised against the ALS1 surface adhesion protein as described herein according to the invention to protect against disseminated candidiasis in a mouse model. Example VI describes the structural and functional characteristics of Als protein family members.

It is understood that modifications which do not substantially affect the activity of the various embodiments of this invention are also included within the definition of the invention provided herein. Accordingly, the following examples are intended to illustrate but not limit the present invention.

Example I

Als1 Mediates Adherence of *C. albicans* to Endothelial Cells

The URA blaster technique was used to construct a null mutant of *C. albicans* that lacks express of the Als1p. The als1/als1 mutant was constructed in *C. albicans* strain CAI4 using a modification of the Ura-blaster methodology (Fonzi and Irwin, *Genetics* 134, 717 (1993)) as follows: Two separate als1-hisG-IRA3-hisG-als1 constructs were utilized to disrupt the two different alleles of the gene. A 4.9 kb AsLS1 coding sequence was generated with high fidelity PCR (Boehringer Mannheim, Indianapolis, Ind.) using the primers: 5'-CCCTCGAGATGCTTCAACAATTTACATT-GTTA-3' (SEQ ID NO:8) and 5'-CCGCTCGAGT-CACTAAATGAACAAGGACAATA-3' (SEQ ID NO:9). Next, the PCR fragment was cloned into pGEM-T vector (Promega, Madison, Wis.), thus obtaining pGEM-T-ALS1. The hisG-URA3-hisG construct was released from pMG-7 by digestion with Kpn1 and Hind3 and used to replace the portion of ALS1 released by Kpn1 and Hind3 digestion of pGEM-T-ALS1. The final als1-hisG-URA3-hisG-als1 construct was released from the plasmid by digestion with XhoI and used to disrupt the first allele of ALS1 by transformation of strain CAI-4.

A second als1-hisG-URA3-hisG-als1 construct was generated in two steps. First, a Bg12-Hind3 hisG-URA3-hisG fragment of pMB7 was cloned into the BamH1-Hind3 sites of pUC19, thereby generating pYC2. PYC2 was then digested with Hind3, partially filled in with dATP and dGTP using T4 DNA polymerase, and then digested with Sma1 to produce a new hisGURA3-hisG fragment. Second, to generate ALS1 complementary flanking regions, pGEM-T-ALS1 was digested with XbaI and then partially filled in with dCTP and dTTP. This fragment was digested with Hpa1 to delete the central portion of ALS1 and then ligated to the hisG-URA3-hisG fragment generating pYC3. This plasmid was then digested by XhoI to release a construct that was used to disrupt the second allele of the ALS1. Growth curves were done throughout the experiment to ensure that the generated mutations had no effect on growth rates. All integrations were confirmed by Southern blot analysis using a 0.9 kb ALS1 specific probe generated by digestion of pYF5 with XbaI and HindIII.

The null mutant was compared to *C. albicans* CAI-12 (a URA+revertant strain) for its ability to adhere in vitro to human umbilical vein endothelial cells. For adherence studies, yeast cells from YPD (2% glucose, 2% peptone, and 1% yeast extract) overnight culture, were grown in RPMI with glutamine at 25° C. for 1 hour to induce Als1p expression. $3 \times 10^2$ organisms in Hanks balanced salt solution (HBSS) (Irvine Scientific, Irvine, Calif.) were added to each well of endothelial cells, after which the plate was incubated at 37° C. for 30 minutes. The inoculum size was confirmed by quantitative culturing in YPD agar. At the end of incubation period, the nonadherent organisms were aspirated and the endothelial cell monolayers were rinsed twice with HBSS in a standardized manner. The wells were over laid with YPD agar and the number of adherent organisms were determined by colony counting. Statistical treatment was obtained by Wilcoxon rank sum test and corrected for multiple comparisons with the Bonferroni correction. P<0.001.

Figure 1A:
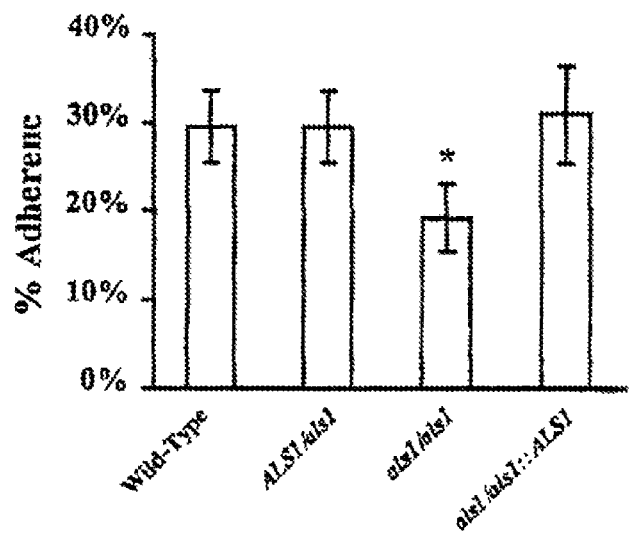
FIGS. 1A-1B show the mediation of Als1p adherence of *C. albicans* to human umbilical vein endothelial cells. Values represent the mean±SD of at least three independent experiments, each performed in triplicate. (A) Endothelial cell adherence of ALS1l/als2 als1/als1 and ALS-complemented mutants and wild-type CAI12(30)(B) Endothelial cell adherence of $P_{ADH1}$-ALS1 mutant that overexpresses ALS1, compared to wild type *C. albicans*. Statistical treatment was obtained by Wilcoxon ran sum test and corrected for multiple comparisons with the Bonferroni correction. *P<0.001 for all comparisons.
Figure 1B:
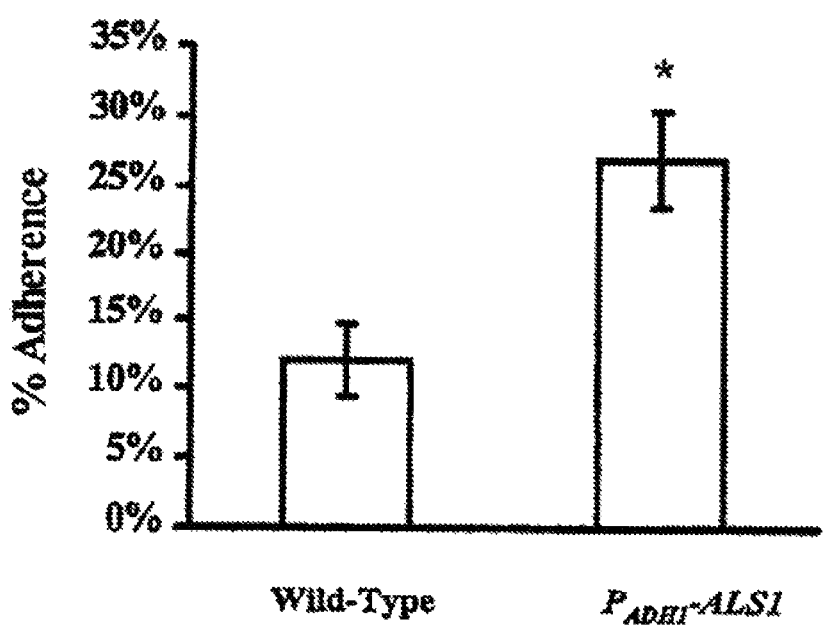

Referring to FIG. 1, a comparison of the ALS1/ALS1 and als1/als1 strain showed that the ALS1 null mutant was 35% less adherent to endothelial cells than *C. albicans* CAI-12. To reduce background adherence, the adherence of the wild-type strain grown under non-ALS1 expressing conditions was compared with a mutant autonomously expressing Als1p. This mutant was constructed by integrating a third copy of ALS1 under the control of the constitutive ADH1 promoter into the wild-type *C. albicans*. To achieve constitutive expression of the ALS1 in *C. albicans*, a blunt-ended PCR generated URA3 gene is ligated into a blunt-edged Bg12 site of pOCUS-2 vector (Novagen, Madison, Wis.), yielding pOU-2. A 2.4 kb Not1-Stu1 fragment, which contained *C. albicans* alcohol dehydrogenase gene (ADH1) promoter and terminator (isolated from pLH-ADHpt, and kindly provided by A. Brown, Aberdeen, U K), was cloned into pOU-2 after digestion with Not1 and Stu1. The new plasmid, named pOAU-3 had only one Bg12 site between the ADH1 promoter and terminator. ALS1 coding sequence flanked by BamH1 restriction enzyme sites was generated by high fidelity PCR using pYF-5 as a template and the following primers: 5'-CGGGATCCAGATGCTTCA-ACAATTTACATTG-3' (SEQ ID NO:10) and 5'-CGGGATCCTCACTAATGAACAAGGACAATA-3' (SEQ ID NO: 11). This PCR fragment was digested with BamH1 and then cloned into the compatible Bg12 site of pOAU-3 to generate pAU-1. Finally, pAU-1 was linearized by XbaI prior to transforming *C. albicans* CAI-4. The site-directed integration was confirmed by Southern Blot analysis. Referring to FIG. 1B, overexpressing ALS1 in this $P_{ADH1}$-ALS1 strain resulted in a 76% increase in adherence to endothelial cells compared to the wild-type *C. albicans*. In comparing endothelial cell adherence of the wild-type to that of the overexpressing mutant, yeast cells were grown overnight in YPD at 25° C. (non-inducing condition of Als1p). Als1p expression was not induced to reduce the background adherence of the wile-type, thus magnifying the role of Als1p in adherence through $P_{ADH1}$-ALS1 hybrid gene. The adherence assay was carried out as described above. Statistical treatment was obtained by Wilcoxon rank sum test and corrected for multiple comparisons with the Bonferroni correction. P<0.001.

A monoclonal anti-Als1p murine IgG antibody was raised against a purified and truncated N-terminus of Als1p (amino acid #17 to #432) expressed using Clontech YEXpress (™) Yeast Expression System (Palo Alto, Calif.). The adherence blocking capability of these monoclonal anti-Als1p antibodies was assessed by incubating C. albicans cells with either anti-Als1 antibodies or mouse IgG (Sigma, St. Louis, Mo.) at a 1:50 dilution. After which the yeast cells were used in the adherence assay as described above. Statistical treatment was obtained by Wilcoxon rank sum test and corrected for multiple comparisons with the Bonferroni correction. P<0.001. The results revealed that the adherence of the $P_{ADH1}$-ALS1 strain was reduced from 26.8%±3.5% to 14.7%±5.3%. Thus, the effects of ALS1 deletion and overexpression demonstrate that Als1p mediates adherence of C. albicans to endothelial cells.

Example II

Localization of Als1p

For Als1p to function as an adhesin, it must be located on the cell surface. The cell surface localization of Als1p was verified using indirect immunofluorescence with the anti-Als1p monoclonal antibody. Diffuse staining was detected on the surface of blastospores during exponential growth. This staining was undetectable on blastospores in the stationary phase. Referring to FIG. 2A, when blastospores were induced to produce filaments, intense staining was observed that localized exclusively to the base of the emerging filament. No immunofluorescence was observed with the als1/als1 mutant, confirming the specificity of this antibody for Als1p. See FIG. 2B. These results establish that Als1p is a cell surface protein.

Figure 3A:
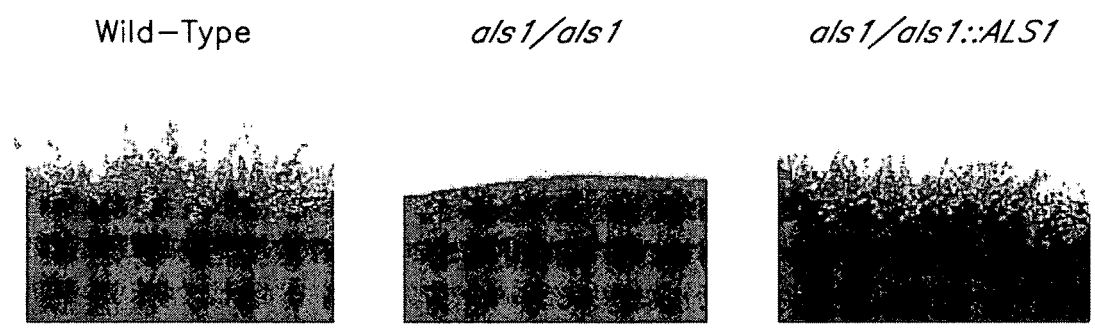

The specific localization of Als1p to the blastospore-filament junction implicates Als1p in the filamentation process. To determine the mechanism, the filamentation phenotype of the C. albicans ALS1 mutants was analyzed. Referring to FIG. 3A, the als1/als1 mutant failed to form filaments after a 4 day incubation on Lee's solid medium, while both the ALS1/ALS1 AND ALS1/als1 strains as well as the ALS-complemented mutant produced abundant filaments at this time point. The als1/als1 mutant was capable of forming filaments after longer periods of incubation. Furthermore, overexpressing ALS augmented filamentation: the $P_{ADH1}$-ALS1 strain formed profuse filaments after a 3 day incubation, whereas the wild-type strain produced scant filaments at this time point. See FIG. 3B. To further confirm the role of Als1p in filamentation, a negative control was provided using mutant similar to the ALS1 overexpression mutant, except the coding sequence of the ALS1 was inserted in the opposite orientation. The filamentation phenotype of the resulting strain was shown to be similar to that of the wild-type strain. The filament-inducing properties of Als1p are specific to cells grown on solid media, because all of the strains described above filamented comparably in liquid media. The data demonstrates that Als1p promotes filamentation and implicates ALS1 expression in the regulation of filamentation control pathways. Northern blot analysis of ALS1 expression in mutants with defects in each of these pathways, including efg1/efg1, cph1/cph1, efg1/efg cph1/cph1, tup1/tup1, and cla4/cla4 mutants were performed. Referring to FIG. 4A, mutants in which both alleles of EFG1 had been disrupted failed to express ALS1. Introduction of a copy of wild-type EFG1 into the efg1/efg1 mutant restored ALS1 expression, though at a reduced level. See FIG. 4B. Also, as seen in FIG. 4A, none of the other filamentation regulatory mutations significantly altered ALS1 expression (FIG. 4A). Thus, Efg1p is required for ALS1 expression.

If Efg1p stimulates the expression of ALS1, which in turn induces filamentation, the expression of ALS1 in the efg1/efg1 strain should restore filamentation. A functional allele of ALS1 under the control of the ADH1 promoter was integrated into the efg1/efg1 strain. To investigate the possibility that ALS1 gene product might complement the filamentation defect in efg1 null mutant, an Ura efg1 null mutant was transformed with linearized pAU-1. Ura$^+$ clones were selected and integration of the third copy of ALS1 was confirmed with PCR using the primers: 5'-CCGTTTATAC-CATCCAATC-3' (SEQ ID NO:13) and 5'-CTACA TCCTC-CAATGATATAAC-3' (SEQ ID NO:14). The resulting strain expressed ALS1 autonomously and regained the ability to filament on Lee's agar. See FIGS. 4B and C. Therefore, Efg1p induces filamentation through activation of ALS1 expression.

Because filamentation is a critical virulence factor in C. albicans delineation of a pathway that regulates filamentation has important implications for pathogenicity. Prior to ALS1, no gene encoding a downstream effector of these regulatory pathways had been identified. Disruption of two other genes encoding cell surface proteins, HWP1 AND INT1, results in mutants with filamentation defects. Although HWP1 expression is also regulated by Efg1p, the autonomous expression of HWP1 in the efg1/efg1 mutant fails to restore filamentation. Therefore Hwp1p alone does not function as an effector of filamentation downstream of EFG1. Also, the regulatory elements controlling INT1 expression are not know. Thus, Als1p is the first cell-surface protein identified that functions as a downstream effector of filamentation, thereby suggesting a pivotal role for this protein in the virulence of C. albicans.

Figure 5A:
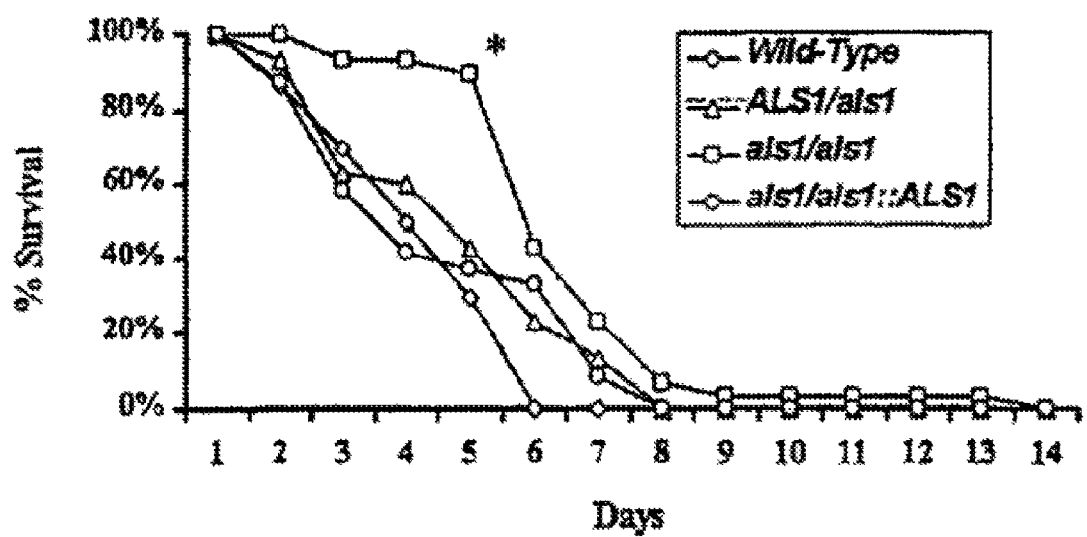
FIGS. 5A-5C show the reduction of virulence in the mouse model of hematogenously disseminated candidiasis. (A) Male Balb/C mice (n=30 for each yeast strain) were injected with stationary phase blastospores ($10^6$ per mouse in 0.5 ml of PBS). Curves are the compiled results of three replicate experiments (n=30 mice for each strain). The doubling times of all strains, grown in YPD at 30° C., ranged between 1.29 to 1.52 hours and were not statistically different from each other. Southern blot analysis of total chromosomal DNA was used to match the identity of the genotype of *C. albicans* strains retrieved from infected organs with those of *C. albicans* strains used to infect the mice. Statistical analysis was obtained by Wilcoxon rank sum test and corrected for multiple comparisons with the Bonferroni correction. *P<0.002 for the als1/als1 mutant versus each of the other strains. (B and C) Histological micrographs of kidneys infected with *C. albicans* wild-type, homozygous als1 null mutant, or heterozygous ALS1 complemented mutant. Kidney samples were retrieved 28 hours (FIG. 5B) or 40 (FIG. 5C) hours post infection, fixed in paraformaldehyde and sections were stained with silver (magnification×400). Arrows denote *C. albicans* cells.
Figure 5B:
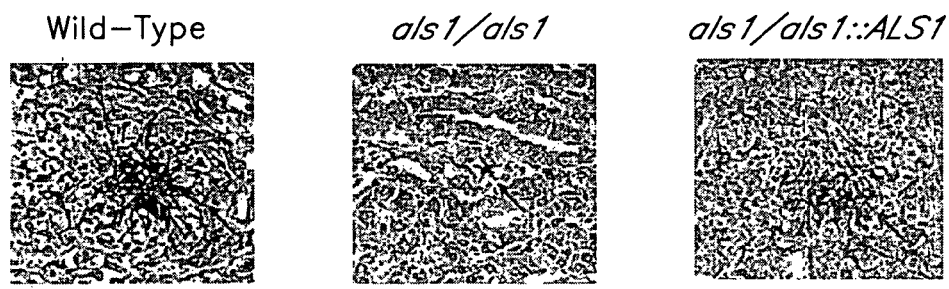
Figure 5C:
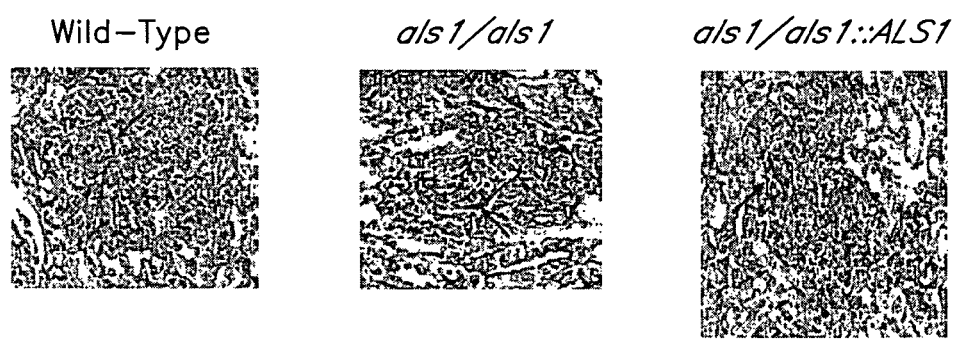

The contribution of Als1p to C. albicans virulence was tested in a model of hematogenously disseminated candidiasis, A. S. Ibrahim et al., Infect. Immun. 63, 1993 (1995). Referring to FIG. 5A, mice infected with the als1/als1 null mutant survived significantly longer than mice infected with the ALS1/ALS1 strain, the ALS1/als1 mutant or the ALS1-complemented mutant. After 28 hours of infection, the kidneys of mice infected with the als1/als1 mutant contained significantly fewer organisms (5.70±0.46 $\log_{10}$ CFU/g) (P<0.0006 for both comparisons). No difference was detected in colony counts of organisms recovered from spleen, lungs, or liver of mice infected with either of the strains at any of the tested time points. These results indicate that Als1p is important for C. albicans growth and persistence in the kidney during the first 28 hours of infection. Referring to FIG. 5B, examination of the kidneys of mice after 28 hours of infection revealed that the als1/als1 mutant produced significantly shorter filaments and elicited a weaker inflammatory response than did either the wild-type of ALS1-complemented strains. However, by 40 hours of infection, the length of the filaments and the number of leukocytes surrounding them were similar for all three strains.

The filamentation defect of the als1/als1 mutant seen on histopathology paralleled the in vitro filamentation assays on solid media. This mutant showed defective filamentation at early time points both in vivo and in vitro. This defect eventually resolved with prolonged infection/incubation. These results suggest that a filamentation regulatory pathway that is independent of ALS1 may become operative at later time points. The activation of this alternative filamentation pathway by 40 hours of infection is likely the reason why mice infected with the als1/als1 mutant subsequently succumbed in the ensuing 2-3 days.

Collectively, these data demonstrate that *C. albicans* ALS1 encodes a cell surface protein that mediates both adherence to endothelial cells and filamentation. Als1p is the only identified downstream effector of any known filamentation regulatory pathway in *C. albicans*. Additionally, Als1p contributes to virulence in hematogenous candidal infection. The cell surface location and dual functionality of Als1p make it an attractive target for both drug and immune-based therapies.

Example III

Purification of ALS1 Adhesin Protein

The ALS1 protein synthesized by *E. coli* is adequate as an immunogen. However eukaryotic proteins synthesized by *E. coli* may not be functional due to improper folding or lack of glycosylation. Therefore, to determine if the ALS1 protein can block the adherence of *C. albicans* to endothelial cells, the protein is, preferably, purified from genetically engineered *C. albicans*.

PCR was used to amplify a fragment of ALS1, from nucleotides 52 to 1296. This 1246 bp fragment encompassed the N-terminus of the predicted ALS1 protein from the end of the signal peptide to the beginning of the tandem repeats. This region of ALS1 was amplified because it likely encodes the binding site of the adhesin, based on its homology to the binding region of the *S. cerevisiae* Aga1 gene product. In addition, this portion of the predicted ALS1 protein has few glycosylation sites and its size is appropriate for efficient expression in *E. coli*.

Figure 7:
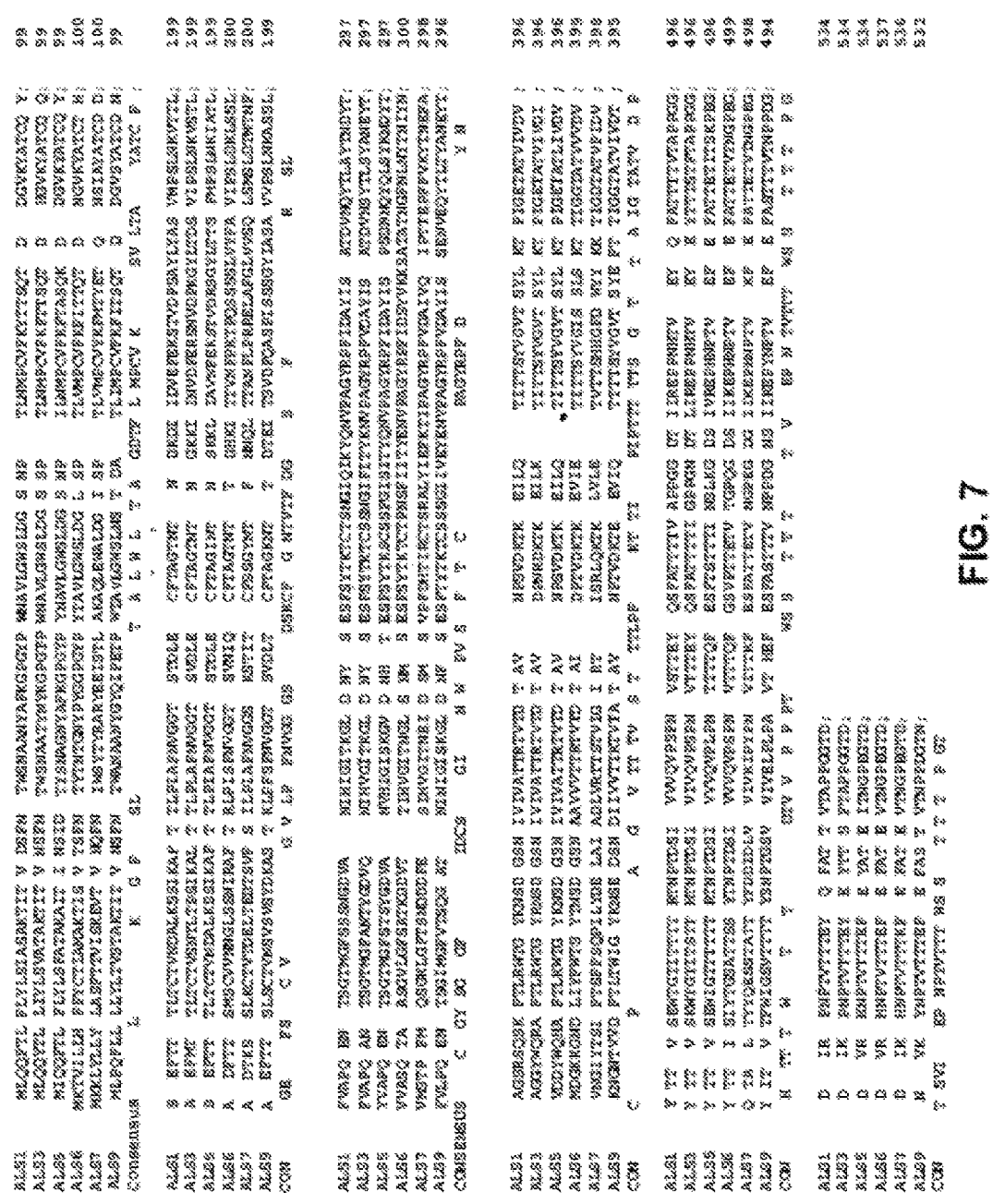

The fragment of ALS1 was ligated into pQE32 to produce pINS5. In this plasmid, the protein is expressed under control of the lac promoter and it has a 6-hits tag fused to its N-terminus so that it can be affinity purified. We transformed *E. coli* with pINS5, grew it under inducing conditions (in the presence of IPTG), and then lysed the cells. The cell lysate was passed through a $Ni^{2+}$-agarose column to affinity purify the ALS1-6His fusion protein. This procedure yielded substantial amounts of ALS1-6His. The fusion protein was further purified by SDS-PAGE. The band containing the protein was excised from the gel so that polyclonal rabbit antiserum can be raised against it. It will be appreciated by one skilled in the art that the surface adhesin protein according to the invention may be prepared and purified by a variety of known processes without departing from the spirit of the present invention. The sequence of Als1p is listed in FIG. 7.

Example IV

Raising Polyclonal Antisera Against ALS1 Protein

To determine whether antibodies against the ALS1 protein block the adherence of *Candida albicans* to endothelial and epithelial cells, and the selected host constituent in vitro, rabbits were inoculated with *S. cerevisiae* transformed with ALS1 protein. The immunization protocol used was the dose and schedule used by Hasenclever and Mitchell for production of antisera that identified the antigenic relationship among various species of *Candida*. Hasenclever, H. F. and W. O. Mitchell. 1960. Antigenic relationships of *Torulopsis glabrata* and seven species of the genus *Candida*. J. Bacteriol. 79:677-681. Control antisera were also raised against *S. cerevisiae* transformed with the empty plasmid. All yeast cells were be grown in galactose to induce expression of the ALS genes. Before being tested in the adherence experiments, the serum was heat-inactivated at 56 C to remove all complement activity.

Sera from immunized rabbits were absorbed with whole cells of *S. cerevisiae* transformed with empty plasmid to remove antibodies that are reactive with components of the yeast other than ALS1 protein. The titer of the antisera was determined by immunofluorescence using *S. cerevisiae* that express the ALS1 gene. FITC-labeled anti-rabbit antibodies were purchased from commercial sources (Southern Biotechnology, Inc). Affinity-purified secondary antibodies were essential because many commercially available sera contain antibodies reactive with yeast glucan and mannan. The secondary antibodies were pretested using *Candida albicans* as well as *S. cerevisiae* transformed with the plasmid and were absorbed as needed to remove any anti-*S. cerevisiae* or anti-*Candida* antibodies. Negative controls were 1) preimmune serum 2) *S. cerevisiae* transformed with the empty plasmid, and 3) *S. cerevisiae* transformed with the ALS gene but grown under conditions that suppress expression of the ALS gene (glucose).

In addition to the above experiments, Western blotting was used to provide further confirmation that an antiserum binds specifically to the ALS protein against which it was raised. *S. cerevisiae* transformed with the ALS1 were grown under inducing conditions and their plasma membranes were isolated by standard methods. Panaretou R and P. Piper. 1996. Isolation of yeast plasma membranes. p. 117-121. In I. H. Evans. (ed.), Yeast Protocols. Methods in Cell and Molecular Biology. Humana Press, Totowa, N.J. Plasma membranes were also prepared from *S. cerevisiae* transformed with the empty plasmid and grown under identical conditions. The membrane proteins were separated by SDS-PAGE and then transferred to PVDF membrane by electroblotting. Harlow, E. and D. Lane. 1988. Antibodies: a laboratory manual. Cold Spring Harbor Laboratory Press. After being blocked with nonfat milk, the blot was incubated with the ALS antiserum. The preabsorbed antiserum did not react with proteins extracted from *S. cerevisiae* containing empty plasmid. This antiserum blocked the adherence of *S. cerevisiae* pYF5 (a clone that expresses *Candida albicans* ALS1) to endothelial cells.

Example V

Polyclonal Antibodies Against Specific ALS Proteins Prophylactically Protect Mice from Mucosal and Hematogenously Disseminated Candidal Infections Having identified the antisera that block the adherence of a clone of *S. cerevisiae* transformed with an ALS gene under the above conditions, these antisera were demonstrated to protect mice from intravenous challenge with *Candida albicans*.

The antisera against the ALS proteins were first tested in the murine model of hematogenously disseminated candidiasis. Affinity-purified anti-ALS antibodies are effective in preventing adhesion of yeast cells to various substrates (see EXAMPLE 3). Affinity-purification is useful in this system because antibody doses can be accurately determined. Moreover, the unfractionated antisera will undoubtedly contain large amounts of antibody directed toward antigens on the *S. cerevisiae* carrier cells. Many of these anti-*Saccharomyces* antibodies would likely bind to *C. albicans* and make interpretation of the results impossible. Additionally, it is quite possible that the procedure used to elute antibodies from *S. cerevisiae* that express the ALS protein may also elute small amounts of yeast mannan or glucan that could have adjuvant-like activity. The immunoaffinity-purified antibodies are further purified before use. They may also be preabsorbed with mouse splenocytes.

Figure 6:
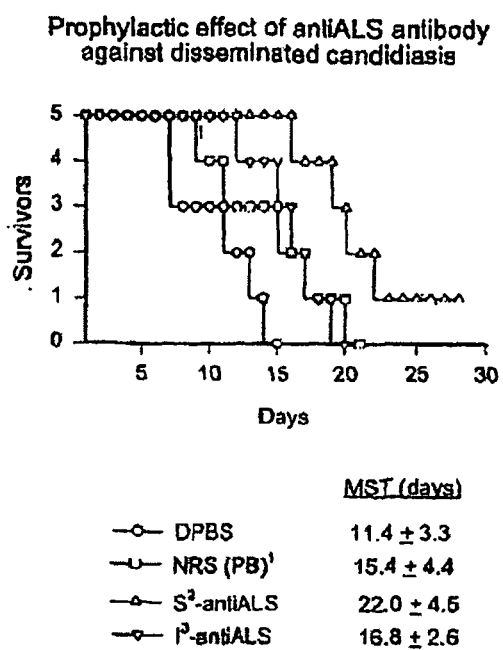
FIG. 6 shows the prophylactic effect of anti-ALS antibody against disseminated candidiasis as a function of surviving animals over a 30-day period for animals infused with anti-Als1p polyserum.

Antibody doses may be administered to cover the range that brackets the levels of serum antibody that can be expected in most active immunization protocols and to cover the range of antibody doses that are typically used for passive immunization in murine models of candidiasis. See Dromer, F., J. Charreire, A. Contrepois, C. Carbon, and P. Yeni. 1987, Protection, of mice against experimental cryptococcosis by anti-*Cryptococcus neofornwns* monoclonal antibody, *Infect. Immun.* 55:749-752; Han, Y. and J. E. Cutler. 1995, Antibody response that protects against disseminated candidiasis, *Infect. Immun.* 63:2714-2719; Mukherjee, J., M. D. Scharff, and A. Casadevall. 1992, Protective murine monoclonal antibodies to *Cryptococcus neofornwns*, *Infect. Immun.* 60:4534-4541; Sanford, J. E., D. M. Lupan, A. M. Schlageter, and T. R. Kozel. 1990, Passive immunication against *Cryptococcus neoformans* with an isotype-switch family of monoclonal antibodies reactive with cryptococcal polysaccharide, *Infect. Immun.* 58:1919-1923. BALB/c Mice (femal, 7 week old, the NCI) were given anti-ALS that had been absorbed with mouse splenic cells by an intraperitoneal (i.p.) injection. Control mice received prebled serum that had been absorbed with mouse spenic cells, intact anti-ALS serum, or DPBS, respectively. For the pre-absorption, 2 ml of anti-ALS or prebled sera were mixed with 100 µl of mouse (BALB/c, 7 weeks old female, NCI) splenic cells (app. 9×10$^6$ cells per ml) at room temperature for 20 minutes. The mixture was washed with warm sterile DPBS by centrifugation (@300×g) for 3 minutes. This procedure was repeated three times. The volume of i.p. injection was 0.4 ml per mouse. Four hours later, the mice were challenged with *C. albicans* (strain CA-1; 5×10$^5$ hydrophilic yeast cells per mouse by i.v. injection. Then, their survival times were measured. See FIG. 6.

Previous studies have shown that antibodies administered via the intraperitoneal route are rapidly (within minutes) and almost completely transferred to the serum (Kozel and Casadevall, unpublished observations). As a control for effects of administering the antibody preparations, a parallel group of mice were treated with antibodies isolated from pre-immune serum that has been absorbed with *S. cerevisia* transformed with the ALS gene. The survival time and numbers of yeast per gram of kidney were measured. Again, referring to FIG. 6, mice infected intravenously with 10$^6$ blastopores of ALS1 null mutant had a longer median survival time when compared to mice infected with *Candida albicans* CAI-12 or *Candida albicans* in which one allele of the ALS1 had been deleted (p=0.00$^3$).

These results indicate that immunotherapeutic strategies using the ALS1 proteins as a vaccine have a protective prophylactic effect against disseminated candidiasis.

Example VI

Functional and Structural Diversity in the Als Protein Family of *Candida albicans*

Isolation and characterized of the *C. albicans* ALS1 gene by heterologous complementation of nonadherent *S. cerevi-* *siae* has been previously described (Fu et al., *Infect. Immun.* 66:1783-1786 (1998)). ALS1 encodes a cell surface protein that mediates adherence to endothelial and epithelial cells. Disruption of both copies of this gene in *C. albicans* is associated with a 35% reduction in adherence to endothelial cells, and overexpression of ALS1 increases adherence by 125% (Fu et al., *Mol. Microbiol.* 44:61-72 (2002)).

ALS1 is a member of a large *C. albicans* gene family consisting of at least eight members originally described by Hoyer et al. (Hoyer et al., *Trends Microbiol.* 9:176-180 (2001), Zhao et al., *Microbiology* 149:2947-2960 (2003)). These genes encode cell surface proteins that are characterized by three domains. The N-terminal region contains a putative signal peptide and is relatively conserved among Als proteins. This region is predicted to be poorly glycosylated, (Zhao et al., *Microbiology* 149:2947-2960 (2003), Hoyer et al., *Genetics* 157:1555-1567 (2001)). The central portion of these proteins consists of a variable number of tandem repeats (~36 amino acids in length) and is followed by a serine-threonine-rich C-terminal region that contains a glycosylphosphatidylinositol anchor sequence (supra). Whereas the proteins encoded by this gene family are known to be expressed during infection (Hoyer et al., *Infect. Immun.* 67:4251-4255 (1999), Zhang et al., *Genome Res.* 13:2005-2017 (2003)), the function of the different Als proteins has not been investigated in detail.

Heterologous expression of Als proteins in nonadherent *S. cerevisiae* was performed to evaluate the function of Als proteins and to avoid the high background adherence mediated by the multiple other adhesins expressed by *C. albicans*. This heterologous expression system has been used extensively for the study of *C. albicans* genes, including the isolation and characterization of the adhesins ALS1, ALS5, and EAP1 (Li et al., *Eukarvot Cell* 2:1266-1273 (2003), Fu et al, *Infect. Immun.* 66:1783-1786 (1998), Gaur et al., *Infect. Immun.* 65:5289-5294 (1997)). As described further below, using this model system Als proteins were demonstrated to have diverse adhesive and invasive functions. Consistent with these results, homology modeling indicated that Als proteins are closely related in structure to adhesin and invasin members of the immunoglobulin superfamily of proteins. Structural analyses using CD and Fourier transform infrared (FTIR)1 spectrometry confirmed that the N-terminal domain of Als1p is composed of anti-parallel β sheet, turn, α-helical, and unstructured domains consistent with the structures of other members of the immunoglobulin superfamily. Finally, comparative energy-based models suggest differences in key physicochemical properties of the N-terminal domains among different Als proteins that may govern their distinct adherence and invasive biological functions.

To clone ALS family members and express them in *S. cerevisiae*, ALS1, -3, -5, -6, -7, and -9 were successfully amplified and expressed as described below. Briefly, for cloning and other culture steps, *S. cerevisiae* strain S150-2B (leu2 his3 trp1 ura3) was used for heterologous expression as has been described previously (Fu et al., *Infect. Immun.* 66:2078-2084 (1998)). *C. albicans* strain SC5314 was used for genomic cloning. All strains were grown in minimal defined medium (1×yeast nitrogen base broth (Difco), 2% glucose, and 0.5% ammonium sulfate, supplemented with 100 µg/ml L-leucine, -L tryptophan, L-histidine, and adenine sulfate) solidified with 1.5% bacto-agar (Difco) as needed. Growth of ura-strains was supported by the addition of 80 µg/ml uridine (Sigma). Plasmids pGK103, containing ALS5, pYF5, containing ALS1, and pALSn, containing ALS9, have been described previously (Fu et al., *Infect. Immune.*

66:1783-1786 (1998), Gaur et al., *Infect. Immune.* 65:5289-5297 (1997), Lucinod et al., *Proceedings of the 102nd Annual Meeting of the American Society for Microbiology*, pp. 204, American Society for Microbiology, Salt Lake City, Utah. (2002)). Plasmid pADH1, obtained from A. Brown (Aberdeen, U K) contains the *C. albicans* alcohol dehydrogenase gene (ADH1) promoter and terminator, which are functional in *S. cerevisiae* (Bailey et al., J. Bacteriol. 178: 5353-5360 (1996)). This plasmid was used for constitutive expression of ALS genes in *S. cerevisiae*.

Human oral epithelial and vascular endothelial cells were obtained and cultured as follows. The FaDu oral epithelial cell line, isolated from a pharyngeal carcinoma, was purchased from the American Type Culture Collection (ATCC) and maintained as per their recommended protocol. Endothelial cells were isolated from umbilical cord veins and maintained by our previously described modification of the method of Jaffe et al. (Fu et al., *Mol. Microbiol.* 44:61-72 (2002), Jaffe et al., *J. Clin. Invest.* 52:2745-2756 (1973)). All cell cultures were maintained at 37° C. in a humidified environment containing 5% CO2.

For cloning the ALS genes, genomic sequences of members of the ALS family were identified by BLAST searching of the Stanford data base (available on the World Wide Web at URL: sequence.stanford.edu/group/candida/search.html). PCR primers were generated to specifically amplify each of the open reading frames that incorporated a 5' BglII and a 3' XhoI restriction enzyme site and are shown below in Table I (SEQ ID NOS:14-19 (ALS1, 3, 5, 6, 7 and 9 sense primers, respectively); SEQ ID NOS:20-25 ((ALS1, 3, 5, 6, 7 and 9 antisense primers, respectively)). Each gene was cloned by PCR using the Expand® High Fidelity PCR system (Roche Applied Science). ALS3, ALS6, and ALS7 were amplified from *C. albicans* SC5314 genomic DNA, whereas ALS1, ALS5, and ALS9 were amplified from plasmids that had been previously retrieved from *C. albicans* genomic libraries (Fu et al., *Infect. Immune.* 66:1783-1786 (1998), Gaur et al., *Infect. Immune.* 65:5289-5297 (1997), Lucinod et al., *Proceedings of the 102nd Annual Meeting of the American Society for Microbiology*, pp. 204, American Society for Microbiology, Salt Lake City, Utah. (2002)). PCR products were ligated into pGEM-T-Easy (Promega) for sequencing. Sequence-verified ALS open reading frames were then released from pGEM-T-Easy by BglII-XhoI co-digestion and ligated into pADH1, such that the ALS gene of interest was under the control of the ADH1 promoter. *S. cerevisiae* strain S150-2B was transformed with each of the ALS overexpression constructs as well as the empty pADH1 construct using the lithium acetate method. Expression of each ALS gene in *S. cerevisiae* was verified by Northern blot analysis before phenotypic analyses were performed.

TABLE I

PCR primers used to amplify the coding regions of ALS gene for heterologous expression in *S. cerevisiae*

| ALS gene | Sense (5'-3') | Antisense (5'-3') |
|---|---|---|
| ALS1 | AGATCTCAGATGCTTCAACAATTTACATTG (SEQ ID NO: 14) | CTCGAGTCACTAAATGAACAAGGACAATA (SEQ ID NO: 20) |
| ALS3 | GAAGATCTATGCTACAACAATATACATTGTTACTC (SEQ ID NO: 15) | CCGCTCGAGTTAAATAAACAAGGATAATAATGTGATC (SEQ ID NO: 21) |
| ALS5 | AGATCTCAACTACCAACTGCTAACA (SEQ ID NO: 16) | CTCGAGACCATATTATTTGGTACAATC (SEQ ID NO: 22) |
| ALS5 | AGATCTCATTCACCGACAATGAAGACA (SEQ ID NO: 17) | CTCGAGTTGGTACAATCCCGTTTGA (SEQ ID NO: 23) |
| ALS7 | AGATCTTCAACAGTCTAATACCTATGA (SEQ ID NO: 18) | CTCGAGACTTGATTGAATTATACCATATA (SEQ ID NO: 24) |
| ALS9 | AGATCTCGAATGCTACCACAATTCCTA (SEQ ID NO: 19) | CTCGAGTCTTAGCACCCTGACGTAGCT (SEQ ID NO: 25) |

ALS mRNA expression was detected by Northern blot analysis for each construct. Despite the use of three sets of primers, amplification of ALS2 and ALS4 from genomic DNA of *C. albicans* SC5314 was unsuccessful. Given the difficulty of sequencing and assembling across the tandem repeats of ALS genes, it is possible that this outcome reflects errors in the sequence assembly currently available on the published genome data base.

Flow cytometry confirmed that each of the Als proteins was expressed on the surface of their respective *S. cerevisiae* hosts. Briefly, confirmation of cell surface expression for each of the Als constructs was determined using indirect immunofluorescence employing two different polyclonal anti-Als antisera. Antiserum A consisted of anti-Als1p antibodies, generated by immunization of rabbits with a 417-amino acid N-terminal fragment of Als1p. Antiserum B was rabbit anti-*C. albicans* mannan factor 5 that recognizes *C. albicans* cell wall components but does not cross-react with *S. cerevisiae* (Iatron Laboratories).

For each strain, $10^7$ blastospores were isolated from overnight culture, blocked with 100 µl of goat serum, and then stained with either polyclonal antiserum A or B at a 1:25 dilution, followed by fluorescein isothiocyanate-labeled goat anti-rabbit IgG at 1:100. A FACSCaliber (Becton Dickinson) instrument equipped with an argon laser emitting at 488 nm was used for flow cytometric analyses. Fluorescence emission was detected with a 515/40-nm bandpass filter. Fluorescence data for 10,000 events were collected, and the distribution of cells with fluorescence above base line (i.e. *S. cerevisiae* transformed with the empty plasmid) was analyzed for each strain using CELLQUEST software (Becton Dickinson).

As shown in Table II, two distinct antisera demonstrated that all of the Alsp-expressing strains exhibited at least a 4-fold increase in fluorescence when compared with *S.* cerevisiae transformed with the empty plasmid. Consistent with the predicted structural diversity among members of the Als family, the antisera displayed differences in recognition of individual Als expression strains.

TABLE II

Detection of Als proteins on the surface of S. cerevisiae by flow cytometric analysis Blastospores of each strain were stained using indirect immunofluorescence with either polyclonal anti-Als1p antiserum (A) or polyclonal anti-C. albicans cell wall antiserum (B) and then analyzed using flow cytometry. Restuls are expressed as percentage of positive cells above background (S. cerevisiae transformed with empty plasmid), with -fold increase in parentheses.

| Als construct | Percentage of cells above background (-fold increase) | |
|---|---|---|
| | Antiserum A | Antiserum B |
| Empty plasmid | (1) | (1) |
| Als1p | 47.8 (17) | 50.1 (19) |
| Als3p | 24.5 (9) | 54.0 (20) |
| Als5p | 23.5 (8) | 28.2 (11) |
| Als6p | 12.7 (4) | 16.2 (6) |
| Als7p | 22.1 (8) | 15.7 (6) |
| Als9p | 11.4 (4) | 33.9 (13) |

S. cerevisiae clones that expressed the various Als proteins were examined for their ability to adhere to a variety of host substrates. As described below, the results show that Als proteins display different profiles of substrate-specific adherence.

Fungal adherence assays were preformed to determine the adherence properties of transformed S. cerevisiae strains. Briefly, a modification of previously described adherence assay (8) was employed as follows. Adherence plates were coated by adding 1 ml of a 0.01 mg/ml solution of gelatin (Sigma), laminin (Sigma), or fibronectin (Becton Dickinson) to each well of a 6-well tissue culture plate (Costar) and incubating overnight at 37° C. For endothelial cells, second passage cells were grown to confluence in 6-well tissue culture plates coated with a 0.2% gelatin matrix, and for epithelial cells, FaDU cells were grown to confluence (3 days) in 6-well tissue culture plates coated with a 0.1% fibronectin matrix. Before adherence testing, wells were washed twice with 1 ml of warm Hanks' balanced salt solution (HBSS). S. cerevisiae strains to be tested were grown overnight in minimal defined media at 30° C. and then harvested by centrifugation, washed with HBSS (Irvine Scientific), and enumerated using a hemacytometer. Three hundred organisms were added to each well of a 6-well tissue culture plate coated with the substrate of interest and incubated for 30 min at 37° C. in CO2. Nonadherent organisms were removed by washing twice in a standardized manner with 10 ml of HBSS. The wells were overlaid with YPD agar (1% yeast extract (Difco), 2% bacto-peptone (Difco), 2% D-glucose, 1.5% agar), and the inoculum was confirmed by quantitative culture. Plates were incubated for 48 h at 30° C., and the colonies were counted. Adherence was expressed as a percentage of the initial inoculum. Differences in adherence were compared using a single factor analysis of variance test, with $p<0.01$ considered significant.

Figure 8:
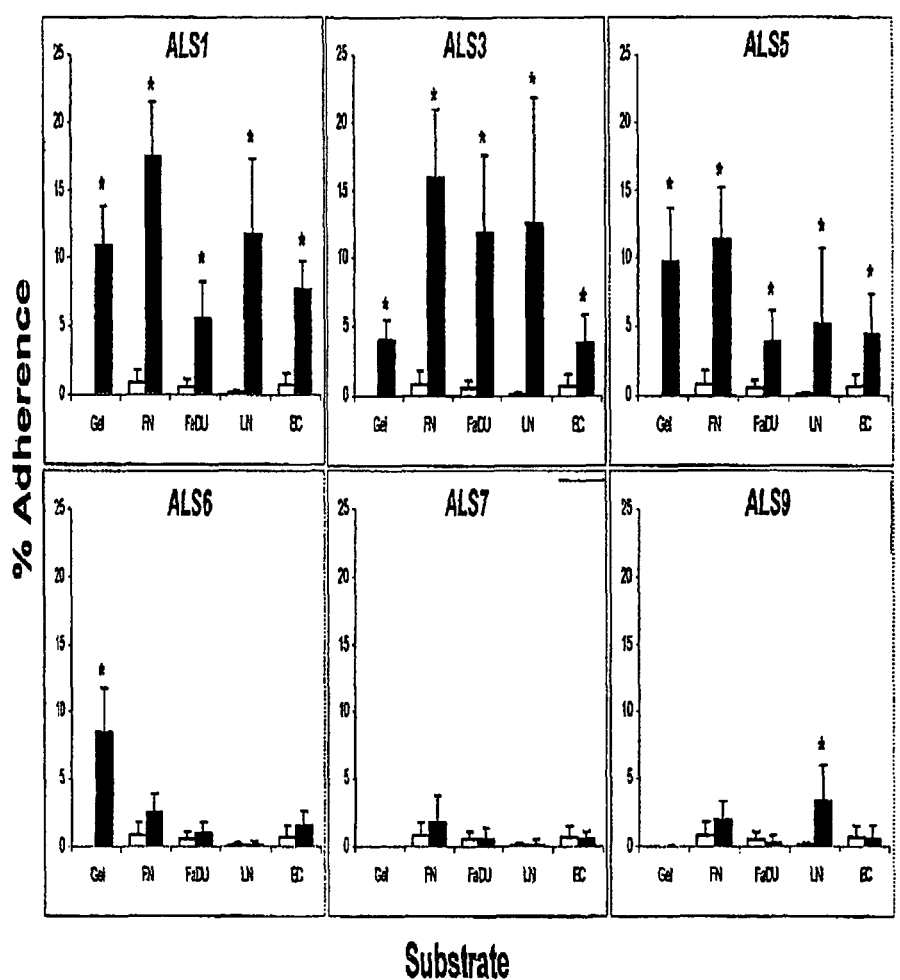
FIG. 8 shows Als proteins confer substrate-specific adherence properties when heterologously expressed in *Saccharonzyces cerevisiae*. Each panel demonstrates the percentage adherence of one Alsp expression strain (filled bars) to a variety of substrates to which *C. albicans* is known to adhere. Adherence of *S. cerevisiae* transformed with the empty vector (empty bars) is included in each panel as a negative control. Gel, gelatin; FN, fibronectin; LN, laminin; FaDU, FaDU epithelial cells; EC, endothelial cells. *, p<0.01 when compared with empty plasmid control by single factor analysis of variance. Results are the mean±S.D. of at least three experiments performed in triplicate.

There were striking differences in the adherence profiles of the S. cerevisiae transformants to the different substrates (FIG. 8). Whereas Als1p-, Als3p-, and Als5p-expressing strains bound to all substrates tested, Als6p-expressing S. cerevisiae adhered only to gelatin, and Als9p-expressing S. cerevisiae adhered above background levels only to laminin.

Further, there were quantitative differences in adherence to the various substrates. For example, when compared with Als3p, Als1p conferred greater adherence to gelatin but less adherence to epithelial cells ($p<0.01$, single factor analysis of variance). Only S. cerevisiae expressing Als7p adhered to none of the substrates tested. Whereas small differences in levels of Als protein expression cannot be ruled out by the immunofluorescence studies shown in Table II, such differences are unlikely to be responsible for the substrate-specific binding patterns found in this study. Such a global increase or decrease in the amount of Als protein expressed on the cell surface would be expected to produce a commensurate increase or decrease in adherence across all substrates and not result in the substrate-specific differences that were observed.

As described below, the substrate binding specificity for Als proteins resides in the N-terminal sequences of Als Proteins. Briefly, Als5p expression in S. cerevisiae confered adherence to multiple substrates, including gelatin and endothelial cells, whereas Als6p expression resulted in adherence to gelatin alone. Despite this marked difference in function, Als5p and Als6p are more than 80% identical at the amino acid level. The tandem repeat and C-terminal portions of these proteins are virtually identical, and the majority of the sequence differences are concentrated in the N termini of these two proteins. These data indicate that N-terminal sequence variability confers substrate specificity.

The above result was supported by the results of studies determining the adherence phenotypes of chimeric ALS5/ALS6 constructs. Briefly, chimeric Als5/Als6 proteins were constructed by exchanging the N termini of each protein. Chimeric ALS5/6 genes were constructed as follows. A BglII-HpaI fragment of ALS5 encompassing the 5' 2117 bp of the gene was isolated. pGEM-T-ALS6 was then digested with BglII and HpaI to release the corresponding 5' 2126 bp of ALS6, and the fragment consisting of pGEM-T-Easy plus the 3' sequences of ALS6 was isolated and ligated to the 5' ALS5 fragment to generate plasmid pGEM-T-5N6C. An identical approach using the corresponding 5' fragment of ALS6 and 3' fragment of ALS5 was used to generate plasmid p-GEM-T-6N5C. After sequence confirmation, each chimeric ALS gene was released by BglII-XhoI digestion and subcloned into pADH1 as above. S. cerevisiae S150-2B was then transformed with these constructs, and expression was verified by Northern blot analysis before characterization of their adherence properties.

Figure 9:
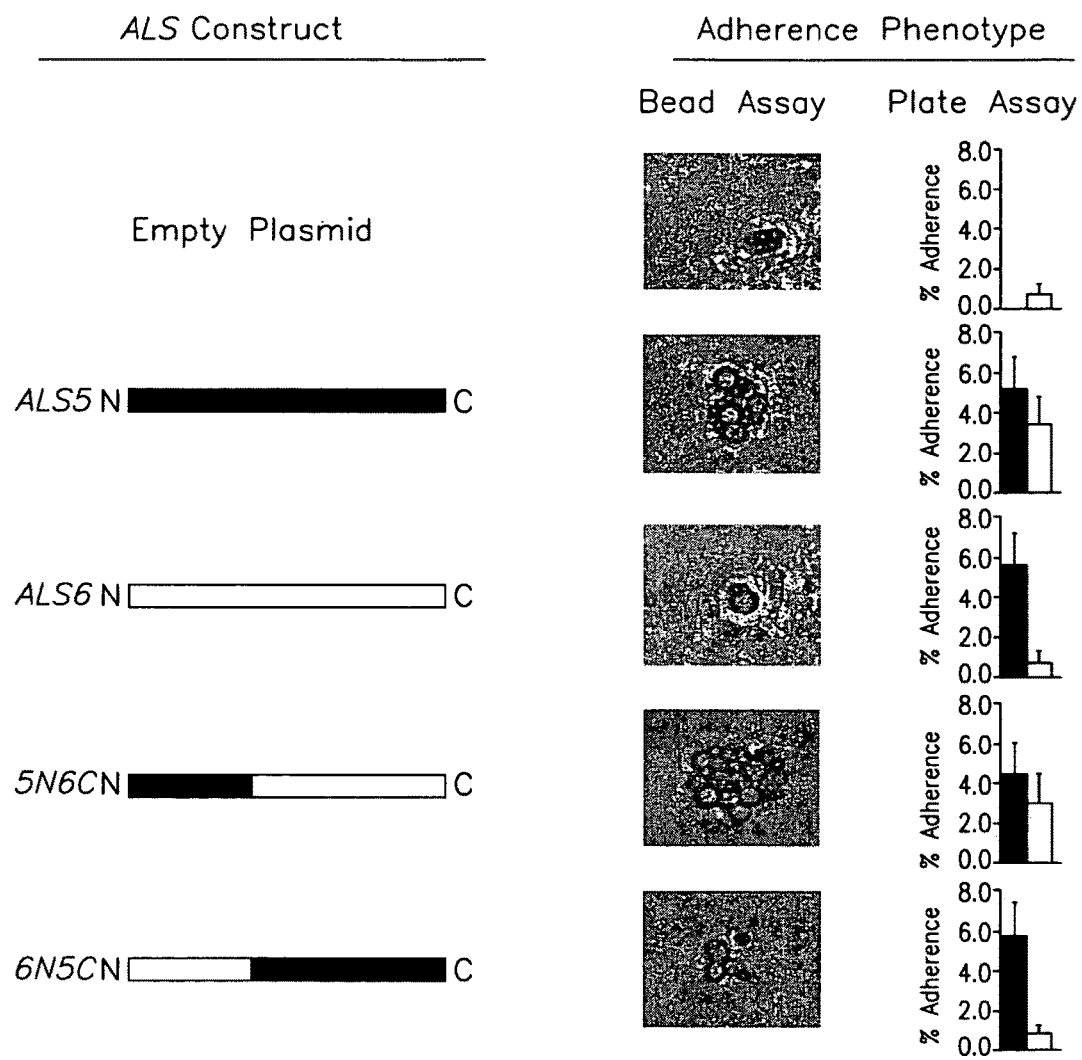
FIG. 9 shows domain swapping demonstrates that substrate-specific adherence is determined by the composition of the N-terminal domain of Als proteins. A representation of the ALS gene or construct being tested is depicted as a bar composed of sequences from ALS5 (black) or ALS6 (white). Adherence properties of each mutant are displayed as a photomicrograph illustrating the adherence of transformed *S. cerevisiae* to fibronectin-coated beads and a graph demonstrating the adherence to gelatin (black bars) and endothelial cells (gray bars) as measured in the 6-well plate assay. Results are mean±S.D. of at least three experiments, each performed in triplicate.

S. cerevisiae expressing a chimeric fusion of the N terminus of Als5p to the C terminus of Als6p adhered to both gelatin and endothelial cells in a manner similar to Als5p (FIG. 9). Likewise, strains expressing the chimeric fusion of the Als6 N terminus to the C terminus of Als5p adhered only to gelatin, as did S. cerevisiae expressing Als6p (FIG. 9). Further, strains expressing Als5p and chimeric Als5N6C protein agglutinated fibronectin-coated beads, whereas those expressing Als6p and chimeric Als6N5C protein had little to no affinity for these beads. Collectively, these data indicate that the adherence profiles of these transformed S. cerevisiae strains were governed by the N-terminal portion of the Als protein.

In addition to the differences in substrate specificity demonstrated between the Als protein family members, differences in other biological functions also were observed. For example, a subset of Als proteins was shown to mediate endothelial cell invasion by S. cerevisiae. C. albicans invades endothelial cells by inducing its own endocytosis (Filler et al., *Infect. Immun.* 63976-983 (1995), Belanger et al., *Cell Microbiol.*, in press (2002)). This endocytosis occurs after the organism adheres to endothelial cells; however, the *C. albicans* ligands required for this process are unknown. Further, it is unclear if distinct candidal ligands are required for both adherence and endocytosis. In addition to being nonadherent, *S. cerevisiae* does not undergo significant endocytosis by endothelial cells. Therefore, to test whether Als proteins could serve as invasins as well as adhesins, the ability of *S. cerevisiae* strains expressing Als proteins to invade endothelial cells was determined.

The ability of Als proteins to mediate endothelial cell invasion was determined using a modification of a previously described differential fluorescence assay (Phan et al., *Infect. Immun.* 68:3485-3490 (2000)). Briefly, endothelial cells were grown to confluence on 12-mm diameter glass coverslips coated with fibronectin and placed in a 24-well tissue culture plate (Corning). Cells were then infected with $10^5$ blastospores of each *S. cerevisiae* strain in RPMI 1640 medium (Irvine Scientific). As a positive control, cells were infected with a similar number of *C. albicans* blastospores. After incubation for 90 min, the cells were rinsed twice with 0.5 ml of HBSS in a standardized manner and fixed with 3% paraformaldehyde. Organisms remaining adherent to the surface of the endothelial cells were stained for 1 h with the rabbit anti-*C. albicans* antiserum (Biodesign), which had been conjugated with ALEXA FLUOR® 568 (Molecular Probes, Inc., Eugene, Oreg.), which fluoresces red. This antiserum cross-reacts with *S. cerevisiae* at a 2-fold higher dilution. The endothelial cells were then permeabilized in 0.2% TRITON X-100 in phosphate-buffered saline for 10 min, after which the cell-associated organisms (the internalized plus adherent organisms) were again stained with the anti-*C. albicans* antiserum conjugated with ALEXA FLUOR® 488, which fluoresces green. The coverslips were then observed under epifluorescence. The number of organisms that had been internalized by the endothelial cells was determined by subtracting the number of adherent organisms (fluorescing red) from the number of cell-associated organisms (fluorescing green). At least 100 organisms were counted on each coverslip, and all experiments were performed in triplicate on at least three separate occasions.

Fibronectin bead adherence assays also was performed to further characterize the binding characteristics of certain Als proteins. In this regard, Als5p was originally identified by virtue of the protein's ability to induce agglutination of fibronectin-coated beads when expressed on the surface of *S. cerevisiae* (Gaur et al., *Infect. Immune.* 65:5289-5297 (1997)). Therefore, *S. cerevisiae* strains transformed with ALS5, ALS6, 5N6C, and 6N5C for fibronectin were tested for bead adherence using this methodology (Gaur et al., *Infect. Immune.* 65:5289-5297 (1997), Gaur et al., *Infect. Immun.* 67:6040-6047 (1999)). Briefly, tosylated magnetic beads (Dynal Biotech) were coated with fibronectin following the manufacturer's instructions. Next, 10 µl of coated beads ($10^6$ beads) were mixed with $1 \times 10^8$ transformed *S. cerevisiae* in 1 ml of 1×Tris-EDTA (TE) buffer, pH 7.0, and incubated with gentle mixing for 45 min. The tubes were placed in a magnet to separate beads and adherent *S. cerevisiae* from nonadherent organisms. The supernatant containing nonadherent organisms was removed by aspiration, and the remaining beads were washed three times by resuspending in 1 ml of TE buffer, followed by magnetic separation and aspiration of the supernatant. Finally, the washed beads and adherent organisms were resuspended in 100 µl of TE buffer and examined microscopically for co-agglutination.

Figure 10:
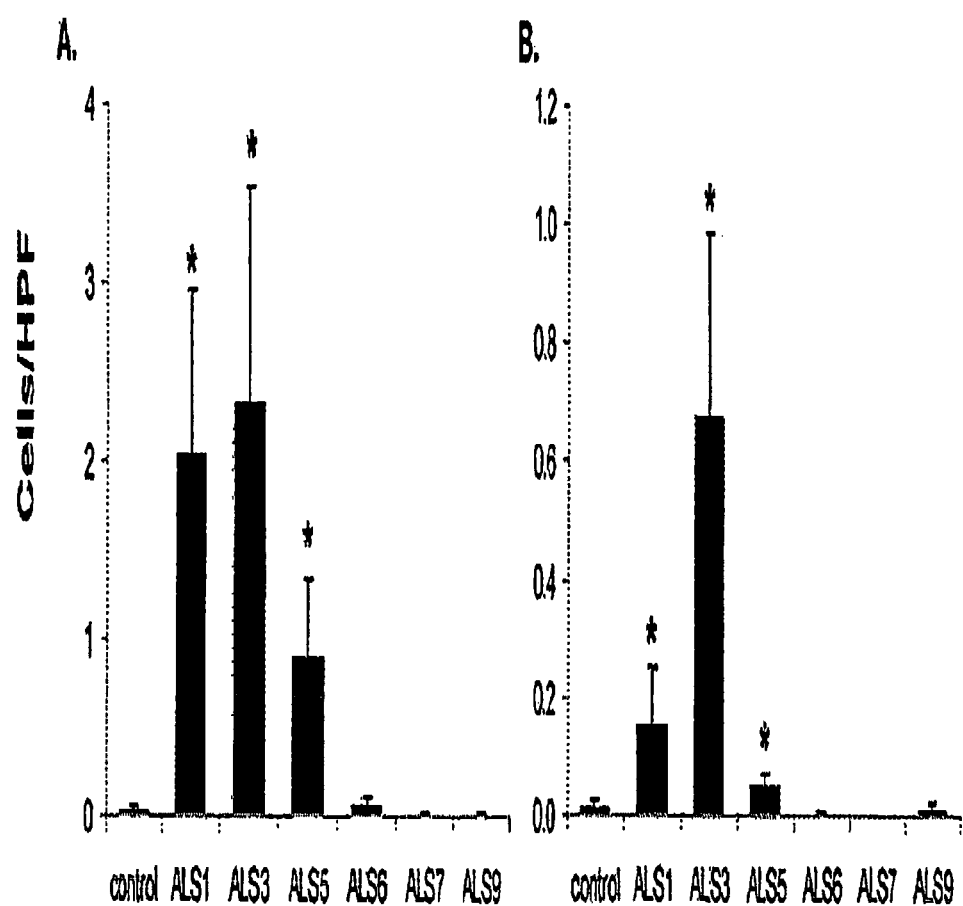
FIG. 10 shows a subset of Als proteins mediate endothelial cell invasion when expressed in *S. cerevisiae*. A, endothelial cell adherence of *S. cerevisiae* strains expressing Als proteins or transformed with the empty plasmid (control). Data represent the total number of endothelial cell-associated organisms and are expressed as cells per high power field. B, degree of endothelial cell invasion of Alsp expressing *S. cerevisiae* strains presented as the number of intracellular organisms per high power field. *, p<0.01 when compared with empty plasmid control by single factor analysis of variance. Results are the mean±S.D. of at least three experiments performed in triplicate.

The results show that *S. cerevisiae* expressing Als1p, Als3p, and Als5p displayed a significant increase in the percentage of cell-associated organisms, reflecting their ability to adhere to endothelial cells. In addition, organisms expressing Als3p and, to a lesser extent, Als1p and Als5p demonstrated significant endothelial cell invasion (FIG. 10).

In addition to the functional studies described above, Als proteins also were found to be homologous to adhesins and invasins of the immunoglobulin superfamily. As an initial step in the molecular modeling of Als proteins, a knowledge-based search algorithm was used to identify molecules that share significant structural similarity with Als family members. Briefly, homology and energy-based modeling was conducted to compare overall physicochemical features of Als proteins. First, a knowledge-based method (SWISS-MODEL) (Guex et al., *Electrophoresis* 18:2714-2723 (1997), Schwede et al., *Nucleic Acids Res.* 31:3381-3385 (2003)) was used to analyze and compare combinatorial extension structural alignments of structures in the Swiss and Brookhaven protein data bases for proteins with homologous conformation (Shindyalov et al., *Protein Eng.* 11:739-747 (1998)). This approach included the BLASTP2 algorithm (Altschul et al., *Mol. Biol.* 215:403-410 (1990)) to search for primary sequence similarities in the ExNRL-3D data base. In parallel, the dynamic sequence alignment algorithm SIM (Huang et al., *Adv. Appl. Math.* 12:337-367 (1991)) was used to select candidate templates with greatest sequence identity. Subsequently, ProModII was used to conduct primary and refined match analyses. Resulting proteins were used as templates for homology modeling of Als protein backbone trajectories.

Robust models of the N-terminal domains of Als proteins (e.g. amino acids 1-480; preceding initial tandem repeats) were generated through complementary approaches. The N-terminal domains of Als proteins were convened to putative solution conformations by sequence homology (Composer (Topham et al. *Biochem. Soc. Symp.* 57:1-9 (1990)) and threading methods (Matchmaker (Godzik et al., *J. Mol. Biol.* 227:227-238 (1992)) and Gene-Fold (Jaroszewski et al., *Protein Sci.* 7:1431-1440 (1998), Godzik et al., *Protein Eng.* 8:409-416 (1995), Godzik et al., *Proc. Natl. Acad. Sci. U.S.A.* 89:12098-12102 (1992), Godzik et al., *J. Comput. Aided Mol. Des.* 7:397-438 (1993)) using SYBYL 6.9.1 software (Tripos Associates) operating on Silicon Graphics workstations (SGI, Inc.). Resulting conformers and amino acid side chains of target Als domains were refined by molecular dynamics, and strain energies were minimized using the AMBER95 force field method (Duan et al., *J. Comput. Chem.* 24:1999-2012 (2003)) and the Powell minimizer (Powell et al., *Math. Program* 12:241-254 (1977)).

These approaches optimize side chain interactions where positions of the peptide backbone atoms are fixed. Preferred conformations were determined from extended molecular dynamics in aqueous solvent. Next, the torsion angles of all peptide bonds were adjusted to 180±150°, with minimal constraints. In some cases, molecular dynamics were executed, either with no constraints or with α-helical regions constrained by applying a 0.4-kJ penalty to the canonical Ramachandran φ and Ψ angles. Final global energy minimizations were performed for each model after the removal of all constraints and aggregates. Resulting Als N-terminal domain models were prioritized based on three criteria: (i) most favorable strain energy (molecular mechanics); (ii) empirical positional energy functions; and (iii) preservation of the spatial arrangement of potential disulfide bridging (Godzik et al., *J. Mol. Biol.* 227:227-238 (1992), Bowie et al., *Science* 253:164-170 (1991), Eisenberg et al., *Methods Enzymol.* 277:396-404 (1997), Fischer et al., *FASEB J.* 10:126-136 (1996), Luthy et al., *Nature* 356:83-85 (1992)).

Als models were assessed for validity in relationship to homology templates using standard measures (e-values (Welch et al., *Biochemistry* 35:7165-7173 (1996), Welch et al., *Biochemistry* 33:6074-6085 (1994)). Finally, the physicochemical properties of the Als models were visualized by MOLCAD (Heiden et al., *J. Comput. Chem.* 14:246-250 (1993)), as implemented in SYBYL and HINT platforms (Kellog et al., *J. Comput. Aided Mol. Des.* 5:545-552 (1991)), such that the physical properties were projected onto the water-accessible surface of the Als N-terminal domains.

These models indicate that the N-terminal domains of all Als proteins contain multiple anti-parallel β-sheet domains, consistent with members of the immunoglobulin superfamily. The results are summarized below in Table III. These proteins typically consist of complex seven-stranded anti-parallel β-sheet domains, from which project loop/coil structures. The β-sheet domains are separated from one another by interposing regions. This structure is often referred to as a beads-on-a-string motif. Particularly noted is that virtually all of the Als proteins modeled to known adhesin or invasin homologs (Table III). Different patterns of similarity were observed among the Als proteins analyzed. For example, all Als proteins examined, except Als7p, shared significant homology with collagen-binding protein of *Staphylococcus aureus*. However, the specific primary, secondary, and tertiary homologs varied for most family members (Table III). For example, Als2p and Als9p shared an identical primary, secondary, and tertiary homolog.

TABLE III

Comparison of homologs among Als proteins
Homologes of each Als protein were identified by the knowledge-based algorithm described and were ranked in descending order of structural correlation from 1 to 3. NS, no significant model identified for homology modeling (correlation coefficient ($(r^2) \leq 70\%$. PDB, Protein Data Bank code per the National Center for Biotechnology Information format.

| Protein | Homolog 1 | Homolog 2 | Homolog 3 |
|---|---|---|---|
| Als1p | Invasin/integrin-binding protein *Yersinia pseuodtuberculosis* (PDB 1cwv)[a] | Collagen-binding protein *Staphylococcus aureus* (PDB 1d2p)[a] | Clumping factor *S. aureus* (PDB 1n67A)[b] |
| Als2p | Collagen-binding protein *S. aureus* (PDB 1d2p)[a] | Invasin/integrin-binding protein *Y. pseuodtuberculosis* (PDB 1cwv)[b] | Surface layer protein *Methanosarcina mazei* (PDB 1LOQA)[c] |
| Als3p | Collagen-binding protein *S. aureus* (PDB 1d2p)[a] | Invasin/integrin-binding protein *Y. pseuodtuberculosis* (PDB 1cwv)[b] | Clumping factor *S. aureus* (PDB 1n67A)[c] |
| Als4p | Collagen-binding protein *S. aureus* (PDB 1d2p)[a] | Invasin/integrin-binding protein *Y. pseuodtuberculosis* (PDB 1cwv)[b] | NS |
| Als5p | Invasin/integrin-binding protein *Yersinia pseuodtuberculosis* (PDB 1cwv)[b] | Surface layer protein *M. mazei* (PDB 1LOQA)[b] | Collagen-binding protein *S. aureus* (PDB 1d2p)[c] |
| Als6p | Collagen-binding protein *S. aureus* (PDB 1d2p)[b] | Invasin/integrin-binding protein *Y. pseuodtuberculosis* (PDB 1cwv)[b] | Neuraminidase Influenza virus type B (PDB 1nsca)[c] |
| Als7p | Surface layer protein *M. mazei* (PDB 1LOQA)[b] | NS | NS |
| Als9p | Collagen-binding protein *S. aureus* (PDB 1d2p)[a] | Invasin/integrin-binding protein *Y. pseuodtuberculosis* (PDB 1cwv)[b] | Surface layer protein *M. mazei* (PDB 1LOQA)[c] |

Als proteins were also determined to contain N-terminal hypervariable regions that map to predicted loop/coil structures. In this regard, despite the observed differences in substrate-specific adherence mediated by individual Als proteins, large regions of sequence in the N-terminal domains are conserved across this family. However, seven regions of significant divergence among Als proteins designated hypervariable regions (HVRs) 1-7, were found. These regions (composed of 8 or more amino acids) contained no apparent consensus identity across Als proteins and less than 50% consensus conservation. In contrast, the intervening conserved regions (CRs) 1-7, displayed more than 30% consensus identity and more than 50% consensus conservation across Als proteins. An identity plot and schematic alignment of these amino acid sequences comprising the N-terminal domains (residues 1-420) of Als proteins with known function is presented in FIGS. 11, A and B. In particular, homology modeling revealed that the HVRs of different Als proteins, while distinguishable in sequence, are predicted to conform to similar loop/coil structures that project from the β-sheet components of the CRs. Thus, the presence of these conserved HVRs indicate that they are available to interact with host constituents.

In addition to the homology modeling and related determinations described above, empirical determinations additionally confirm the predicted structure of the N-terminal domain of Als1p. To test the hypotheses generated by our homology modeling, the structural features of the N-terminal domain of Als1p was determined using the complementary approaches of CD and FTIR spectrometry. This protein, encompassing amino acids 17-432 of Als1p, was produced in *S. cerevisiae* and has been described previously by Fu, et al., *Molecular Microbiology*, 44:61-72 (2002).

Briefly, circular dichroic spectra were recorded with an AVIV 62DS spectropolarimeter (Aviv Biomedical Inc.) fitted with a thermoelectric temperature controller. Aqueous solutions of Als1p (10 μM in phosphate-buffered saline) were scanned using 0.1-mm light path demountable quartz cells at a rate of 10 nm/min from 260 to 185 nm and a sample interval of 0.2 nm. Spectra from buffer lacking peptide were subtracted from sample solutions td minimize light scattering artifacts, and final spectra were an average of 8 scans recorded at 25° C. The instrument was routinely calibrated with (+)-10-camphorsulfonic acid (1 mg/ml in a 1-mm path length cell) (Johnson et al., *Proteins* 7:205-214 (1990)), and ellipticity was expressed as the mean residue ellipticity (1) MRE (degrees-cm2 dmol-1). The protein concentration was determined by absorbance at 280 nm based on aromatic amino acid composition of the expressed Als1p domain (Pace et al, *Protein Sci* 4:2411-2423 (1995)). The CD spectra were deconvoluted into helix, β-sheet, turn, and disordered structures using Selcon (Sreerama et al, *Protein Sci.* 8:370-380 (1999)) through the internet-based Dichroweb (Lobley et al., *Bioinformatics* 18:211-212 (2002)) interface (cryst-.bbk.ac.uk/cdweb/html/home.html).

Infrared spectra of Als1p self-films were recorded at 25° C. on a Bruker Vector 22 FTIR spectrometer (Bruker Optics) fitted with a deuterated triglycine sulfate detector at a gain of 4, averaged over 256 scans, and at a resolution of 2 cm-1. Fifty micrograms of the protein in 50 μl of phosphate-buffered saline were spread onto the surface of a 50×20×2-mm germanium attenuated total reflectance sample crystal (Pike Technologies) and allowed to dry. The dry protein self-film was then hydrated with D2O for 1 h prior to recording the infrared spectra. Amide I bands of the infrared spectra were analyzed for secondary conformations by area calculations of component peaks with curve-fitting software (GRAMS/32, Version 5; Galactic). The frequency limits for the various conformations were as follows: α-helix (1662-1645 cm-1), β-sheet (1637-1613 and 1710-1682 cm-1), β-turn loops (1682-1662 cm-1), and disordered structures (1645-1637 cm-1) (50-52).

Circular dichroism results of the N-terminal domain of Als1p are shown in FIG. 12A and reveal a dichroic minimum at 217 nm and strong positive dichroic maximum near 200 nm. These features are characteristic of a protein having a dominant anti-parallel β sheet component. Deconvolution of the CD spectra indicated that the protein assumed conformations of 50.1% β sheet, whereas other structure class contributions include disordered structures (26.9%), turn structures (19.3%), and α-helix (3.7%).

As shown in FIG. 12B, FTIR measurements of a self-film of the hydrated Als1p strongly corroborated that the sample has a dominant β-sheet conformation. These spectra revealed strong low frequency amide I bands with peaks centered at 1634 and 1628 cm-1 and a weak high frequency band centered at 1685 cm-1. This frequency splitting of the protein amide I infrared spectra into high and low frequency components has been shown to be typical of the effect of transition dipole coupling between intermolecular anti-parallel β-sheets (Halverson et al., *J. Am. Chem. Soc.* 113:6701-6703 (1991)). Curve fitting of the spectra indicated that the protein construct is ~57.2% antiparallel β-sheet. Other secondary structural conformations from curve fitting of the IR spectra include disordered structures (20.5%), turn components (13.3%), and α-helix (9.0%).

Taken together, the FTIR and CD data further corroborate that the N terminus of Als1p contains predominant domains of anti-parallel β-sheet structure containing minor α-helical and turn components, interposed by less structured regions.

Three-dimensional models further indicate Physicochemical distinctions among Als N-terminal domains. In this regard, molecular models indicated differences in predicted physicochemical attributes of the N-terminal domains of Als proteins that likely influence their interactions with host cells and several substrates. As shown in FIG. 13, Als proteins are separable into three distinct groups based on surface distributions of hydrophobicity, charge, and hydrogen bonding potential. Als1p, Als3p, and Als5p each share similar patterns of these properties and thus are considered the Als group A. In contrast, the predicted physicochemical properties of Als6p and Als7p N-terminal domains (Als group B) have striking differences from those of the Als group A (FIG. 13). Whereas the cationic potential in Als group A members is typically segregated from their neutral or anionic facets, positive charge is broadly distributed across the entire surface of the Als group B members Als6p and Als7p. Finally, the N termini of Als2p, Als4p, and Als9p appear to constitute a third group of Als proteins (the Als group C) that differ structurally from either the Als group A or B proteins. The Als group C proteins would appear to be more similar to the Als group A than Als group B proteins in terms of hydrophobic or electrostatic distribution.

Several proteins with adhesive function have been identified in *C. albicans*. Hwp1p has been shown to mediate adherence to buccal epithelial cells by acting as a substrate for mammalian transglutaminase (5). EAP1 was recently identified by heterologous expression in *S. cerevisiae* and mediates adherence to polystyrene and renal epithelial cells in vitro (7). Of the eight members of the Als protein family, only Als1p and Als5p have been studied from a functional perspective. Heterologous expression of Als1p has been shown to mediate binding to human vascular endothelial cells and epithelial cells, a finding that has been confirmed in *C. albicans* through gene disruption studies (Fu et al., *Mol. Microbiol.* 44:61-72 (2002), Fu et al., *Infect. Immune.* 66:1.783-1786 (1998)). Heterologous expression of ALS5 in *S. cerevisiae* confers adherence to collagen, fibronectin, bovine serum albumin, and laminin (Gaur et al., *Infect. Immune.* 65:5289-5297 (1997), Gaur et al., *Infect. Immun.* 67:6040-6047 (1999), Gaur et al., *Cell Commun. Adhes.* 9:45-57 (2002)). No large scale comparison of the substrate specificities of *C. albicans* adhesins has been performed. In this study, we compared the adhesive properties of a structurally diverse group of Als protein family members. Our data demonstrate that the Als proteins comprise a diverse family of surface proteins with an overlapping spectrum of specificities for adherence to a variety of human substrates (FIG. 8). Further, results from the present domain exchange experiments indicate that the N-terminal domains of Als proteins confer the specificity of their substrate adherence profiles.

In addition to mediating adherence, our data suggest that Als proteins also can function as invasins. Interestingly, whereas both Als1p and Als3p expressing *S. cerevisiae* demonstrated similar endothelial cell adherence, Als3p-expressing *S. cerevisiae* underwent internalization at a much higher rate. These results indicate that endocytosis is not simply an extension of adherence but rather a distinct process that can be influenced by the ligand-receptor interaction. It is likely that differences in N-terminal sequences in Als proteins mediate these distinct functions, as is the case with adherence.

The physicochemical properties of protein domains as distributed in three-dimensional space are crucial structural features governing receptor-ligand interactions (Eisenberg et al, *J. Mol. Biol.* 179:125-142 (1984), Waring et al., *Protein Peptidew Lett.* 3:177-184 (1996), Hancock et al., *Lancet* 349:418-422 (1997)). The Als proteins share conformational features characteristic of other adhesins and invasins of the immunoglobulin superfamily. However, individual Als proteins differed in their primary homolog, a finding consistent with the experimental data indicating that members of the Als family exhibit different substrate-binding profiles. Collectively, these patterns of Als homologies indicate that, whereas Als protein members share a global similarity in structure and predicted fold, there exists structural differences among distinct Als proteins that are responsible for their differences in function.

The results described above relating to the Als family member structural determinations corroborate the homology modeling, which indicates that the N-terminal regions of Als1p are composed predominantly of anti-parallel 3-sheet domains containing loop/coil structures, with lesser amounts of relatively unstructured regions. These features are indicative motifs of members of the immunoglobulin superfamily. These results show significant predictive correlation with circular dichroism studies of Als5p (Hoyer et al., *Yeast* 18:49-60 (2001)), indicating that the N-terminal domain of Als5p is characterized by a relative predominance of anti-parallel β-sheet and loop/coil regions. Thus, it is highly likely that all members of the Als protein family exhibit this overall structure. In particular, the structural results above are also consistent with the homology models that indicate that many of the HVRs correspond to the flexible loop/coil structures projecting from β-sheet domains in the N termini of distinct Als proteins. Collectively, these results indicate that these structures are integral to substrate-specific binding by Als proteins (FIG. 14). Consistent with the results above, analogous regions of mannose-binding lectin, α-agglutinin, and other members of the immunoglobulin superfamily appear to confer substrate binding specificity (Zhao et al., *Hybrid Hybridomics* 21:25-36 (2002), Wojciechowicz et al., *Mol. Cell. Biol.* 13:2554-2563 (1993)). Furthermore, mutations of these variable loop regions significantly alter substrate binding in these homologous proteins (Renz et al., *J. Cell Biol.* 125-1395-1406 (1994), Viney et al., *J. Immunol.* 157:2488-2497 (1996)).

The three-dimensional modeling results further indicate that N-terminal domains of individual Als proteins possess distinctive molecular signatures that relate to their adhesive profiles. These signatures incorporate parameters such as surface area, hydrophobicity, and electrostatic charge, yielding configurations that distinguish structural relationships among Als proteins. For example, Als proteins that bind to multiple substrates, such as the Als group A members (Als1p, Als3p, and Als5p), have similar predicted N-terminal profiles in terms of steric bulk, hydrophobic distribution, and electrostatic potential. Yet, even within this group, specific physicochemical distinctions exist that can govern functional differences within the group (FIG. 13). In contrast, Als proteins with reduced adhesive capacity have surface features predicted to be distinct from the Als group A proteins in multiple physicochemical properties, including hydrophobicity and electrostatic potential. It is highly likely that the aggregate effects of differences in these structural features confer the specific functional properties of distinct Als proteins.

Extensive genetic variability has been demonstrated within the ALS gene family. Sequence variation in specific ALS genes of different isolates of *C. albicans* has been observed (Zhang et al., *Genome Res.* 13:2005-2017 (2003), Hoyer et al., *Yeast* 18:49-60 (2001)), and not all members of the ALS family are present in all isolates. Even significant sequence divergence between two different alleles in a single isolate have been found (Zhao et al., *Microbiology* 149: 2947-2960 (2003), Zhang et al., *Genome Res.* 13:2005-2017 (2003)). This degree of genetic variability would suggest that these proteins may undergo rearrangement or mutation at a relatively high frequency. Such a mechanism would provide the organism with the ability to generate the high degree of structural and functional diversity demonstrated in this study. Indirect support for this hypothesis is provided by a recent study of allelic variation of ALS7, which suggested both that this gene is both hypermutable and that these mutations are subject to selective pressure (Zhang et al., *Genome Res.* 13:2005-2017 (2003)).

Collectively, the above results indicate an analogy between antibodies and Als proteins at both the structural and functional level. For example, the homology modeling underscores the similarities in structural configurations of these families, with hypervariability targeted to localized domains within an otherwise stable framework (e.g. HVRs of Als proteins and Fab regions in immunoglobulins). Further, as with antibodies, the genetic variability of the ALS gene family may provide the opportunity for *Candida* to display a diverse array of proteins with a spectrum of specificity in adherence and invasion. The availability of such a group of related proteins is likely to improve the ability of the organism to colonize and invade different anatomical and physiological niches during infection.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

Example VII

Vaccination with rAls1p-N Improves Survival During Murine Disseminated Candidiasis by Enhancing Cell-Mediated, not Humoral, Immunity This example shows that immunizing BALB/c mice with the recombinant N-terminus of Als1p (rAls1p-N) improved survival during subsequent challenge with a lethal inoculum of *C. albicans*. The protective 20 µg dose of rAls1p-N significantly increased *Candida*-stimulation of Th1 splenocytes and increased in vivo delayed type hypersensitivity. In contrast, antibody titers did not correlate with protection. Finally, the vaccine was not protective in T cell-deficient mice but was protective in B cell-deficient mice. These data indicate that the mechanism of action of the rAls1p-N vaccine is stimulation of cell mediated, rather than humoral, immunity against *C. albicans*.

The *C. albicans* used in the study was SC5314, a well-characterized clinical isolate that is highly virulent in animal models (Spellberg et al., *Infect Immun.* 71:5756-5764 (2003)) was supplied by W. Fonzi (Georgetown University). The organism was serially passaged three times in yeast peptone dextrose broth (Difco) prior to infection.

The mice strains used in the study were female BALB/c mice obtained from the National Cancer Institute (Bethesda, Md.). To explore the impact of age on vaccine efficacy, both juvenile mice (8-10 weeks) and retired breeders (≥6 months) were utilized. Female B cell-deficient mice bearing a homozygous deletion of the igh loci (C. 129B6-IgH-Jhdtm1Dhu), T cell-deficient nude mice (C.Cg/AnBomTac-Foxn1nuN20), and congenic wild-type BALB/c littermates were obtained from Taconic Farms (Germantown, N.Y.). Mice were housed in filtered cages with irradiated food and autoclaved water ad libitum. For survival experiments, mice were immunized with varying doses of antigen (see below) and subsequently infected via the tail vein with the appropriate inoculum of *C. albicans* SC5314 blastospores, or PBS (Irvine Scientific, Irvine, Calif.) control. Results of replicate survival studies were combined if the individual datasets demonstrated no statistical heterogeneity (see below). All procedures involving mice were approved by the institutional animal use and care committee, following the National Institutes of Health guidelines for animal housing and care.

The rAls1p-N immunization procedures described below were performed as follows. Briefly, rAls1p-N (amino acids 17 to 432 of Als1p) was produced in *S. cerevisiae* and purified by gel filtration and Ni-NTA matrix affinity purification (Fu et al., *Molec. Microbiol.* 44:61-72 (2002)). The amount of protein was quantified by modified Lowry assay. A high degree of purity (≈90%) was confirmed by SDS-polyacrylamide gel electrophoresis as well as circular dichroism and FTIR, as described above. Mice were immunized by intraperitoneal (ip) injection of rAls1p-N mixed with complete Freund's adjuvant (CFA, Sigma-Aldrich) at day 0, boosted with another dose of the antigen with incomplete Freund's adjuvant (IFA, Sigma-Aldrich) at day 21, and infected two weeks following the boost.

Resultant Antibody titers were determined by ELISA in 96 well plates. Briefly, wells were coated with 100 µl per well of 5 µg/ml rAls1p-N in PBS. Mouse sera were incubated for 1 h at room temperature following a blocking step with tris buffer saline (TBS) (0.01 M TrisHCl, pH 7.4, 0.15 M NaCl) containing 3% bovine serum albumin. The wells were washed 3 times with TBS containing 0.05% TWEEN® 20, followed by another 3 washes with TBS. Goat anti-mouse secondary antibody conjugated with horseradish peroxidase (Sigma) was added at a final dilution of 1:5000 and the plate was further incubated for 1 h at room temperature. Wells were washed with TBS and incubated with substrate containing 0.1 M citrate buffer (pH 5.0), 50 mg/ml of o-phenylenediamine (Sigma), and 10 µl of 30% $H_2O_2$. The color was allowed to develop for 30 min after which the reaction was terminated by adding 10% $H_2SO_4$ and the optical density (OD) was determined at 490 nm in a microtiter plate reader. Negative control wells received only diluent, and background absorbance was subtracted from the test wells to obtain final OD readings. The ELISA titer was taken as the reciprocal of the last serum dilution that gave a positive OD reading (i.e. >mean OD of negative control samples+2 standard deviation).

Other methods described below were performed as follows. Briefly, *C. albicans*-induced cytokine profiles were performed to determine the effect of the rAls1p-N vaccine on cell-mediated immunity and in vivo cytokine profiles. Mice were immunized as described above. Two weeks after the final boost, splenocytes were harvested and cultured in complete media at a density of $4 \times 10^6$ cells/ml as previously described (Spellberg et al., *Infect. Immun.* 71:5756-5764 (2003)). To stimulate cytokine production, splenocytes were co-cultured with heat-killed *C. albicans* SC5314 germ tubes. We used heat-killed *C. albicans* in lieu of rAls1p-N to stimulate the splenocytes to mimic the in vivo situation during infection. The *C. albicans* cells were pre-germinated in RPMI-1640 with glutamine (Gibco BRL) for 90 minutes to induce expression of Als1p (Fu et al., *Molec. Microbiol.* 44:61-72 (2002)). The resulting *C. albicans* germ tubes were heat-killed by incubation for 90 minutes at 60° C. (Ibrahim et al., *Infect. Immun.* 63:4368-74 (1995)). The heat-killed fungi were added to the splenocyte cultures at a density of $2 \times 10^7$ pseudohyphae/ml (ratio of five fungi to one leukocyte). After 48 h, splenocytes were profiled for Th1 (CD4+IFN-□+IL-4-), Th2 (CD4+IFN-□-IL-4+), or CD4+IL-10+ frequencies by intracellular cytokine detection and flow cytometry, as previously described (Spellberg et al., *Infect. Immun.* 71:5756-5764 (2003)). Three-color flow cytometry was performed on a Becton-Dickinson FACScan instrument calibrated with CaliBRITE beads (Becton Dickinson, San Jose, Calif.) using FACSComp software as per the manufacturer's recommendations. During data acquisition, CD4+ lymphocytes were gated by concatenation of forward and side scatter, and FITC-anti-CD4 antibody fluorescence properties. Data for each sample were acquired until 10,000 CD4+ lymphocytes were analyzed. Results are presented as the median±25th and 75th quartiles of the percentage of all gated lymphocytes that were Th1 or Th2 cells.

Footpad swelling was determined by the method of Oomura et al (41). Briefly, mice were immunized with the appropriate dose of rAls1p-N or CFA alone as described above. Two weeks following the boost, baseline footpad sizes of immunized mice were measured using an electronic digital caliper. Fifty µg of rAls1p-N in 25 µl of PBS was injected into the right footpads, and PBS alone injected into the left footpads of the immunized mice. Twenty-four hours later the footpads were again measured. Antigen-specific footpad swelling was calculated as: (right footpad thickness at 24 h–right footpad thickness at baseline)–(left footpad thickness at 24 h–left footpad thickness at baseline).

The non-parametric Log Rank test was utilized to determine differences in survival times of the mice. Titers of antibody, frequency of Th1 or Th2 lymphocytes, and footpad swelling were compared by the Steel test for non-parametric multiple comparisons (Rhyne et al., *Biometrics* 23:539-49 (1967)) or the Mann Whitney U test for unpaired comparisons, as appropriate. Correlations were calculated with the Spearman Rank sum test. To determine if heterogeneity existed in replicate survival studies, the Kolmogorov-Smirnov test was utilized. P values<0.05 were considered significant.

To determine the most effective dose of the rAls1p-N immunogen, a $10^7$-fold dose range was evaluated (20 µg to 200 µg per mouse). Female retired breeder BALB/c mice were immunized with rAls1p-N plus adjuvant (CFA/IFA) or adjuvant alone. Immunized mice were bled 2 weeks after boosting to determine anti-rAls1p-N antibody titers (see below). The mice were subsequently infected with a lethal inoculum of *C. albicans* ($2 \times 10^5$ blastospores). The survival data from repeat experiments were combined since the individual experiments demonstrated no statistical heterogeneity (p>0.05 by Kolmogorov-Smirnov test). The 20 µg dose of rAls1p-N resulted in long-term survival of 25% of the infected mice, and a significant increase in overall survival compared to adjuvant alone (p=0.044 by Log Rank test, FIG. 1). Neither 10-fold higher (FIG. 15) nor lower (data not shown) doses significantly increased survival compared to adjuvant alone. These results indicate that an intermediate dose of the rAls1p-N vaccine induces protection against murine disseminated candidiasis.

The above findings established a protective dose for the rAls1p-N vaccine. Next the efficacy of the vaccine was evaluated in a more rapidly lethal model of mice infected with $10^6$ blastospores (median survival 3 vs. 11 days for $10^6$ vs. $2 \times 10^5$ inocula in unvaccinated mice, respectively). Again the data from repeat studies were combined as the results of the individual experiments demonstrated no statistical heterogeneity (p>0.05 by Kolmogorov-Smirnov test). When administered as a 20 µg dose+CFA to Balb/c mice infected with $10^6$ *C. albicans* blastospores, the rAls1p-N vaccine more than doubled the median survival and resulted in a significant increase in overall survival versus unvaccinated controls (p=0.001 by Log Rank test, FIG. 16A). To determine if the age of the mice influenced their response to the rAls1p-N vaccine, we tested it in juvenile mice. A similar survival benefit was found when juvenile mice were vaccinated and infected with the same high inoculum (p=0.02 by Log Rank test, FIG. 16B).

Although the 200 µg dose of rAls1p-N resulted in inferior protection compared to the 20 µg dose, only the 200 µg dose of antigen induced a significant increase in serum anti-Als1p antibody titers (p≤0.005 for 200 µg dose vs. all other groups, FIG. 17). No significant increases in anti-Als1p antibody titers were detected at the intermediate, protective antigen dose (p=0.1 for 20 µg vs. adjuvant). When the serum anti-Als1p antibody titers of individual mice were plotted against the survival time of each mouse, no correlation between antibody titer and survival was found ($R^2$=0.03, p>0.05 by the Spearman rank sum test). Indeed, mice immunized with the highest dose of antigen (200 µg) had anti-rAls1p-N antibody titers in excess of 1:100,000, but had survival durations no different from mice immunized with lower doses of antigen whose titers were at the lower limit of detection (~1:100). These results indicate that protection induced by the rAls1p-N vaccine does not appear to correlate with antibody titers.

Since humoral immunity did not correlate with rAls1p-N-induced protection, we examined the cell-mediated immune response induced by protective and non-protective doses of rAls1p-N. Mice were immunized with 0.2, 20, or 200 μg of rAls1p-N, or adjuvant alone, as above. Two weeks after the boost, splenocytes were harvested and cultured in the presence of heat-killed, pre-germinated C. albicans, which are known to express Als1p (Fu et al., Molec. Microbiol. 44:61-72 (2002)). Following 48 h of culture, splenocytes were harvested for intracellular cytokine detection by flow cytometry. Only the lymphocytes from mice immunized with the protective 20 μg dose of antigen developed a significantly increased frequency of Th1 cells compared to mice given adjuvant alone (p=0.03, FIG. 18). No significant differences in Th2 frequency (FIG. 18) or in the frequency of IL-10$^+$ T lymphocytes (data not shown) were detected between mice immunized with adjuvant or any of the doses of antigen.

To confirm that Type 1 immunity was stimulated by r-Als1p-N in vivo, delayed type hypersensitivity was tested by footpad swelling. Only mice vaccinated with the protective 20 μg dose of rAls1p-N developed a significantly increased delayed type hypersensitivity reaction compared to control, and this response was also significantly greater than that induced by the non-protective 0.2 and 200 μg doses (FIG. 19, p<0.05 for all comparisons versus 20 μg dose, by the non-parametric Steel test). Collectively, these results indicate that a protective dose of the rAls1p-N antigen induced significant Th1 polarization and delayed type hypersensitivity reaction.

To define the role of antibody and T-cells in vaccine-mediated protection, B cell-deficient, T-cell deficient nude, or congenic BALB/c wild-type control-mice were immunized with 20 μg of rAls1p-N plus adjuvant or adjuvant alone, and infected with a lethal inoculum ($8\times10^5$ blastospores) of C. albicans. B cell-deficient mice trended to being more resistant to infection, whereas T cell-deficient mice were more susceptible, than were wild-type control mice given adjuvant alone (p=0.065 and 0.01 for B cell-deficient and T cell-deficient mice versus wild-type adjuvant-treated, respectively, FIG. 20). Finally, the rAls1p-N vaccine maintained its efficacy in B cell-deficient mice (p=0.04 for rAls1p-N vaccinated versus adjuvant alone, FIG. 6) but was ineffective in T cell-deficient mice (p=0.4 for rAls1p-N vaccinated versus adjuvant alone, FIG. 20). These results indicate that the Als1p vaccine is effective in B cell-deficient mice but not in T-cell deficient nude mice.

Described above are the results showing that immunization with the N-terminus of this protein improved survival of both juvenile and mature BALB/c mice during subsequent hematogenously disseminated candidiasis. In particular, an intermediate dose of rAls1p-N (20 μg) provided superior protection compared to both lower doses and a higher dose (200 μg). Nevertheless, the non-protective 200 μg dose of rAls1p-N was immunogenic, as it induced 100-fold higher titers of antibody than did the protective 20 μg dose.

The inverted U-shaped dose-response efficacy curve, with lower protection at the highest dose of rAls1p-N, is reminiscent of the classical studies of Parish et al., who first described the inverse relationship between the induction of humoral and cell-mediated immunity by a given dose of antigen. In the context of Parish's seminal data, an inverted U-shaped dose-response efficacy curve could be explained if: 1) vaccine efficacy depended on cell-mediated immunity and, 2) intermediate doses of rAls1p-N stimulated superior cell-mediated immunity compared to the high, antibody-stimulating dose. We therefore hypothesized that the inverted U-shaped dose response efficacy curve seen with the rAls1p-N vaccine was due to superior induction of cell-mediated immunity by the protective, intermediate doses of antigen.

To test this hypothesis, the ability of high, intermediate, and low doses of antigen to stimulate Th1 cells and delayed-type hypersensitivity were determined. To stimulate cytokine-production from splenocytes, we specifically activated the cells by exposure to heat-killed C. albicans, instead of rAls1p-N, to mimic the in vivo situation during infection. Only the protective 20 μg dose significantly increased the frequency of C. albicans-stimulated, splenic Th1 lymphocytes. The frequency of Th1 cells seen in ex vivo C. albicans-stimulated splenocytes was similar to that detected in vivo during disseminated candidiasis in mice (59), underscoring the relevance of this approach.

To determine if the detected ex vivo Th1 cells were of functional significance in vivo, we compared the delayed type hypersensitivity induced by different doses of rAls1p-N immunization. Concordant with the frequency of Th1 cells, only the protective 20 μg dose of rAls1p-N stimulated a significant in vive delayed type hypersensitivity reaction. These results are consistent with the hypothesis that vaccine-induced protection was due to induction of Type 1, cell mediated immunity. Surprisingly, despite induction of markedly elevated antibody titers by the 200 μg dose of rAls1p-N, we did not find an increase in splenic Th2 lymphocytes in mice vaccinated with this dose. One possible explanation is that Th2 cells were activated in peripheral lymph nodes rather than the spleen. Alternatively, other T cell populations (e.g. NKT cells) may have been responsible for inducing the high antibody titers seen in response to the 200 μg dose of rAls1p-N.

The lack of correlation between antibody titer and protection did not completely exclude a role of antibodies in mediating vaccine-induced protection. For example, ELISA titers are the result of enumeration of antibodies with a variety of specificities and affinities. Therefore, the possibility that small subsets of antibodies were generated that did participate in vaccine-mediated protection could not be excluded by measuring antibody titer. To confirm the role of cell-mediated and not humoral immunity in rAls1p-N vaccine-mediated protection, we tested the efficacy of the vaccine in B cell- and T cell-deficient mice. B cell-deficient mice trended to being more resistant to disseminated candidiasis than wild-type controls, and the efficacy of the vaccine was not abrogated in B cell-deficient mice. In contrast, T cell-deficient mice were more susceptible to disseminated candidiasis than were wild-type controls, and the efficacy of the vaccine was lost in T cell-deficient mice. Our findings therefore confirm that the efficacy of the rAls1p-N vaccine is dependent of induction of T-cell mediated, and not primarily humoral, immunity. As well, because B cell-deficient mice were not more susceptible to disseminated candidiasis than congenic wild type littermates, antibody is not a dominant effector against disseminated candidiasis in this model.

In sum, we report that the novel rAls1p-N vaccine mediates protection against experimental disseminated candidiasis by inducing cell-mediated rather than humoral immunity. Enhancement of the modest protective effect of the rAls1p-N vaccine may therefore be accomplished with additional priming of cell-mediated immunity using optimized adjuvants and/or cytokines, or an alternate route of immunization. Indeed, in our ongoing studies we have already found a marked increase in efficacy by administering rAls1p-N subcutaneously as compared to intraperitoneally.

Example VIII

The Anti-*Candida albicans* rAls1-N Vaccine Reduces Fungal Burden and Improves Survival in Both Immunocompetent and Immunocompromised Mice This example describes enhancement of the efficacy of the rAls1p-N vaccine described in example VII when administered by a subcutaneous (SQ) route in both immunocompetent and immunocompromised mice. Initially, the efficacy of the rAls1p-N vaccine in immunocompetent mice. rAls1p-N, encompassing amino acids 19-433 of the full length protein, was produced in *S. cerevisiae* and purified as described above. Control preparation was similarly purified from *S. cerevisiae* transformed with an empty plasmid. BALB/c retired breeder mice (25-30 g) were immunized by SQ injection of rAls1p-N (20 µg) or control preparation mixed with Complete Freund's Adjuvant (CFA) at day 0, followed by a booster dose in Incomplete Freund's Adjuvant (IFA) at day 21. Two weeks following the boost, the immunogenicity of the vaccine was confirmed by evaluating the intensity of the footpad swelling reaction as a marker of delayed type hypersensitivity (DTH), as previously described. Vaccinated mice had marked increases in rAls1p-N specific DTH (FIG. 21).

The efficacy of the rAls1p-N vaccine was evaluated by determining the impact of rAls1p-N vaccination on survival in infected BALB/c mice (FIG. 22A). Vaccinated or control mice were infected via the tail-vein with rapidly lethal inocula ($2.5$-$5 \times 10^5$ blastospores) of *C. albicans*. We have previously shown that mice infected such inocula die of overwhelming septic shock (Spellberg et al., *J. Infect. Dis.* In press (2005)). Vaccination markedly prolonged time to death (p<0.05 for both inocula by Log Rank test) and improved 30 day survival (50-57% vs. 0%, p<0.05 for both inocula by Fisher's Exact test).

The impact of vaccination on tissue fungal burden during hematogenously disseminated candidiasis was then determined. Fourteen days following the boost, vaccinated and control BALB/c mice were infected with via the tail-vein with $5 \times 10^5$ blastospores of *C. albicans* SC5314. Six days following infection, prior to onset of the first deaths in the control arm, kidneys were harvested, homogenized, and quantitatively cultured in Sabouraud dextrose agar (Difco) (18). SQ vaccination with rAls1p-N resulted in a median 1.5 log CFU/g decrease in kidney fungal burden compared to control (p=0.01 by Wilcoxon Rank Sum test, FIG. 22B).

The efficacy of the rAls1p-N vaccine also was assessed in immunocompromised mice. Having demonstrated efficacy in immunocompetent mice, the potential for the rAls1p-N vaccine to induce immunity in and protect neutropenic mice from disseminated candidiasis also was evaluated. Vaccinated BALB/c mice were made neutropenic by administration of cyclophosphamide (200 mg/kg ip on day −2, and 100 mg/kg ip on day +9 relative to infection, resulting in approximately 12 days of neutropenia, as described (Sheppard et al., *Antimicrob. Agents. Chemother.* 48:1908-11 (2004)). Footpad swelling reaction was performed 2 days after the first dose of cyclophosphamide. Vaccinated neutropenic mice developed DTH reactions of similar magnitude to immunocompetent mice (FIG. 23A vs. 1, experiments performed in parallel). In neutropenic mice infected via the tail-vein with $2.5 \times 10^4$ blastospores of *C. albicans*, vaccination also resulted in significant improvements in time to death (p=0.007 by Log Rank test vs. Control), median survival time (>21 vs 12 d, p=0.008 by Wilcoxon Rank Sum Test), and overall survival (88% vs. 38%, p=0.005 by Fisher's Exact test) (FIG. 23B).

To determine the efficacy of rAls1p-N vaccination in mucosal infection, the vaccine was tested in a murine oropharyngeal candidiasis (OPC) model (Kamai et al., *Infect. Immun.* 70:5256-8 (2002) and Kamai et al., *Antimicrob. Agents Chemother.* 45:3195-97 (2001)) Vaccinated mice were treated with cortisone acetate (225 mg/kg SQ on days −1, 1, and 3 relative to infection) and infected sublingually as described. Tongues were excised on day 5 post-infection. Because colony forming units of homogenized tongues cannot distinguish between invasive infection and surface-adherent colonization, we evaluated extent of invasion by histopathology. A blinded observer (BJS) scored each section by scanning along the entire length of the tongues and quantifying the severity of fungal lesions per $40 \times$ high-powered field ($0$=no lesion, $1^+$=mild mucosal inflammation, $2^+$=significant inflammation restricted to the epithelium, $3^+$=inflammation extending through the entire epithelial layer, $4^+$=inflammation extending into the subepithelium). To avoid sampling bias, two sections of each tongue, separated by at least five intervening tissue sections, were scored. All control mice developed marked fungal invasion of their tongues in numerous locations, while only two vaccinated mouse developed any tongue lesions. In total, the median number ($75^{th}$, $25^{th}$ quartile) of lesions per tongue in control mice was 6.5 (8, 5.75) as compared to 1 (2.5, 0) for vaccinated mice (p=0.03 by Wilcoxon Rank Sum test). Semi-quantitative evaluation of the severity of infection demonstrated a significant reduction in vaccinated mice compared to controls (FIG. 24, p=0.03 by Wilcoxon Rank Sum test).

To determine the efficacy of rAls1p-N or rAls3-p-N vaccination in mucosal infection, these two vaccines in a murine model of vaginal colonization (Clemons et al., *Infect. Immun.* 72: 4878-80 (2004); Fidel. *Int Rev Immunol.* 21: 515-48 (2002) and Wozniak et al., *Infect Immun.* 70: 5790-9 (2002)). Vaccinated mice were treated with estrogen (30 µg, given SQ) on day −3 relative to infection and then challenged in the vagina with 10 µl phosphate buffered saline containing $10^6$ blastospores of *C. albicans*. Vaginas were excised on day 3 post-inoculation, homogenized and serial dilutions were plated on YPD plates. Colony forming units (CFU) were enumerated 24-48 h following incubation of plates at 30-35° C. Vaginas collected from mice vaccinated with rAls3p-N but not those collected from mice vaccinated with rAls1p-N had lower CFU than vaginas collected from control mice (i.e. mice vaccinated with CFA alone) (FIG. 25, p=0.01 by Wilcoxon Rank Sum test).

In light of the increasing incidence of candidemia and its continuing high mortality rate, development of a vaccine against *Candida* spp. is of great importance. The results described above show that SQ vaccination with rAls1p-N resulted in marked improvement in survival and significant reductions in fungal burden during otherwise rapidly fatal hematogenously disseminated candidiasis in both immunocompetent and immunocompromised mice. Of interest are the kidney fungal burden results from individual vaccinated mice, demonstrating that approximately half the mice had kidney fungal burdens under 5 log CFU/g. We have previously found that the threshold of kidney fungal burden indicative of a fatal infection is 5 log CFU/g; mice with kidney fungal burdens above this level typically die from infection, whereas mice with kidney fungal burdens below this burden survive the infection (Spellberg et al., *J. Infect. Dis.* In press (2005) and (Spellberg et al., *Infect. Immun.* 71:5756-5764 (2003)). Therefore, breakthrough deaths in the vaccinated group likely reflect high fungal burden in spite of vaccination. The mouse to mouse variations in tissue fungal burden may reflect the complexities of host-pathogen interactions and/or variable vaccine responsiveness.

In summary, the rAls1p-N vaccine can be used for the treatment, reduction in severity and/or prevention of increasingly common and highly lethal disseminated candidiasis. The vaccine is efficacious in immunocompetent mice, and efficacy is retained even in neutropenic and corticosteroid-treated hosts. Finally, the vaccine can protect against mucocutaneous candidiasis including vaginal and oropharyngeal candidiasis Example IX Effectiveness of ALS Vaccines Against *S. aureus* Infections This Example shows that Als proteins from *C. albicans* improves survival of animal models infected with *S. aureus*.

Als adhesins of *C. albicans* were identified to be significantly homologous to adhesins on *S. aureus*. This characteristic was used to design and implement an effective vaccine against *S. aureus* using Als adhesins. Briefly, the *C. albicans* ALS family is comprised of at least 9 genes (Hoyer et al., *Genetics* 157:1555-67 (2001); Hoyer LL., *Trends Microbiol.* 9:176-80 (2001)). As described previously, Als proteins function as adhesins to biologically relevant substrates (Fu et al., *Molec. Microbiol.* 44:61-72 (2002); Gaur and Klotz, *Infect. Immun.* 65:5289-94 (1997); Zhao et al., *Microbiology* 150:2415-28 (2004); Oh et al., *Microbiology* 51:673-81 (2005); Zhao et al. *Microbiology* 151:1619-30 (2005)); Hoyer et al., *Mol. Microbiol.* 15:39-54 (1995)). In particular, the N-termini of Als1p and Als3p are significantly homologous to surface proteins expressed by pathogenic *S. aureus*, including collagen binding protein and clumping factor (Table IV; Sheppard et al. *J. Biol. Chem.* 279:30480-89 (2004)).

TABLE IV

Homology of Als proteins to various pathogenic adhesins and invasions

| Protein | Homologue 1 | Homologue 2 |
|---|---|---|
| Als1p | Collagen binding protein of *S. aureus*: ≥95% homology | Clumping factor of *S. aureus*: ≥90% homology |
| Als3p | Collagen binding protein of *S. aureus*: ≥95% homology | Clumping factor of *S. aureus*: ≥80% homology |
| Als5p | Invasin/integrin-binding protein *Y. pseuodtuberculosis* | Surface layer protein *M. mazei* |

The homology calculation provided above in Table TV takes into account both features of sequence alignment and 3-dimensional surface structure. Homology of Als1p was calculated to be greater than 95% or 90% compared to collagen binding protein or clumping factor of *S. aureus* ($r^2 \geq 90\%$; Sheppard et al., supra). Similarly, homology of Als3p was calculated to be greater than 95% or 80% compared to collagen binding protein or clumping factor of *S. aureus* ($r^2 \geq 90\%$).

To corroborate the above findings, homology and threading methods were employed to model structure-function congruence between Als1p and *S. aureus* clumping factor A (ClfA-PDB code: c1n67A). These methods assessed specific homologies in primary structure, 3-D conformation and pattern analyses were conducted to seek analogous functional motifs. For example, BLASTP, PROSITE and JALVIEW methods were employed to analyze similarities and differences in ALS versus ClfA primary sequences (Yount et al. *Antimicrob. Agents Chemother.* 48:4395-4404 (2004) and Yount and Yeaman. *Proc. Natl. Acad. Sci. USA* 101:7363-7368 (2004)). Internet-based applications including 3-D PSSM were then used to prioritize potential ALS homologues for further analysis (Sheppard, et al. *J. Biol. Chem.* 279:30480-30489 (2004)). Along with resulting data, the PHYRE application (Kelley, L., R. Bennett-Lovsey, A. Herbert, and K. Fleming; www.sbg.bio.ic.ac.uk/.about..phyre/) was used to conduct topology mapping and to identify 3-dimensional motifs shared by proteins with greatest structural or functional homology to selected ALS proteins for the purpose of identifying putative shared functional motifs. The above methods are widely available in public domain and used in a variety of proteomic and structural biology applications. Based on the above homology and threading method results a consensus of functional site homologies between Als1p and ClfA was generated and mapped to specific residues of the Als1p model constructed on ClfA. Several particular findings emanated from these modeling analyses as set forth below.

First, significant homology was identified between the N-terminal regions of Asl1p and ClfA in secondary structure and amino acid conservation, particularly in the region encompassed by amino acids 30-300 (i.e. the N-termini of both proteins).

Second, consensus mapping of homologous functional sites based on established ClfA adhesin determinants converged on a specific topological motif in Als1p. This topological motif is shown in FIG. 26 as a cleft formed by the inflection of adjacent facets of two I-sheet domains.

Third, consistent with primary structure homology, the predicted functional cleft motif in Als1p maps to specific residues originating from hypervariable regions in the N-terminal region encompassing amino acid residues 30-300.

These results provided a structural basis for congruent biological functions, as well as immunological responses to Als1p and ClfA. These results also further corroborate our overall model of Als1p structure-activity, and further facilitate targeted approaches to mutational analyses and epitope mapping. Finally, these results indicate that Als1p and ClfA are adhesins of analogous structure and function present on diverse microbial pathogens.

A monoclonal antibody against *S. aureus* also was identified that may reduce infections caused by *C. albicans*. As with the above structural findings, this characteristic also was used to design and implement an effective vaccine against *S. aureus* using Als adhesins.

Briefly, a humanized anti-staphylococcal monoclonal antibody (AUREXIS®) that is known to recognize surface adhesins on *S. aureus* is currently in clinical trials. This monoclonal antibody also cross reacts with Als family members. Favorable results of a phase II clinical trial of AUREXIS® for the treatment of staphylococcal bloodstream infections have been reported (Inhibitex Inc., 2005; phx.corporate-ir.net/phoenix.zhtml?c=176944&p=irol-newsAr-ticle&ID=707322&highlight=). Briefly, in this report, patients with known *S. aureus* in the blood were administered the AUREXIS® antibody as treatment for active infection (i.e., this is not an active vaccine strategy or a prophylaxis study). Nine patients receiving placebo experienced breakthrough bloodstream infections caused by Candida, while only three patients in the AUREXIS® arm experienced Candida bloodstream infections. Recognizing the decrease in Candida blood infection for those patients treated with an antibody to S. aureus combined with the above homology and structural findings indicate that immunogenic epitopes are shared between Candida and S. aureus and that these immunogenic epitopes can be targeted for therapeutic benefit using immune responses, antibodies or effector mechanisms raised against one species for treatment of the other species. Therefore, the above data together provide for immune responses to surface adhesins on S. aureus to cross react with Candida spp.

Following the above strategy, exemplary Als adhesin vaccines were designed and shown to improve survival of mice infected with S. aureus. The exemplary Als adhesins used to vaccinate were rAls1p-N or rAls3p-N, which were produced and used as described above. Briefly, to determine if these Als vaccines against Candida, rAls1p-N and rAls3p-N can mediate cross-species protection against S. aureus, female Balb/c mice were vaccinated with the previously described regimen (Complete Freund's Adjuvant+ 20 µg of rAls1p-N or rAls3p-N on day 0, followed by a booster dose in Incomplete Freund's Adjuvant at 3 weeks, both administered subcutaneously). Two weeks following vaccination, mice were infected via the tail-vein with a lethal dose of S. aureus strain 67-0, which is methicillin-resistant and known to be virulent in animal models. The results showing mice survival are shown in FIG. 26. As indicated, both the rAls1p-N and rAls3p-N vaccines mediated improved long-term survival in these infected mice (FIG. 27). Additionally, the mechanism of protection likely to be an enhancement of Th1 rather than Th2 since no correlation between Ab titers and survival of mice vaccinated with either rAls1p-N or rAls3p-N was observed (FIG. 28).

Example X

The Anti-Candida rAls1p-N Vaccine Mediates a Broad Range of Protection Against Disseminated Candidiasis This Example show that the rAls1p-N vaccine protects outbred mice from disseminated candidiasis, and protects Balb/c mice against other virulent strains of C. albicans and non-albicans Candida.

The current studies were performed to illustrate the breadth of protection induced by rAls1p-N by specifically evaluating its efficacy in outbred mice, in combination with a second adjuvant other than Freund's adjuvant, against other strains of C. albicans, and against non-albicans species of Candida.

Vaccination with rAls1p-N protected outbred mice from disseminated candidiasis. Briefly, outbred CD1 mice were obtained from the National Cancer Institute (Bethesda, Md.). All procedures involving mice were approved by the institutional animal use and care committee, following the National Institutes of Health guidelines for animal housing and care. The mice were vaccinated with rAls1p-N+Freund's adjuvant as previously described above and in, for example, Ibrahim et al., Infect. Immun. 73:999-1005 (2005); Spellberg et al., Infect. Immun. 73:6191-93 (2005). rAls1p-N (amino acids 17 to 432 of Als1p) was produced in S. cerevisiae and purified by gel filtration and Ni-NTA matrix affinity purification. A high degree of purity (≈90%) was confirmed by SDS-polyacrylamide gel electrophoresis as well as circular dichroism and FTIR, as described above and in, for example, Sheppard et al., J Biol Chem 279: 30480-89 (2004). Mice were immunized by SQ injection of rAls1p-N (20 µg) mixed with Complete Freund's Adjuvant (CFA; Sigma-Aldrich, St. Louis, Mo.) at day 0, followed by a booster dose in Incomplete Freund's Adjuvant (IFA; Sigma-Aldrich) at day 21. Control mice were immunized with CFA/IFA alone. Fourteen days following the boost, immunized mice were infected via the tail-vein with C. albicans SC5314, as we have described previously Ibrahim et al., (2005) supra; and Spellberg et al. (2005), supra. Similar to our previous findings in Balb/c mice, the rAls1p-N vaccine markedly improved the survival of infected CD1 mice (FIG. 29A).

Because Freund's adjuvant is considered to be too toxic for use in humans, we performed a dose response of rAls1p-N vaccine in alum (2% ALHYDROGEL®, Brenntag Biosector, Frederikssund, Denmark), the only vaccine adjuvant currently approved by the US Food and Drug Administration (FDA) for use in humans. Vaccination with alum was performed on an identical schedule as Freund's adjuvant, with immunization on day 1, boost on day 21, and infection 2 weeks later. We found that higher doses of rAls1p-N combined with alum resulted in significant improvements in survival of mice with disseminated candidiasis (FIG. 29B). There are also appeared to be a dose response relationship, with trends to improved survival at higher doses of rAls1p-N when combined with alum.

The rAls1p-N vaccine also was shown to improve the survival of Balb/c mice infected with several strains of C. albicans. Particularly useful vaccines utilize an immunogen that can prime the immune system to recognize multiple strains of the target pathogen. By DNA sequence analysis, we found that the predicted amino acid sequence of the N-terminal region of Als1p was 99.9% conserved amongst a diverse group of clinical C. albicans isolates from bloodstream (5 strains), urine (5 strains) and oropharyngeal (10 strains) infections (data not shown). These results indicated that the rAls1p-N vaccine can be effective against a broad array of C. albicans strains. To confirm the breadth of protection of the rAls1p-N vaccine against other strains of C. albicans, mice were vaccinated with rAls1p-N+Freund's adjuvant as above, and infected with one of several clinical isolates of C. albicans (Ibrahim et al., Infect Immun 63:1993-98 (1995)). As shown in FIG. 30, the rAls1p-N vaccine significantly improved the survival of mice infected with each of these strains.

The rAls1p-N vaccine also was shown to reduce tissue fungal burden in mice infected with several non-albicans species of Candida. Briefly, the ALS gene family is present in other Candida species, including C. dubliniensis and C. tropicalis (Hoyer et al., Genetics 157:1555-67 (2001)). Similarly, an adhesin analogous to Als family members has been described in C. glabrata (Cormack et al., Science 285:578-82 (1999); Frieman et al., Mol Microbiol 46:479-92 (2002)). To confirm the efficacy of the rAls1p-N against non-albicans species, Balb/c mice were vaccinated with rAls1p-N+Freund's adjuvant as above, and infected via the tail-vein with C. glabrata 31028 (a clinical bloodstream isolate from the microbiology laboratory at Harbor-UCLA Medical Center), C. krusei 91-1159, (generously provided by Michael Rinaldi, San Antonio, Tex.), C. parapsilosis 22019 (clinical bloodstream isolate from Harbor-UCLA Medical Center), or C. tropicalis 4243 (clinical bloodstream isolate from Harbor-UCLA Medical Center). As shown in FIG. 31, the rAls1p-N vaccine reduced the kidney fungal burden of mice infected with each of these species.

In summary, the rAls1p-N vaccine is able to prevent and/or reduce the severity of an increasingly common and highly lethal disseminated candidiasis. The vaccine is efficacious in both inbred and outbred mice, when mixed with alum as an adjuvant, against multiple strains of *C. albicans*, and against several non-*albicans* species of *Candida*. These results further corroborate that the ALS vaccines of the invention are effective against a wide variety of candidal and other infections.

Example XI

The Anti-*Candida* rAls3p-N Vaccine is Equally Effective as rAls1p-N Against Disseminated and More Efficacious Against Mucosal Candidiasis This Example compares the efficacy of rAls3p-N to rAls1p-N vaccines in murine models of hematogenously disseminated, oropharyngeal, and vaginal candidiasis.

Of the ALS family members, the ALS1 and ALS3 genes encode adhesins with the broadest array of substrate affinity. When compared to one another, Als1p mediated greater adherence to endothelial cells and gelatin, but inferior adherence to epithelial cells (Sheppard et al., *J Biol Chem* 279:30480-89 (2004)). Their differences in adherence qualities suggested that rAls3p-N may have different efficacy as a vaccine immunogen compared to rAls1p-N.

The vaccines and vaccinations were performed as described above. Briefly, rAls1p-N and rAls3p-N (amino acids 17 to 432 of Als1p or Als3p) were produced in *S. cerevisiae* and purified by gel filtration and Ni-NTA matrix affinity purification, as described above and in Ibrahim et al., (2005), supra; Spellberg et al., (2005), supra. The amount of protein was quantified by modified Lowry assay. A high degree of purity ($\approx$90%) was confirmed by SDS-polyacrylamide gel electrophoresis as well as circular dichroism and FTIR, as described above and in Ibrahim et al., (2005), supra; Spellberg et al., (2005), supra. Mice were immunized by subcutaneous (SQ) injection of 20 µg of rAls1p-N or rAls3p-N mixed with Complete Freund's adjuvant (CFA, Sigma-Aldrich, St. Louis, Mo.) at day 0, boosted with another dose of the antigen with Incomplete Freund's adjuvant (IFA, Sigma-Aldrich) at day 21, and infected two weeks following the boost.

Statistical analyses were performed as follows. The nonparametric Log Rank test was utilized to determine differences in survival times of the mice. Antibody titers and footpad swelling were compared by the Steel test for nonparametric multiple comparisons Rhyne et al., *Biometrics* 23:539-49 (1967), or the Mann Whitney U test for unpaired comparisons, as appropriate. Correlations were calculated with the Spearman Rank test. To determine if heterogeneity existed in replicate survival studies, the Kolmogorov-Smirnov test was utilized. P values <0.05 were considered significant.

Vaccination with rAls3p-N was shown to stimulate a broader array of antibody responses in comparison with rAls1p-N. In this regard, the results shown in FIG. 32 show mice vaccinated with CFA+rAls1p-N or rAls3p-N developed antibody titers significantly greater than mice receiving CFA alone. Of note, mice vaccinated with rAls3p-N generated anti-rAls1p-N antibodies at equivalent titers to mice vaccinated with rAls1p-N (FIG. 32, top). In contrast, mice vaccinated with rAls1p-N generated smaller titers against rAls3p-N than did mice vaccinated with rAls3p-N (FIG. 32, bottom). However, both rAls1p-N and rAls3p-N resulted in similar delayed type hypersensitivity responses in vivo as shown in FIG. 33.

The rAls1p-N and rAls3p-N vaccines also were shown to mediate similar efficacy against disseminated candidiasis. Briefly, to further corroborate that the rAls3p-N vaccine was as effective as rAls1p-N against hematogenously disseminated candidiasis, mice were vaccinated with CFA, CFA+rAls1p-N, or CFA+rAls3p-N, and subsequently infected via the tail-vein with *C. albicans*. The results shown in FIG. 34 demonstrate that both the rAls1p-N and rAls3p-N vaccines resulted in significant improvement in survival.

Correlation of anti-Alsp antibody titers and delayed type hypersensitivity reactions with survival in vaccinated mice subsequently infected with *C. albicans* was also determined. Briefly, antibody titers were determined by ELISA in 96 well plates, as we have described previously and in Ibrahim et al., (2005), supra; Spellberg et al., (2005), supra. Wells were coated with 100 µl per well of 5 µg/ml rAls1p-N or rAls3p-N in PBS. Mouse sera were incubated for 1 h at room temperature following a blocking step with tris buffer saline (TBS) (0.01 M TrisHCl, pH 7.4, 0.15 M NaCl) containing 3% bovine serum albumin. The wells were washed 3 times with TBS containing 0.05% TWEEN® 20, followed by another 3 washes with TBS without TWEEN®. Goat anti-mouse IgG secondary antibody conjugated with horseradish peroxidase (Sigma-Aldrich) was added at a final dilution of 1:5000 and the plate was further incubated for 1 h at room temperature. Wells were washed with TBS and incubated with substrate containing 0.1 M citrate buffer (pH 5.0), 50 mg/ml of o-phenylenediamine (Sigma), and 10 µl of 30% $H_2O_2$. The color was allowed to develop for 30 min after which the reaction was terminated by adding 10% $H_2SO_4$ and the optical density (OD) was determined at 490 nm in a microtiter plate reader. Negative control wells received irrelevant antibody, and background absorbance was subtracted from the test wells to obtain final OD readings. The ELISA titer was taken as the reciprocal of the last serum dilution that gave a positive OD reading (i.e. >mean OD of negative control samples+(standard deviation*2)).

Delayed type hypersensitivity reactions were assessed by measuring the footpad swelling tests. Briefly, mice were immunized with rAls1p-N, rAls3p-N, or CFA alone. Two weeks following the boost, baseline footpad sizes of immunized mice were measured using an electronic digital caliper. Fifty µg of rAls1p-N or rAls3p-N in 25 µl of PBS were injected into the right footpads, and PBS alone injected into the left footpads of the immunized mice. Twenty-four hours later the footpads were again measured. Antigen-specific footpad swelling was calculated as: (right footpad thickness at 24 h–right footpad thickness at baseline)–(left footpad thickness at 24 h–left footpad thickness at baseline).

Vaccinated mice were bled for titer determinations and underwent footpad swelling tests two days prior to infection. Vaccinated mice that did not survive the infection nevertheless had a broad range of antibody titers as shown in FIG. 35. Many such mice had anti-rAls1p-N and anti-rAls3p-N antibody titers of $\geq$1:50,000 ($\geq$4.5 $\log_{10}$). As a result, antibody titers did not significantly correlate with survival. In contrast, the intensity of footpad swelling reactions did correlate with survival (FIG. 35, p=0.6 & p=0.009 by Spearman Rank correlation test).

The rAls3p-N vaccine also demonstrated more efficacy than rAls1p-N in two models of mucosal candidiasis. Because Als3p mediated superior adhesion to epithelial cells compared to Als1p, this observation indicates that rAls3p-N can exhibit unique efficacy in mucosal models of infection.

The efficacy of rAls1p-N compared to rAls3p-N assessed in a steroid-treated, oropharyngeal model of infection and in a model of candidal vaginitis.

Briefly, vaccine studies in the above murine oropharyngeal candidiasis (OPC) model were performed as previously described and as described in Spellberg et al., (2005), supra; Kamai et al., Antimicrob Agents Chemother 45:3195-57 (2001), and Kamai et al., Infect Immun 70:5256-58 (2002). Vaccinated mice were immunocompromised by treatment with cortisone acetate (225 mg/kg SQ on days −1, 1, and 3 relative to infection). On the day of infection, the mice were anesthetized by intraperitoneal injection with 8 mg xylazine and 110 mg ketamine per kg. Calcium alginate urethral swabs were saturated with C. albicans by placing them in a suspension of $10^6$ organisms per ml in HBSS at 30° C. The saturated swabs were placed sublingually in the oral cavity of the mice for 75 min. After 5 days of infection, the tongue and hypoglossal tissue were excised, weighed, homogenized, and then quantitatively cultured to determine the oral fungal burden.

Effectiveness of the vaccine against murine vaginal candidiasis was performed by vaccinating female Balb/c mice were treated with 30 µg of subcutaneous estradiol valerate dissolved in peanut oil (both from Sigma-Aldrich) on day −3 relative to infection to induce pseudoestrus. On the day of infection, mice were sedated by ip administration of 100 mg/kg of ketamine. Sedated mice were infected intravaginally with $10^6$ blastospores of C. albicans in 10 µl of HBSS. On day 3 post-infection, vaginas and approximately one centimeter of each uterine horn were dissected en block, homogenized, and quantitatively cultured.

As shown in FIG. 36, in cortisone-treated mice with oropharyngeal candidiasis, the rAls1p-N vaccine mediated a strong trend towards reduced tongue fungal burden (p=0.054). The overall magnitude of the benefit was <0.3 log CFU/gram (FIG. 36). In comparison, the rAls3p-N vaccine mediated a >0.6 log CFU/gram decrease in tongue fungal burden that was statistically significant (p=0.005, FIG. 36). Similarly, in a non-immunocompromised model of candidal vaginitis, the rAls3p-N vaccine mediated a 0.7 log CFU/gram decrease in vaginal fungal burden compared to CFA alone (p=0.02) as shown in FIG. 37. In comparison, rAls1p-N mediated no benefit at all in the vaginitis model, and rAls3p-N was significantly more effective than rAls1p-N (p=0.01).

The above results indicate that a vaccine based on rAls3p-N, which is 85% homologous to rAls1p-N at the amino acid level, was equally effective against disseminated candidiasis, but was more effective than rAls1p-N against mucosal infection. The increased effectiveness of rAls3p-N was seen in both a steroid-treated model of oropharyngeal candidiasis and an immunocompetent model of candidal vaginitis. The above results also show achievement of ≥50% long-term survival in a murine model of candidal septic shock with no adjunctive anti-fungal therapy is encouraging, and further corroborates the therapeutic benefit all ALS vaccines of the invention.

Antibody titers did not correlate with the protective effect of either vaccine during disseminated candidiasis, but induction of delayed type hypersensitivity in vivo did correlate with protection. These data also further corroborate the mechanism of vaccine-induced protection was induction of Type 1, cell-mediated immunity to the fungus. Both rAls1p-N and rAls3p-N induced equivalent titers of antibody against rAls1p-N, but that rAls3p-N induced significantly higher titers of anti-rAls3p-N antibodies than did rAls1p-N. These data indicated that, despite their high degree of amino acid sequence homology (85%), the humoral immune system can distinguish between rAls1p-N and rAls3p-N. The above results further corroborate that, regardless of differences in Als1p and Als3p epithelial cell adherence characteristics, the rAls1p-N and rAls3p-N vaccines were equally effective in protecting against hematogenously disseminated (i.e. endovascular) candidiasis.

In sum, the anti-candidal rAls3p-N vaccine induced equivalent cell-mediated but broader antibody-based responses than did the rAls1p-N vaccine. The immunogens resulted in an equivalent degree of protection against hematogenously disseminated candidiasis, but rAls3p-N mediated greater protection against both oropharyngeal and vaginal candidiasis.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A method of treating a human having, or at risk of acquiring, community-acquired *Staphylococcus aureus* infection comprising administering to the human an immunogenic composition comprising an isolated polypeptide consisting of an N-terminal domain of *Candida albicans* agglutinin-like sequence 3 protein (Als3p), wherein the N-terminal domain extends from the end of the signal peptide to the beginning of the tandem repeats of the *Candida albicans* Als3p, in a pharmaceutically acceptable medium, wherein the polypeptide elicits an immune response in said human that treats the infection.

2. The method of claim 1, wherein the immunogenic composition is administered by intravenous, intramuscular, intraperitoneal, or subcutaneous injection.

3. The method of claim 2, wherein the immunogenic composition is administered by subcutaneous injection.

4. The method of claim 1, wherein the immunogenic composition further comprises an adjuvant.

5. The method of claim 4, wherein said adjuvant is alum.

6. The method of claim 1, wherein the isolated polypeptide is produced in *Saccharomyces cerevisiae*.

7. The method of claim 1, wherein the isolated polypeptide consists of the N-terminal domain of the Als3p having the amino acid sequence set forth in SEQ ID NO: 2.

8. The method of claim 1, wherein the isolated polypeptide is substantially pure.

9. The method of claim 1, wherein said *S. aureus* is beta-lactam resistant.

* * * * *

SEQUENCE LISTING

<160> NUMBER OF SEQ ID NOS: 25

<210> SEQ ID NO 1
<211> LENGTH: 534
<212> TYPE: PRT
<213> ORGANISM: Candida albicans

<400> SEQUENCE: 1

Met Leu Gln Gln Phe Thr Leu Leu Phe Leu Tyr Leu Ser Ile Ala Ser
1               5                   10                  15

Ala Lys Thr Ile Thr Gly Val Phe Asp Ser Phe Asn Ser Leu Thr Trp
            20                  25                  30

Ser Asn Ala Ala Asn Tyr Ala Phe Lys Gly Pro Gly Tyr Pro Thr Trp
        35                  40                  45

Asn Ala Val Leu Gly Trp Ser Leu Asp Gly Thr Ser Ala Asn Pro Gly

```
             50                  55                  60
Asp Thr Phe Thr Leu Asn Met Pro Cys Val Phe Lys Tyr Thr Thr Ser
 65                  70                  75                  80

Gln Thr Ser Val Asp Leu Thr Ala Asp Gly Val Lys Tyr Ala Thr Cys
                 85                  90                  95

Gln Phe Tyr Ser Gly Glu Glu Phe Thr Thr Phe Ser Thr Leu Thr Cys
                    100                 105                 110

Thr Val Asn Asp Ala Leu Lys Ser Ser Ile Lys Ala Phe Gly Thr Val
                115                 120                 125

Thr Leu Pro Ile Ala Phe Asn Val Gly Gly Thr Gly Ser Ser Thr Asp
            130                 135                 140

Leu Glu Asp Ser Lys Cys Phe Thr Ala Gly Thr Asn Thr Val Thr Phe
145                 150                 155                 160

Asn Asp Gly Asp Lys Asp Ile Ser Ile Asp Val Glu Phe Glu Lys Ser
                165                 170                 175

Thr Val Asp Pro Ser Ala Tyr Leu Tyr Ala Ser Arg Val Met Pro Ser
                180                 185                 190

Leu Asn Lys Val Thr Thr Leu Phe Val Ala Pro Gln Cys Glu Asn Gly
            195                 200                 205

Tyr Thr Ser Gly Thr Met Gly Phe Ser Ser Ser Asn Gly Asp Val Ala
            210                 215                 220

Ile Asp Cys Ser Asn Ile His Ile Gly Ile Thr Lys Gly Leu Asn Asp
225                 230                 235                 240

Trp Asn Tyr Pro Val Ser Ser Glu Ser Phe Ser Tyr Thr Lys Thr Cys
                245                 250                 255

Thr Ser Asn Gly Ile Gln Ile Lys Tyr Gln Asn Val Pro Ala Gly Tyr
                260                 265                 270

Arg Pro Phe Ile Asp Ala Tyr Ile Ser Ala Thr Asp Val Asn Gln Tyr
            275                 280                 285

Thr Leu Ala Tyr Thr Asn Asp Tyr Thr Cys Ala Gly Ser Arg Ser Gln
            290                 295                 300

Ser Lys Pro Phe Thr Leu Arg Trp Thr Gly Tyr Lys Asn Ser Asp Ala
305                 310                 315                 320

Gly Ser Asn Gly Ile Val Ile Val Ala Thr Thr Arg Thr Val Thr Asp
                325                 330                 335

Ser Thr Thr Ala Val Thr Thr Leu Pro Phe Asn Pro Ser Val Asp Lys
            340                 345                 350

Thr Lys Thr Ile Glu Ile Leu Gln Pro Ile Pro Thr Thr Thr Ile Thr
            355                 360                 365

Thr Ser Tyr Val Gly Val Thr Thr Ser Tyr Leu Thr Lys Thr Ala Pro
370                 375                 380

Ile Gly Glu Thr Ala Thr Val Ile Val Asp Pro Tyr His Thr Thr
385                 390                 395                 400

Thr Thr Val Thr Ser Glu Trp Thr Gly Thr Ile Thr Thr Thr Thr Thr
                405                 410                 415

Arg Thr Asn Pro Thr Asp Ser Ile Asp Thr Val Val Gln Val Pro
                420                 425                 430

Ser Pro Asn Pro Thr Val Ser Thr Glu Tyr Trp Ser Gln Ser Phe
            435                 440                 445

Ala Thr Thr Thr Thr Val Thr Ala Pro Pro Gly Gly Thr Asp Thr Val
            450                 455                 460

Ile Ile Arg Glu Pro Pro Asn His Thr Val Thr Thr Glu Tyr Trp
465                 470                 475                 480
```

```
Ser Gln Ser Phe Ala Thr Thr Thr Val Thr Ala Pro Pro Gly Gly
                485                 490                 495

Thr Asp Ser Val Ile Ile Arg Glu Pro Pro Asn Pro Val Thr Thr
            500                 505                 510

Thr Glu Tyr Trp Ser Gln Ser Phe Ala Thr Thr Thr Val Thr Ala
        515                 520                 525

Pro Pro Gly Gly Thr Asp
    530

<210> SEQ ID NO 2
<211> LENGTH: 534
<212> TYPE: PRT
<213> ORGANISM: Candida albicans

<400> SEQUENCE: 2

Met Leu Gln Gln Tyr Thr Leu Leu Ile Tyr Leu Ser Val Ala Thr
1               5                   10                  15

Ala Lys Thr Ile Thr Gly Val Phe Asn Ser Phe Asn Ser Leu Thr Trp
            20                  25                  30

Ser Asn Ala Ala Thr Tyr Asn Tyr Lys Gly Pro Gly Thr Pro Thr Trp
        35                  40                  45

Asn Ala Val Leu Gly Trp Ser Leu Asp Gly Thr Ser Ala Ser Pro Gly
    50                  55                  60

Asp Thr Phe Thr Leu Asn Met Pro Cys Val Phe Lys Phe Thr Thr Ser
65                  70                  75                  80

Gln Thr Ser Val Asp Leu Thr Ala His Gly Val Lys Tyr Ala Thr Cys
                85                  90                  95

Gln Phe Gln Ala Gly Glu Glu Phe Met Thr Phe Ser Thr Leu Thr Cys
            100                 105                 110

Thr Val Ser Asn Thr Leu Thr Pro Ser Ile Lys Ala Leu Gly Thr Val
        115                 120                 125

Thr Leu Pro Leu Ala Phe Asn Val Gly Thr Gly Ser Ser Val Asp
    130                 135                 140

Leu Glu Asp Ser Lys Cys Phe Thr Ala Gly Thr Asn Thr Val Thr Phe
145                 150                 155                 160

Asn Asp Gly Gly Lys Lys Ile Ser Ile Asn Val Asp Phe Glu Arg Ser
                165                 170                 175

Asn Val Asp Pro Lys Gly Tyr Leu Thr Asp Ser Arg Val Ile Pro Ser
            180                 185                 190

Leu Asn Lys Val Ser Thr Leu Phe Val Ala Pro Gln Cys Ala Asn Gly
        195                 200                 205

Tyr Thr Ser Gly Thr Met Gly Phe Ala Asn Thr Tyr Gly Asp Val Gln
    210                 215                 220

Ile Asp Cys Ser Asn Ile His Val Gly Ile Thr Lys Gly Leu Asn Asp
225                 230                 235                 240

Trp Asn Tyr Pro Val Ser Ser Glu Ser Phe Ser Tyr Thr Lys Thr Cys
                245                 250                 255

Ser Ser Asn Gly Ile Phe Ile Thr Tyr Lys Asn Val Pro Ala Gly Tyr
            260                 265                 270

Arg Pro Phe Val Asp Ala Tyr Ile Ser Ala Thr Asp Val Asn Ser Tyr
        275                 280                 285

Thr Leu Ser Tyr Ala Asn Glu Tyr Thr Cys Ala Gly Gly Tyr Trp Gln
    290                 295                 300

Arg Ala Pro Phe Thr Leu Arg Trp Thr Gly Tyr Arg Asn Ser Asp Ala
```

```
                305                 310                 315                 320
Gly Ser Asn Gly Ile Val Ile Val Ala Thr Thr Arg Thr Val Thr Asp
            325                 330                 335

Ser Thr Thr Ala Val Thr Thr Leu Pro Phe Asp Pro Asn Arg Asp Lys
            340                 345                 350

Thr Lys Thr Ile Glu Ile Leu Lys Pro Ile Pro Thr Thr Thr Ile Thr
            355                 360                 365

Thr Ser Tyr Val Gly Val Thr Thr Ser Tyr Leu Thr Lys Thr Ala Pro
            370                 375                 380

Ile Gly Glu Thr Ala Thr Val Ile Val Asp Ile Pro Tyr His Thr Thr
385                 390                 395                 400

Thr Thr Val Thr Ser Lys Trp Thr Gly Thr Ile Thr Ser Thr Thr Thr
                405                 410                 415

His Thr Asn Pro Thr Asp Ser Ile Asp Thr Val Ile Val Gln Val Pro
                420                 425                 430

Ser Pro Asn Pro Thr Val Thr Thr Thr Glu Tyr Trp Ser Gln Ser Phe
            435                 440                 445

Ala Thr Thr Thr Thr Ile Thr Gly Pro Pro Gly Asn Thr Asp Thr Val
            450                 455                 460

Leu Ile Arg Glu Pro Pro Asn His Thr Val Thr Thr Thr Glu Tyr Trp
465                 470                 475                 480

Ser Glu Ser Tyr Thr Thr Thr Ser Thr Phe Ala Pro Pro Gly Gly
                485                 490                 495

Thr Asp Ser Val Ile Ile Lys Glu Pro Pro Asn Pro Thr Val Thr Thr
                500                 505                 510

Thr Glu Tyr Trp Ser Glu Ser Tyr Thr Thr Thr Ser Thr Phe Thr Ala
                515                 520                 525

Pro Pro Gly Gly Thr Asp
            530

<210> SEQ ID NO 3
<211> LENGTH: 534
<212> TYPE: PRT
<213> ORGANISM: Candida albicans

<400> SEQUENCE: 3

Met Ile Gln Gln Phe Thr Leu Leu Phe Leu Tyr Leu Ser Phe Ala Thr
1               5                   10                  15

Ala Lys Ala Ile Thr Gly Ile Phe Asn Ser Ile Asp Ser Leu Thr Tyr
            20                  25                  30

Ser Asn Ala Gly Asn Tyr Ala Phe Lys Gly Pro Gly Tyr Pro Thr Tyr
        35                  40                  45

Asn Ala Val Leu Gly Trp Ser Leu Asp Gly Thr Ser Ala Asn Pro Gly
    50                  55                  60

Asp Thr Phe Ile Leu Asn Met Pro Cys Val Phe Lys Phe Thr Ala Ser
65                  70                  75                  80

Gln Lys Ser Val Asp Leu Thr Ala Asp Gly Val Lys Tyr Ala Thr Cys
                85                  90                  95

Gln Phe Tyr Ser Gly Glu Glu Phe Thr Thr Phe Ser Thr Leu Thr Cys
            100                 105                 110

Thr Val Asn Asp Ala Leu Lys Ser Ser Ile Lys Ala Phe Gly Thr Val
            115                 120                 125

Thr Leu Pro Ile Ala Phe Asn Val Gly Gly Thr Gly Ser Ser Thr Asp
            130                 135                 140
```

-continued

Leu Glu Asp Ser Lys Cys Phe Thr Ala Gly Ile Asn Thr Val Thr Phe
145                 150                 155                 160

Asn Asp Gly Ser Lys Lys Leu Ser Ile Ala Val Asn Phe Glu Lys Ser
            165                 170                 175

Thr Val Asp Arg Ser Gly Tyr Leu Thr Thr Ser Arg Phe Met Pro Ser
        180                 185                 190

Leu Asn Lys Ile Ala Thr Leu Tyr Val Ala Pro Gln Cys Glu Asn Gly
    195                 200                 205

Tyr Thr Ser Gly Thr Met Gly Phe Ser Thr Ser Tyr Gly Asp Val Ala
        210                 215                 220

Ile Asp Cys Ser Asn Val His Ile Gly Ile Ser Lys Gly Val Asn Asp
225                 230                 235                 240

Trp Asn His Pro Val Thr Ser Glu Ser Phe Ser Tyr Thr Lys Ser Cys
                245                 250                 255

Ser Ser Phe Gly Ile Ser Ile Thr Tyr Gln Asn Val Pro Ala Gly Tyr
            260                 265                 270

Arg Pro Phe Ile Asp Ala Tyr Ile Ser Pro Ser Asp Asn Asn Gln Tyr
        275                 280                 285

Gln Leu Ser Tyr Lys Asn Asp Tyr Thr Cys Val Asp Asp Tyr Trp Gln
    290                 295                 300

His Ala Pro Phe Thr Leu Lys Trp Thr Gly Tyr Lys Asn Ser Asp Ala
305                 310                 315                 320

Gly Ser Asn Gly Ile Val Ile Val Ala Thr Thr Arg Thr Val Thr Asp
                325                 330                 335

Ser Thr Thr Ala Val Thr Thr Leu Pro Phe Asn Pro Ser Val Asp Lys
            340                 345                 350

Thr Lys Thr Ile Glu Ile Leu Gln Pro Ile Pro Thr Thr Thr Ile Thr
        355                 360                 365

Thr Ser Tyr Val Gly Val Thr Thr Ser Tyr Leu Thr Lys Thr Ala Pro
    370                 375                 380

Ile Gly Glu Thr Ala Thr Leu Ile Val Asp Val Pro Tyr His Thr Thr
385                 390                 395                 400

Thr Thr Val Thr Ser Glu Trp Ile Gly Thr Thr Thr Thr Thr Thr Thr
                405                 410                 415

Arg Thr Asn Pro Thr Asp Ser Ile Asp Thr Val Val Gln Val Pro
            420                 425                 430

Leu Pro Asn Pro Thr Thr Thr Thr Gln Phe Trp Ser Glu Ser Phe
        435                 440                 445

Thr Ser Thr Thr Thr Ile Thr Asn Ser Leu Lys Gly Thr Asp Ser Val
    450                 455                 460

Ile Val Arg Glu Pro His Asn Pro Thr Val Thr Thr Glu Phe Ser
465                 470                 475                 480

Ser Glu Ser Phe Ala Thr Thr Glu Thr Ile Thr Ser Lys Pro Glu Gly
                485                 490                 495

Thr Asp Ser Val Ile Val Arg Glu Pro His Asn Pro Thr Val Thr Thr
            500                 505                 510

Thr Glu Phe Trp Ser Glu Ser Tyr Ala Thr Thr Glu Thr Ile Thr Asn
        515                 520                 525

Gly Pro Glu Gly Thr Asp
    530

<210> SEQ ID NO 4
<211> LENGTH: 537
<212> TYPE: PRT

<213> ORGANISM: Candida albicans

<400> SEQUENCE: 4

```
Met Lys Thr Val Ile Leu Leu His Leu Phe Phe Tyr Cys Thr Ile Ala
1               5                   10                  15

Met Ala Lys Thr Ile Ser Gly Val Phe Thr Ser Phe Asn Ser Leu Thr
            20                  25                  30

Tyr Thr Asn Thr Gly Asn Tyr Pro Tyr Gly Gly Pro Gly Tyr Pro Thr
        35                  40                  45

Tyr Thr Ala Val Leu Gly Trp Ser Leu Asp Gly Thr Leu Ala Ser Pro
    50                  55                  60

Gly Asp Thr Phe Thr Leu Val Met Pro Cys Val Phe Lys Phe Ile Thr
65                  70                  75                  80

Thr Gln Thr Ser Val Asp Leu Thr Ala Asn Gly Val Lys Tyr Ala Thr
                85                  90                  95

Cys Thr Phe His Ala Gly Glu Asp Phe Thr Thr Phe Ser Ser Met Ser
            100                 105                 110

Cys Val Val Asn Asn Gly Leu Ser Ser Asn Ile Arg Ala Phe Gly Thr
        115                 120                 125

Val Arg Leu Pro Ile Ser Phe Asn Val Gly Thr Gly Ser Ser Val
    130                 135                 140

Asn Ile Gln Asp Ser Lys Cys Phe Thr Ala Gly Thr Asn Thr Val Thr
145                 150                 155                 160

Phe Thr Asp Gly Asp His Lys Ile Ser Thr Thr Val Asn Phe Pro Lys
                165                 170                 175

Thr Pro Gln Ser Ser Ser Ser Leu Val Tyr Phe Ala Arg Val Ile Pro
            180                 185                 190

Ser Leu Asp Lys Leu Ser Ser Leu Val Val Ala Ser Gln Cys Thr Ala
        195                 200                 205

Gly Tyr Ala Ser Gly Val Leu Gly Phe Ser Ala Thr Lys Asp Asp Val
    210                 215                 220

Thr Ile Asp Cys Ser Thr Ile His Val Gly Ile Thr Asn Gly Leu Asn
225                 230                 235                 240

Ser Trp Asn Met Pro Val Ser Ser Glu Ser Phe Ser Tyr Thr Lys Thr
                245                 250                 255

Cys Thr Pro Asn Ser Phe Ile Ile Thr Tyr Glu Asn Val Pro Ala Gly
            260                 265                 270

Tyr Arg Pro Phe Ile Asp Ser Tyr Val Lys Ser Ala Thr Ala Thr
        275                 280                 285

Asn Gly Phe Asn Leu Asn Tyr Thr Asn Ile Tyr Asn Cys Met Asp Gly
    290                 295                 300

Lys Lys Gly Asn Asp Pro Leu Ile Tyr Phe Trp Thr Ser Tyr Thr Asn
305                 310                 315                 320

Ser Asp Ala Gly Ser Asn Gly Ala Ala Val Val Thr Thr Arg Thr
                325                 330                 335

Val Thr Asp Ser Thr Thr Ala Ile Thr Thr Leu Pro Phe Asp Pro Thr
            340                 345                 350

Val Asp Lys Thr Lys Thr Ile Glu Val Ile Glu Pro Ile Pro Thr Thr
        355                 360                 365

Thr Ile Thr Thr Ser Tyr Val Gly Ile Ser Thr Ser Leu Ser Thr Lys
    370                 375                 380

Thr Ala Thr Ile Gly Gly Thr Ala Thr Val Val Val Asp Val Pro Tyr
385                 390                 395                 400
```

His Thr Thr Thr Thr Ile Thr Ser Ile Tyr Thr Gly Ser Ala Thr Thr
                405                 410                 415

Ser Ser Thr Tyr Thr Asn Pro Thr Asp Ser Ile Asp Thr Val Val Val
            420                 425                 430

Gln Val Pro Ser Pro Asn Pro Thr Val Thr Thr Gln Phe Trp Ser
        435                 440                 445

Gly Ser Val Pro Thr Thr Glu Thr Val Thr Thr Gly Pro Gln Gly Thr
450                 455                 460

Asp Ser Val Ile Ile Lys Glu Pro His Asn Pro Thr Val Thr Thr Thr
465                 470                 475                 480

Glu Phe Ser Ser Glu Ser Phe Ala Thr Thr Glu Thr Val Thr Asn Gly
                485                 490                 495

Pro Glu Gly Thr Asp Ser Val Ile Val Arg Glu Pro His Asn Pro Thr
            500                 505                 510

Val Thr Thr Thr Glu Phe Trp Ser Glu Ser Phe Ala Thr Thr Glu Thr
        515                 520                 525

Val Thr Asn Gly Pro Glu Gly Thr Asp
    530                 535

<210> SEQ ID NO 5
<211> LENGTH: 536
<212> TYPE: PRT
<213> ORGANISM: Candida albicans

<400> SEQUENCE: 5

Met Lys Lys Leu Tyr Leu Leu Tyr Leu Leu Ala Ser Phe Thr Thr Val
1               5                   10                  15

Ile Ser Lys Glu Val Thr Gly Val Phe Asn Gln Phe Asn Ser Leu Ile
            20                  25                  30

Trp Ser Tyr Thr Tyr Arg Ala Arg Tyr Glu Glu Ile Ser Thr Leu Thr
        35                  40                  45

Ala Lys Ala Gln Leu Glu Trp Ala Leu Asp Gly Thr Ile Ala Ser Pro
    50                  55                  60

Gly Asp Thr Phe Thr Leu Val Met Pro Cys Val Tyr Lys Phe Met Thr
65                  70                  75                  80

Tyr Glu Thr Ser Val Gln Leu Thr Ala Asn Ser Ile Ala Tyr Ala Thr
                85                  90                  95

Cys Asp Phe Asp Ala Gly Glu Thr Lys Ser Phe Ser Ser Leu Lys
            100                 105                 110

Cys Thr Val Thr Asp Glu Leu Thr Glu Asp Thr Ser Val Phe Gly Ser
        115                 120                 125

Val Ile Leu Pro Ile Ala Phe Asn Val Gly Gly Ser Gly Lys Ser
130                 135                 140

Thr Ile Thr Asp Ser Lys Cys Phe Ser Ser Gly Tyr Asn Thr Val Thr
145                 150                 155                 160

Phe Phe Asp Gly Asn Asn Gln Leu Ser Thr Thr Ala Asn Phe Leu Pro
                165                 170                 175

Arg Arg Glu Leu Ala Phe Gly Leu Val Val Ser Gln Arg Leu Ser Met
            180                 185                 190

Ser Leu Asp Thr Met Thr Asn Phe Val Met Ser Thr Pro Cys Phe Met
        195                 200                 205

Gly Tyr Gln Ser Gly Lys Leu Gly Phe Thr Ser Asn Asp Asp Phe
210                 215                 220

Glu Ile Asp Cys Ser Ser Ile His Val Gly Ile Thr Asn Glu Ile Asn
225                 230                 235                 240

-continued

```
Asp Trp Ser Met Pro Val Ser Val Pro Phe Asp His Thr Ile Arg
            245                 250                 255

Cys Thr Ser Arg Ala Leu Tyr Ile Glu Phe Lys Thr Ile Pro Ala Gly
        260                 265                 270

Tyr Arg Pro Phe Val Asp Ala Ile Val Gln Ile Pro Thr Thr Glu Pro
    275                 280                 285

Phe Phe Val Lys Tyr Thr Asn Glu Phe Ala Cys Val Asn Gly Ile Tyr
290                 295                 300

Thr Ser Ile Pro Phe Thr Ser Phe Ser Gln Pro Ile Leu Tyr Asp
305                 310                 315                 320

Glu Ala Leu Ala Ile Gly Ala Asp Leu Val Arg Thr Thr Ser Thr Val
                325                 330                 335

Ile Gly Ser Ile Thr Arg Thr Thr Thr Leu Pro Phe Ile Ser Arg Leu
            340                 345                 350

Gln Lys Thr Lys Thr Ile Leu Val Leu Glu Pro Ile Pro Thr Thr Thr
        355                 360                 365

Val Thr Thr Ser His His Gly Phe Asp Thr Trp Tyr Tyr Thr Lys Lys
    370                 375                 380

Ala Thr Ile Gly Asp Thr Ala Thr Val Phe Ile Asp Val Pro Gln His
385                 390                 395                 400

Thr Ala Thr Thr Leu Thr Thr Tyr Tyr Gln Glu Ser Ser Thr Ala Thr
                405                 410                 415

Thr Thr Tyr Phe Asp Asp Ile Asp Leu Val Asp Thr Ile Val Lys
            420                 425                 430

Ile Pro Tyr Pro Asn Pro Thr Val Ile Thr Thr Lys Phe Trp Ser Glu
        435                 440                 445

Ser Phe Ala Thr Thr Glu Thr Val Thr Asn Gly Pro Glu Gly Thr Asp
    450                 455                 460

Gly Val Ile Ile Lys Glu Pro His Asn Pro Thr Val Thr Thr Thr Lys
465                 470                 475                 480

Phe Ser Ser Glu Ser Phe Ala Thr Thr Glu Thr Val Thr Asn Gly Pro
                485                 490                 495

Glu Gly Thr Asp Ser Val Ile Ile Lys Glu Pro His Asn Pro Thr Val
            500                 505                 510

Thr Thr Thr Lys Phe Trp Ser Glu Ser Phe Ala Thr Thr Glu Thr Val
        515                 520                 525

Thr Asn Gly Pro Glu Gly Thr Asp
    530                 535

<210> SEQ ID NO 6
<211> LENGTH: 532
<212> TYPE: PRT
<213> ORGANISM: Candida albicans

<400> SEQUENCE: 6

Met Leu Pro Gln Phe Leu Leu Leu Leu Tyr Leu Thr Val Ser Thr
1               5                   10                  15

Ala Lys Thr Ile Thr Gly Val Phe Asn Ser Phe Asn Ser Leu Thr Trp
            20                  25                  30

Ala Asn Ala Ala Asn Tyr Gly Tyr Gln Ile Pro Glu Thr Pro Thr Trp
        35                  40                  45

Thr Ala Val Leu Gly Trp Ser Leu Asn Ser Thr Ala Asp Ala Gly
    50                  55                  60

Asp Thr Phe Thr Leu Ile Met Pro Cys Val Phe Lys Phe Ile Thr Ser
```

-continued

```
             65                  70                  75                  80
        Gln Thr Ser Val Asp Leu Thr Ala Asp Gly Val Ser Tyr Ala Thr Cys
                         85                  90                  95

Asp Phe Asn Ala Gly Glu Glu Phe Thr Thr Phe Ser Ser Leu Ser Cys
                        100                 105                 110

Thr Val Asn Ser Val Ser Val Ser Tyr Asp Lys Ala Ser Gly Thr Val
                        115                 120                 125

Lys Leu Pro Phe Ser Phe Asn Val Gly Gly Thr Gly Ser Ser Val Asp
                130                 135                 140

Leu Thr Asp Ser Lys Cys Phe Thr Ala Gly Lys Asn Thr Val Thr Phe
        145                 150                 155                 160

Thr Asp Gly Asp Thr Glu Ile Ser Thr Ser Val Asp Phe Gln Ala Ser
                        165                 170                 175

Pro Ile Ser Ser Ser Gly Tyr Ile Ala Ser Ala Arg Val Val Pro Ser
                        180                 185                 190

Leu Asn Lys Ala Ser Ser Leu Phe Val Leu Pro Gln Cys Glu Asn Gly
                        195                 200                 205

Tyr Thr Ser Gly Ile Met Gly Phe Val Thr Ser Gln Gly Ala Thr Ile
                210                 215                 220

Asp Cys Ser Asn Ile Asn Ile Gly Ile Ser Lys Gly Leu Asn Asp Trp
        225                 230                 235                 240

Asn Phe Pro Val Ser Ser Glu Ser Phe Thr Tyr Thr Lys Thr Cys Ser
                        245                 250                 255

Ser Ser Gly Ile Ile Val Glu Tyr Glu Asn Val Pro Ala Gly Tyr Arg
                        260                 265                 270

Pro Phe Val Asp Ala Tyr Ile Ser Ser Glu Asn Val Glu Gln Tyr Thr
                        275                 280                 285

Leu Thr Tyr Ala Asn Glu Tyr Thr Cys Lys Asn Gly Asn Thr Val Val
                        290                 295                 300

Asp Pro Phe Thr Leu Thr Trp Ile Gly Tyr Lys Asn Ser Glu Ala Asp
        305                 310                 315                 320

Ser Asn Gly Asp Ile Ile Val Val Thr Thr Lys Thr Val Thr Ala Ser
                        325                 330                 335

Thr Thr Ala Val Thr Thr Leu Pro Phe Asn Pro Thr Val Asp Lys Thr
                        340                 345                 350

Glu Thr Ile Glu Val Ile Gln Pro Ile Pro Thr Thr Thr Thr Thr Thr
                        355                 360                 365

Ser Tyr Val Gly Val Thr Thr Ser Tyr Glu Thr Phe Thr Ala Thr Ile
                370                 375                 380

Gly Gly Thr Ala Thr Val Ile Val Asp Thr Pro Tyr His Ile Thr Thr
        385                 390                 395                 400

Thr Val Thr Thr Phe Trp Ile Gly Ser Val Thr Thr Thr Thr Thr Tyr
                        405                 410                 415

Ser Asn Pro Thr Gly Ser Val Asp Thr Val Ile Val Glu Leu Pro Leu
                        420                 425                 430

Pro Ala Pro Thr Val Thr His Glu Phe Trp Ser Glu Ser Phe Ala Ser
                        435                 440                 445

Thr Thr Thr Val Thr Asn Pro Pro Asp Gly Thr Asn Ser Val Ile Ile
                        450                 455                 460

Lys Glu Pro Tyr Asn Pro Thr Val Thr Thr Glu Phe Ser Ser Glu
        465                 470                 475                 480

Ser Phe Ala Ser Thr Thr Thr Val Thr Asn Pro Pro Asp Gly Thr Asn
                        485                 490                 495
```

Ser Val Ile Val Lys Glu Pro Tyr Asn Pro Thr Val Thr Thr Glu
            500                 505                 510

Phe Trp Ser Glu Ser Phe Ala Ser Thr Thr Val Thr Asn Pro Pro
        515                 520                 525

Asp Gly Thr Asn
        530

<210> SEQ ID NO 7
<211> LENGTH: 201
<212> TYPE: PRT
<213> ORGANISM: Candida albicans

<400> SEQUENCE: 7

Leu Lys Gly Phe Ser Leu Thr Ala Leu Trp Leu Thr Ala Gly Asp Thr
1               5                   10                  15

Phe Leu Met Pro Cys Val Lys Ser Val Leu Thr Ala Tyr Ala Thr Cys
            20                  25                  30

Phe Gly Glu Phe Ser Cys Val Gly Val Leu Pro Phe Asn Val Gly Gly
        35                  40                  45

Gly Ser Asp Ser Lys Cys Phe Gly Asn Thr Val Thr Phe Asp Gly Ser
    50                  55                  60

Phe Arg Ser Leu Cys Gly Tyr Ser Gly Gly Phe Ile Asp Cys Ser Gly
65                  70                  75                  80

Ile Asn Trp Pro Val Ser Phe Thr Cys Pro Ala Gly Tyr Arg Pro Phe
                85                  90                  95

Asp Tyr Asn Cys Pro Ala Gly Val Thr Thr Val Ser Thr Thr Thr
            100                 105                 110

Leu Pro Phe Lys Thr Thr Ile Pro Ile Pro Thr Thr Thr Thr Ser
        115                 120                 125

Gly Thr Thr Ala Ile Gly Thr Ala Thr Val Asp Pro His Thr Thr Thr
    130                 135                 140

Trp Thr Thr Asp Thr Val Val Pro Pro Thr Trp Ser Ser Thr Thr
145                 150                 155                 160

Thr Thr Val Glu Pro Asn Thr Val Thr Thr Trp Ser Ser Thr Thr
                165                 170                 175

Thr Pro Gly Thr Ser Val Ile Glu Pro Asn Pro Thr Val Thr Thr Thr
            180                 185                 190

Trp Ser Ser Thr Thr Thr Pro Gly Thr
        195                 200

<210> SEQ ID NO 8
<211> LENGTH: 32
<212> TYPE: DNA
<213> ORGANISM: Artificial Sequence
<220> FEATURE:
<223> OTHER INFORMATION: synthetic primer

<400> SEQUENCE: 8
ccctcgagat gcttcaacaa tttacattgt ta                                32

<210> SEQ ID NO 9
<211> LENGTH: 32
<212> TYPE: DNA
<213> ORGANISM: Artificial Sequence
<220> FEATURE:
<223> OTHER INFORMATION: synthetic primer

<400> SEQUENCE: 9
ccgctcgagt cactaaatga acaaggacaa ta                                    32

<210> SEQ ID NO 10
<211> LENGTH: 31
<212> TYPE: DNA
<213> ORGANISM: Artificial Sequence
<220> FEATURE:
<223> OTHER INFORMATION: synthetic primer

<400> SEQUENCE: 10
cgggatccag atgcttcaac aatttacatt g                                     31

<210> SEQ ID NO 11
<211> LENGTH: 30
<212> TYPE: DNA
<213> ORGANISM: Artificial Sequence
<220> FEATURE:
<223> OTHER INFORMATION: synthetic primer

<400> SEQUENCE: 11
cgggatcctc actaatgaac aaggacaata                                       30

<210> SEQ ID NO 12
<211> LENGTH: 19
<212> TYPE: DNA
<213> ORGANISM: Artificial Sequence
<220> FEATURE:
<223> OTHER INFORMATION: synthetic primer

<400> SEQUENCE: 12
ccgtttatac catccaatc                                                   19

<210> SEQ ID NO 13
<211> LENGTH: 22
<212> TYPE: DNA
<213> ORGANISM: Artificial Sequence
<220> FEATURE:
<223> OTHER INFORMATION: synthetic primer

<400> SEQUENCE: 13
ctacatcctc caatgatata ac                                               22

<210> SEQ ID NO 14
<211> LENGTH: 30
<212> TYPE: DNA
<213> ORGANISM: Artificial Sequence
<220> FEATURE:
<223> OTHER INFORMATION: synthetic primer

<400> SEQUENCE: 14
agatctcaga tgcttcaaca atttacattg                                       30

<210> SEQ ID NO 15
<211> LENGTH: 35
<212> TYPE: DNA
<213> ORGANISM: Artificial Sequence
<220> FEATURE:
<223> OTHER INFORMATION: synthetic primer

<400> SEQUENCE: 15
gaagatctat gctacaacaa tatacattgt tactc                                 35

<210> SEQ ID NO 16
<211> LENGTH: 25
<212> TYPE: DNA
<213> ORGANISM: Artificial Sequence

```
<220> FEATURE:
<223> OTHER INFORMATION: synthetic primer

<400> SEQUENCE: 16
agatctcaac taccaactgc taaca                                           25

<210> SEQ ID NO 17
<211> LENGTH: 27
<212> TYPE: DNA
<213> ORGANISM: Artificial Sequence
<220> FEATURE:
<223> OTHER INFORMATION: synthetic primer

<400> SEQUENCE: 17
agatctcatt caccgacaat gaagaca                                         27

<210> SEQ ID NO 18
<211> LENGTH: 27
<212> TYPE: DNA
<213> ORGANISM: Artificial Sequence
<220> FEATURE:
<223> OTHER INFORMATION: synthetic primer

<400> SEQUENCE: 18
agatcttcaa cagtctaata cctatga                                         27

<210> SEQ ID NO 19
<211> LENGTH: 27
<212> TYPE: DNA
<213> ORGANISM: Artificial Sequence
<220> FEATURE:
<223> OTHER INFORMATION: synthetic primer

<400> SEQUENCE: 19
agatctcgaa tgctaccaca attccta                                         27

<210> SEQ ID NO 20
<211> LENGTH: 29
<212> TYPE: DNA
<213> ORGANISM: Artificial Sequence
<220> FEATURE:
<223> OTHER INFORMATION: synthetic primer

<400> SEQUENCE: 20
ctcgagtcac taaatgaaca aggacaata                                       29

<210> SEQ ID NO 21
<211> LENGTH: 37
<212> TYPE: DNA
<213> ORGANISM: Artificial Sequence
<220> FEATURE:
<223> OTHER INFORMATION: synthetic primer

<400> SEQUENCE: 21
ccgctcgagt taaataaaca aggataataa tgtgatc                              37

<210> SEQ ID NO 22
<211> LENGTH: 27
<212> TYPE: DNA
<213> ORGANISM: Artificial Sequence
<220> FEATURE:
<223> OTHER INFORMATION: synthetic primer

<400> SEQUENCE: 22
ctcgagacca tattatttgg tacaatc                                         27
```

```
<210> SEQ ID NO 23
<211> LENGTH: 25
<212> TYPE: DNA
<213> ORGANISM: Artificial Sequence
<220> FEATURE:
<223> OTHER INFORMATION: synthetic primer

<400> SEQUENCE: 23
ctcgagttgg tacaatcccg tttga                                            25

<210> SEQ ID NO 24
<211> LENGTH: 29
<212> TYPE: DNA
<213> ORGANISM: Artificial Sequence
<220> FEATURE:
<223> OTHER INFORMATION: synthetic primer

<400> SEQUENCE: 24
ctcgagactt gattgaatta taccatata                                        29

<210> SEQ ID NO 25
<211> LENGTH: 27
<212> TYPE: DNA
<213> ORGANISM: Artificial Sequence
<220> FEATURE:
<223> OTHER INFORMATION: synthetic primer

<400> SEQUENCE: 25
ctcgagtctt agcaccctga cgtagct                                          27
```